(12) United States Patent
Gao et al.

(10) Patent No.: US 12,129,479 B2
(45) Date of Patent: Oct. 29, 2024

(54) GENOME EDITING METHOD

(71) Applicant: SUZHOU QI BIODESIGN BIOTECHNOLOGY COMPANY LIMITED, Suzhou (CN)

(72) Inventors: Caixia Gao, Beijing (CN); Huawei Zhang, Beijing (CN); Dingbo Zhang, Beijing (CN)

(73) Assignee: SUZHOU QI BIODESIGN BIOTECHNOLOGY COMPANY LIMITED, Jiangsu (CN)

( * ) Notice: Subject to any disclaimer, the term of this patent is extended or adjusted under 35 U.S.C. 154(b) by 51 days.

(21) Appl. No.: 18/130,300

(22) Filed: Apr. 3, 2023

(65) Prior Publication Data
US 2024/0011052 A1 Jan. 11, 2024

Related U.S. Application Data

(63) Continuation of application No. 16/487,024, filed as application No. PCT/CN2018/076949 on Feb. 22, 2018, now abandoned.

(30) Foreign Application Priority Data

Feb. 20, 2017 (CN) .......................... 201710089494.9

(51) Int. Cl.
| | | |
|---|---|---|
| *C12N 15/90* | (2006.01) | |
| *A01H 1/06* | (2006.01) | |
| *C12N 9/22* | (2006.01) | |
| *C12N 15/01* | (2006.01) | |
| *C12N 15/113* | (2010.01) | |
| *C12N 15/82* | (2006.01) | |

(52) U.S. Cl.
CPC ............. *C12N 15/902* (2013.01); *C12N 9/22* (2013.01); *C12N 15/113* (2013.01); *C12N 15/8213* (2013.01); *C12N 2310/20* (2017.05); *C12N 2310/3519* (2013.01)

(58) Field of Classification Search
None
See application file for complete search history.

(56) References Cited

U.S. PATENT DOCUMENTS

2019/0300877 A1   10/2019   Bendezu et al.

FOREIGN PATENT DOCUMENTS

| CN | 105934516 A | 9/2016 |
| CN | 107475256 A | 12/2017 |
| WO | 2016/061481 A1 | 4/2016 |
| WO | 2016/114972 A1 | 7/2016 |

OTHER PUBLICATIONS

Xie, K. et al., "Boosting CRISPR/Cas9 multiplex editing capability with the endogenous tRNA-processing system", PNAS, vol. 112, No. 11, Mar. 17, 2015, pp. 3570-3575.
Lee, R.T.H., et al., "Ribozyme Mediated gRNA Generation for In Vitro and In Vivo CRISPR/Cas9 Mutagenesis", PLoS One, vol. 11, No. 11, Nov. 10, 2016, pp. 1-12.
Slaymaker, I.M. et al., "Rationally engineered Cas9 nucleases with improved specificity", Science, vol. 351, issue 6268, Jan. 1, 2016, pp. 84-88.
Kleinstiver, B.P. et al., "High-fidelity CRISPR-Cas9 nucleases with no detectable genome-wide off target effects", Nature, vol. 529, Jan. 28, 2016, pp. 490-495.
Zhang, Dingbo et al., "Perfectly matched 20-nucleotide guide RNA Sequences enable robust genome editing using high-fidelity SpCas9 nucleases", Genome Biology, vol. 18, Oct. 11, 2017, pp. 1-7.
Gao et al., "Self-processing of ribozyme-flanked RNAs into guid RNAs in vitro and in vivo for CRISPR-mediated genome editing", Journal of Integrative Plant Biology, 2014, vol. 56, Issue 4, pp. 343-349.
Nakamura et al., "Codon usage tabulated from the international DNA sequence databases: status for the year 2000", Nucleic Acids Research, 2000, vol. 28,. No. 1, p. 292, 3 pages.
Wang et al., "Simultaneous editing of three homoeoalleles in hexaplold bread wheat confers heritable resistance to powdery mildew", Nature Biotechnology, 2014, vol. 32, No. 9, pp. 947-951.
Shan et al., "Targeted genome modification of crop plants using a CRISPR-Cas system", Nature Biotechnology, 2013, vol. 31, No. 8, pp. 686-688.
Liang et al., "Targeted mutagenesis in *Zea mays* using TALENs and the CRISPR/Cas system", Journal of Genetics and Genomics, 2014, vol. 41, pp. 63-68.
Shan et al., "Genome editing in rice and wheat using the CRISPR/Cas system", Nature Protocols, 2014, vol. 9, No. 10, pp. 2395-2410.
Liang et al., "Efficient DNA-free genome editing of bread wheat using CRISPR/Cas9 ribonucleoprotein complexes", Nature Communications, 2017, vol. 8, Article 14261, 5 pages.
International Search Report and Written Opinion Issued in PCT/CN2018/076949 dated May 30, 2018.

*Primary Examiner* — Suzanne M Noakes
*Assistant Examiner* — Jae W Lee
(74) *Attorney, Agent, or Firm* — Troutman Pepper Hamilton Sanders LLP

(57) ABSTRACT

The present invention relates to the field of genetic engineering. In particular, the present invention relates to a genome editing method with high efficiency and high specificity. More specifically, the present invention relates to a method for increasing the efficiency of site-directed modification of a target sequence in a genome of an organism by a high-specificity Cas9 nuclease variant.

7 Claims, 9 Drawing Sheets

Specification includes a Sequence Listing.

pUC57-U3-tRNA-sgRNA vector sequence::
(OsU3 promoter shown in bold; tRNA sequence shown in box; sgRNA scaffold shown in bold and Itali;
BsaI restriction site are underlined)

tcgcgcgtttcggtgatgacggtgaaaaccctctgacacatgcagctcccggagacggtcacagcttgtctgtaagcggatgccgggagcagacaa
gcccgtcagggcgcgtcagcgggtgttggcgggtgtcggggctggcttaactatgcggcatcagagcagattgtactgagagtgcaccagatgcg
gtgtgaaataccgcacagatgcgtaaggagaaaataccgcatcaggcgccattcgccattcaggctgcgcaactgttgggaaggcgatcggtgc
gggcctcttcgctattacgccagctggcgaaaggggggatgtgctgcaaggcgattaagttgggtaacgccagggttttcccagtcacgacgttgtaa
aacgacggccagtgcctgcaggtcgacgattaaggaatctttaaacatacgaacagatcacttaaagttcttctgaagcaacttaaagttatc
aggcatgcatggatcttggaggaatcagatgtgcagtcagggaccatagcacaagacaggcgtcttctactggtgctaccagcaaatgctg
gaagccgggaacactgggtacgtcggaaaccacgtgatgtgaagaagtaagataaactgtaggagaaaagcatttcgtagtgggccatg
aagcctttcaggacatgtattgcagtatgggccggcccattacgcaattggacgacaacaaagactagtattagtaccacctcggctatcca
catagatcaaagctgatttaaagagttgtgcagatgatccgtggc[aacaaagcaccagtggtctagtggtagaatagtaccctgccacggtac
agacccgggttcgattcccggctggtgca]agagaccgatatcccatggctcgaggg*tctcggtttagagctagaaatagcaagttaaaataagg*
*ctagtccgttatcaacttgaaaaagtggcaccgagtcggtgc*ttttttccacataatctctagaggatccccggcgtaatcatggtcatagctgtttcc
tgtgtgaaattgttatccgctcacaattccacacaacatacgagccggaagcataaagtgtaaagcctggggtgcctaatgagtgagctaactcacatt
aattgcgttgcgctcactgcccgctttccagtcgggaaacctgtcgtgccagctgcattaatgaatcggccaacgcgcggggagaggcggtttgcgt
attgggcgctcttccgcttcctcgctcactgactcgctgcgctcggtcgttcggctgcggcgagcggtatcagctcactcaaaggcggtaatacggtt
atccacagaatcaggggataacgcaggaaagaacatgtgagcaaaaggccagcaaaaggccaggaaccgtaaaaaggccgcgttgctggcgtt
ttccataggctccgcccccctgacgagcatcacaaaaatcgacgctcaagtcagaggtggcgaaacccgacaggactataaagataccaggcgtt
tccccctggaagctccctcgtgcgctctcctgttccgaccctgccgcttaccggatacctgtccgcctttctcccttcgggaagcgtggcgctttctcat
agctcacgctgtaggtatctcagttcggtgtaggtcgttcgctccaagctgggctgtgtgcacgaaccccccgttcagcccgaccgctgcgccttatc
cggtaactatcgtcttgagtccaacccggtaagacacgacttatcgccactggcagcagccactggtaacaggattagcagagcgaggtatgtagg
cggtgctacagagttcttgaagtggtggcctaactacggctacactagaagaacagtatttggtatctgcgctctgctgaagccagttaccttcggaaa
aagagttggtagctcttgatccggcaaacaaaccaccgctggtagcggtggtttttttgtttgcaagcagcagattacgcgcagaaaaaaaggatctc
aagaagatcctttgatcttttctacggggtctgacgctcagtggaacgaaaactcacgttaagggattttggtcatgagattatcaaaaaggatcttcac
ctagatccttttaaattaaaaatgaagttttaaatcaaatctaaagtatatatgagtaaacttggtctgacagttaccaatgcttaatcagtgaggcacctatct
cagcgatctgtctatttcgttcatccatagttgcctgactccccgtcgtgtagataactacgatacgggagggcttaccatctggccccagtgctgcaat
gataccgcgactcccacgctcaccggctccagatttatcagcaataaaccagccagccggaagggccgagcgcagaagtggtcctgcaactttat
ccgcctccatccagtctattaattgttgccgggaagctagagtaagtagttcgccagttaatagtttgcgcaacgttgttgccattgctacaggcatcgt
ggtgtcacgctcgtcgtttggtatggcttcattcagctccggttcccaacgatcaaggcgagttacatgatcccccatgttgtgcaaaaaagcggttag
ctccttcggtcctccgatcgttgtcagaagtaagttggccgcagtgttatcactcatggttatggcagcactgcataattctcttactgtcatgccatccgt
aagatgcttttctgtgactggtgagtactcaaccaagtcattctgagaatagtgtatgcggcgaccgagttgctcttgcccggcgtcaatacgggataa
taccgcgccacatagcagaactttaaaagtgctcatcattggaaaacgttcttcggggcgaaaactctcaaggatcttaccgctgttgagatccagttc
gatgtaacccactcgtgcacccaactgatcttcagcatcttttactttcaccagcgtttctgggtgagcaaaaacaggaaggcaaaatgccgcaaaaa
agggaataagggcgacacggaaatgttgaatactcatactcttcctttttcaatattattgaagcatttatcagggttattgtctcatgagcggatacatatt
tgaatgtatttagaaaaataaacaaataggggttccgcgcacatttccccgaaaagtgccacctgacgtctaagaaaccattattatcatgacattaacc
tataaaaataggcgtatcacgaggccctttcgtc (SEQ ID NO: 11)

GENOME EDITING METHOD

CROSS-REFERENCE TO RELATED APPLICATIONS

This application is a continuation of U.S. application Ser. No. 16/487,024, filed Aug. 19, 2019, which is a U.S. National Phase of International Patent Application No. PCT/CN2018/076949, filed Feb. 22, 2018, which claims priority to Chinese Patent Application No. 201710089494.9, filed Feb. 20, 2017, each of which are herein incorporated by reference in their entireties.

FIELD OF THE INVENTION

The present invention relates to the field of genetic engineering. In particular, the present invention relates to a genome editing method with high efficiency and high specificity. More specifically, the present invention relates to a method for increasing the efficiency of site-directed modification of a target sequence in a genome of an organism by a high-specificity Cas9 nuclease variant.

SEQUENCE LISTING

This application contains a computer readable Sequence Listing which has been submitted electronically in XML format and is hereby incorporated by reference in its entirety. The XML file was created on Sep. 29, 2023, is named Sequence_List_260109_000006.xml and is 130,082 bytes in size.

BACKGROUND OF THE INVENTION

Clustered regularly interspaced short palindromic repeats and CRISPR associated system (CRISPR/Cas9) is the most popular tool for genome editing. In the system, Cas9 protein cleaves a specific DNA sequence under the guidance of a gRNA to create a double-strand break (DSB). DSB can activate intracellular repair mechanisms of non-homologous end joining (NHEJ) and homologous recombination (HR) to repair DNA damage in cells such that the specific DNA sequence is edited during the repair process. Currently, the most commonly used Cas9 protein is Cas9 derived from *Streptococcus pyogenes* (SpCas9). One disadvantage of the CRISPR/Cas9 genome editing system is its low specificity and off-target effect, which greatly limit the application thereof.

There remains a need in the art for a method and tool that allow for efficient, high-specific genome editing.

SUMMARY OF THE INVENTION

In one aspect, the present invention provides a genome editing system for site-directed modification of a target sequence in the genome of a cell, which comprises at least one selected from the following i) to iii):
  i) a Cas9 nuclease variant, and an expression construct comprising a nucleotide sequence encoding a tRNA-guide RNA fusion;
  ii) an expression construct comprising a nucleotide sequence encoding a Cas9 nuclease variant, and an expression construct comprising a nucleotide sequence encoding a tRNA-guide RNA fusion; and
  iii) an expression construct comprising a nucleotide sequence encoding a Cas9 nuclease variant and a nucleotide sequence encoding a tRNA-guide RNA fusion;

wherein the Cas9 nuclease variant has higher specificity as compared with the wild-type Cas9 nuclease,
wherein the 5' end of the guide RNA is linked to the 3' end of the tRNA,
wherein the fusion is cleaved at the 5' end of the guide RNA after being transcribed in the cell, thereby forming a guide RNA that does not carry extra nucleotide at the 5' end.

In a second aspect, the present invention provides a genome editing system for site-directed modification of a target sequence in the genome of a cell, which comprises at least one selected from the following i) to iii):
  i) a Cas9 nuclease variant, and an expression construct comprising a nucleotide sequence encoding a ribozyme-guide RNA fusion;
  ii) an expression construct comprising a nucleotide sequence encoding a Cas9 nuclease variant, and an expression construct comprising a nucleotide sequence encoding a ribozyme-guide RNA fusion; and
  iii) an expression construct comprising a nucleotide sequence encoding a Cas9 nuclease variant and a nucleotide sequence encoding a ribozyme-guide RNA fusion;

wherein the Cas9 nuclease variant has higher specificity as compared with the wild-type Cas9 nuclease,
wherein the 5' end of the guide RNA is linked to the 3' end of a first ribozyme,
wherein the first ribozyme is designed to cleave the fusion at the 5' end of the guide RNA, thereby forming a guide RNA that does not carry extra nucleotide at the 5' end.

In a third aspect, the present invention provides a method for genetically modifying a cell, comprising introducing the genome editing system of the present invention into the cell, whereby the Cas9 nuclease variant is targeted to a target sequence in the genome of the cell by the guide RNA, and results in substitution, deletion and/or addition of one or more nucleotides in the target sequence.

In a fourth aspect, the present invention provides a genetically modified organism, which comprises a genetically modified cell produced by the method of the present invention.

BRIEF DESCRIPTION OF THE DRAWINGS

In FIG. 7A, the sequences listed are SEQ ID NOS: 23 and 65-83 in the order shown. In FIG. 7B, the sequences listed are also SEQ ID NOS: 23 and 65-83 in the order shown.

FIG. 9 shows the sequence structure of pUC57-U3-tRNA-sgRNA vector for tRNA-sgRNA fusion expression.

DETAILED DESCRIPTION OF THE INVENTION

1. Definition

Figure 1A:
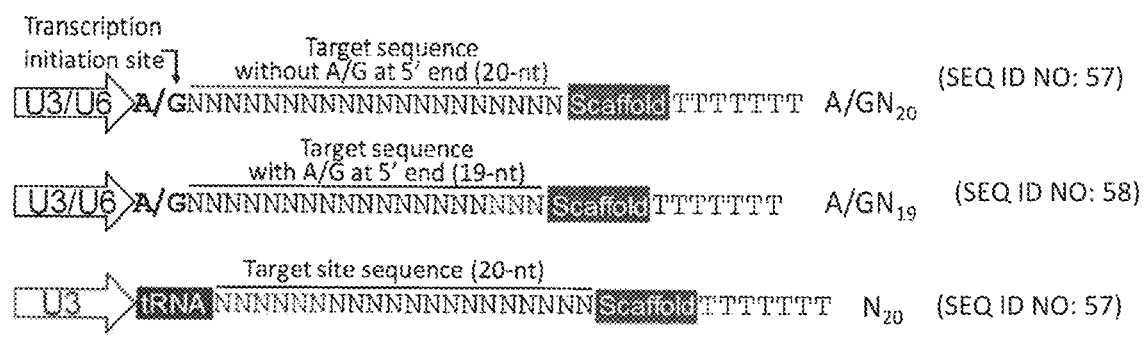
FIGS. 1A and 1B show the strategies for designing sgRNA for target sequences with different 5' end nucleotides when using U3 or U6. A: by fusion with tRNA, sgRNA can be designed without considering the 5' end nucleotide of the target sequence; B: precise cleavage of tRNA-sgRNA fusion.

In the present invention, unless indicated otherwise, the scientific and technological terminologies used herein refer to meanings commonly understood by a person skilled in the art. Also, the terminologies and experimental procedures used herein relating to protein and nucleotide chemistry, molecular biology, cell and tissue cultivation, microbiology, immunology, all belong to terminologies and conventional methods generally used in the art. For example, the standard DNA recombination and molecular cloning technology used herein are well known to a person skilled in the art, and are described in details in the following references: Sambrook, J., Fritsch, E. F. and Maniatis, T., Molecular Cloning: A Laboratory Manual; Cold Spring Harbor Laboratory Press: Cold Spring Harbor, 1989. In the meantime, in order to better understand the present invention, definitions and explanations for the relevant terminologies are provided below.

"Cas9 nuclease" and "Cas9" can be used interchangeably herein, which refer to a RNA directed nuclease, including the Cas9 protein or fragments thereof (such as a protein comprising an active DNA cleavage domain of Cas9 and/or a gRNA binding domain of Cas9). Cas9 is a component of the CRISPR/Cas (clustered regularly interspaced short palindromic repeats and its associated system) genome editing system, which targets and cleaves a DNA target sequence to form a DNA double strand breaks (DSB) under the guidance of a guide RNA.

"guide RNA" and "gRNA" can be used interchangeably herein, which typically are composed of crRNA and tracrRNA molecules forming complexes through partial complement, wherein crRNA comprises a sequence that is sufficiently complementary to a target sequence for hybridization and directs the CRISPR complex (Cas9+crRNA+tracrRNA) to specifically bind to the target sequence. However, it is known in the art that single guide RNA (sgRNA) can be designed, which comprises the characteristics of both crRNA and tracrRNA.

As used herein, the terms "tRNA" and "transfer RNA" are used interchangeably to refer to small molecule RNAs that have the function of carrying and transporting amino acids. The tRNA molecule usually consists of a short chain of about 70-90 nucleotides folded into a clover shape. In eukaryotes, tRNA genes in the genome are transcribed into tRNA precursors, which are then processed into mature tRNA after excision of the 5' and 3' additional sequences by RNase P and RNase Z.

As used herein, the term "ribozyme" refers to an RNA molecule that has a catalytic function which participates in the cleavage and processing of RNA by catalyzing the transphosphate and phosphodiester bond hydrolysis reactions.

"Genome" as used herein encompasses not only chromosomal DNA present in the nucleus, but also organelle DNA present in the subcellular components (e.g., mitochondria, plastids) of the cell.

As used herein, "organism" includes any organism that is suitable for genomic editing. Exemplary organisms include, but are not limited to, mammals such as human, mouse, rat, monkey, dog, pig, sheep, cattle, cat; poultry such as chicken, duck, goose; plants including monocots and dicots such as rice, corn, wheat, sorghum, barley, soybean, peanut, *Arabidopsis* and the like.

"Genetically modified organism" or "genetically modified cell" means an organism or cell that contains an exogenous polynucleotide or modified gene or expression control sequence within its genome. For example, the exogenous polynucleotide is stably integrated into the genome of an organism or cell and inherited for successive generations. The exogenous polynucleotide can be integrated into the genome alone or as part of a recombinant DNA construct. The modified gene or expression control sequence is the sequence in the genome of the organism or cell that comprises single or multiple deoxynucleotide substitutions, deletions and additions.

The term "exogenous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

As used herein, an "expression construct" refers to a vector suitable for expression of a nucleotide sequence of interest in an organism, such as a recombinant vector. "Expression" refers to the production of a functional product. For example, the expression of a nucleotide sequence may refer to transcription of the nucleotide sequence (such as transcribe to produce an mRNA or a functional RNA) and/or translation of RNA into a protein precursor or a mature protein.

"Expression construct" of the invention may be a linear nucleic acid fragment, a circular plasmid, a viral vector, or, in some embodiments, an RNA that can be translated (such as an mRNA).

"Expression construct" of the invention may comprise regulatory sequences and nucleotide sequences of interest that are derived from different sources, or regulatory sequences and nucleotide sequences of interest derived from the same source, but arranged in a manner different than that normally found in nature.

"Regulatory sequence" or "regulatory element" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a nucleic acid fragment capable of controlling the transcription of another nucleic acid fragment. In some embodiments of the present invention, the promoter is a promoter capable of controlling the transcription of a gene in a cell, whether or not it is derived from the cell. The promoter may be a constitutive promoter or a tissue-specific promoter or a developmentally-regulated promoter or an inducible promoter.

"Constitutive promoter" refers to a promoter that may cause expression of a gene in most circumstances in most cell types. "Tissue-specific promoter" and "tissue-preferred promoter" are used interchangeably, and refer to a promoter that is expressed predominantly but not necessarily exclusively in one tissue or organ, but that may also be expressed in one specific cell or cell type. "Developmentally regulated promoter" refers to a promoter whose activity is determined by developmental events. "Inducible promoter" selectively expresses a DNA sequence operably linked to it in response to an endogenous or exogenous stimulus (environment, hormones, or chemical signals, and so on).

As used herein, the term "operably linked" means that a regulatory element (for example but not limited to, a promoter sequence, a transcription termination sequence, and so on) is associated to a nucleic acid sequence (such as a coding sequence or an open reading frame), such that the transcription of the nucleotide sequence is controlled and regulated by the transcriptional regulatory element. Techniques for operably linking a regulatory element region to a nucleic acid molecule are known in the art.

"Introduction" of a nucleic acid molecule (e.g., plasmid, linear nucleic acid fragment, RNA, etc.) or protein into an organism means that the nucleic acid or protein is used to transform a cell of the organism such that the nucleic acid or protein functions in the cell. As used in the present invention, "transformation" includes both stable and transient transformations. "Stable transformation" refers to the introduction of an exogenous nucleotide sequence into the genome, resulting in the stable inheritance of foreign genes. Once stably transformed, the exogenous nucleic acid sequence is stably integrated into the genome of the organism and any of its successive generations. "Transient transformation" refers to the introduction of a nucleic acid molecule or protein into a cell, performing its function without the stable inheritance of an exogenous gene. In transient transformation, the exogenous nucleic acid sequence is not integrated into the genome.

2. Genome Editing System with High Efficiency and High Specificity

It has been reported that the Cas9 nuclease variant eSpCas9 (1.0) (K810A/K1003A/R1060A), eSpCas9(1.1) (K848A/K1003A/R1060A) of Feng Zhang et al., and the Cas9 nuclease variant SpCas9-HF1 (N497A/R661A/Q695A/Q926A) developed by J. Keith Joung et al., are capable of significantly reducing the off-target rate in genomic editing, and thus have high specificity. However, surprisingly, the present inventors found that these three Cas9 nuclease variants, while having high specificity, have a much lower gene editing efficiency compared to wild-type Cas9.

The present inventors have surprisingly found that by fusing the 5' end of the guide RNA to a tRNA, the editing efficiency of the high-specificity Cas9 nuclease variant can be increased, even to the wild-type level, while maintaining the high specificity.

Not intended to be limited by any theory, it is believed that the editing efficiency reduction of high-specificity Cas9 nuclease variants is related to whether the transcription of guide RNA can be precisely initiated or not. In the art, commonly used promoters for producing guide RNA in vivo include for example U6 or U3 snRNA promoters, for which the transcription is driven by RNA polymerase III. U6 promoter needs to initiate transcription at G, and thus for the target sequences with the first nucleotide of A, C or T, an additional G will be present at 5' end of sgRNA as transcribed. U3 promoter initiates transcription at A, and thus for the target sequences with the first nucleotide of G, C or T, an additional A will be present at 5' end of sgRNA as transcribed. The inventors found that, the editing efficiency of high-specificity Cas9 nuclease variants is reduced in the case that an additional nucleotide is present at 5' end of the sgRNA. By fusion transcription with a tRNA, due to the mechanism of precisely processing tRNA (precisely removing additional sequence of 5' and 3' of tRNA precursor to form mature tRNA), sgRNA without additional nucleotide at 5' end can be readily obtained even using U6 or U3 promoters, without the need of considering the type of the first nucleotide of the target sequence. Thereby, the editing efficiency of high specificity Cas9 nuclease variants can be improved, and the selectable range of target sequences can be extended. In addition, not intended to be limited by any theory, fusion with tRNA can increase the expression level of sgRNA, which may also contribute to the improvement of editing efficiency of high-specificity Cas9 nuclease variants.

Therefore, the present invention provides a genome editing system for site-directed modification of a target sequence in the genome of a cell, which comprises at least one selected from the following i) to iii):
  i) a Cas9 nuclease variant, and an expression construct comprising a nucleotide sequence encoding a tRNA-guide RNA fusion;
  ii) an expression construct comprising a nucleotide sequence encoding a Cas9 nuclease variant, and an expression construct comprising a nucleotide sequence encoding a tRNA-guide RNA fusion; and
  iii) an expression construct comprising a nucleotide sequence encoding a Cas9 nuclease variant and a nucleotide sequence encoding a tRNA-guide RNA fusion;
  wherein the Cas9 nuclease variant has higher specificity as compared with the wild-type Cas9 nuclease,
  wherein the 5' end of the guide RNA is linked to the 3' end of the tRNA,
  wherein the fusion is cleaved at the 5' end of the guide RNA after being transcribed in the cell, thereby forming a guide RNA that does not carry extra nucleotide at the 5' end.

In some embodiments, the tRNA and the cell to be modified are from the same species.

In some specific embodiments, the tRNA is encoded by the following sequence: aacaaagcaccagtggtctagtggtagaatagtaccctgccacggtaca-gacccgggttcgattcccggctggtgca (SEQ ID NO:1).

The design of the tRNA-guide RNA fusion is within the skill of the person in the art. For example, reference can be made to Xie et al., PNAS, Mar. 17, 2015; vol. 112, no. 11, 3570-3575.

The present invention also considers the fusion of a guide RNA and a ribozyme. On the basis that it is found in the invention that the editing efficiency of high-specificity Cas9 nuclease variants is related to precise transcription initiation of sgRNA, by using the ability of ribozyme to cut RNA at specific site, it is possible to produce sgRNA without additional nucleotide at 5' end by rational design of a fusion of RNA and ribozyme, so as to improve editing efficiency while maintain the high specificity.

Therefore, the invention also provides a genome editing system for site-directed modification of a target sequence in the genome of a cell, which comprises at least one selected from the following i) to iii):
  i) a Cas9 nuclease variant, and an expression construct comprising a nucleotide sequence encoding a ribozyme-guide RNA fusion;
  ii) an expression construct comprising a nucleotide sequence encoding a Cas9 nuclease variant, and an expression construct comprising a nucleotide sequence encoding a ribozyme-guide RNA fusion; and
  iii) an expression construct comprising a nucleotide sequence encoding a Cas9 nuclease variant and a nucleotide sequence encoding a ribozyme-guide RNA fusion;
  wherein the Cas9 nuclease variant has higher specificity as compared with the wild-type Cas9 nuclease,
  wherein the 5' end of the guide RNA is linked to the 3' end of a first ribozyme,
  wherein the first ribozyme is designed to cleave the fusion at the 5' end of the guide RNA, thereby forming a guide RNA that does not carry extra nucleotide at the 5' end.

In one embodiment, the 3' end of the guide RNA is linked to the 5' end of a second ribozyme, the second ribozyme is designed to cleave the fusion at the 3' end of the guide RNA, thereby forming a guide RNA that does not carry extra nucleotide at the 3' end.

The design of the first ribozyme or the second ribozyme is within the skill of the person in the art. For example, reference can be made to Gao et al., JIPB, April, 2014; Vol 56, Issue 4, 343-349.

In one specific embodiment, the first ribozyme is encoded by the following sequence: 5'-(N)$_6$CTGATGAGTCCGT-GAGGACGAAACGAGTAAGCTCGTC-3' (SEQ ID NO: 12), wherein N is independently selected from A, G, C, and T, and (N)$_6$ refers to a sequence reversely complementary to the first 6 nucleotides at 5' end of the guide RNA. In one specific embodiment, the second ribozyme is encoded by the following sequence: 5'-GGCCGG-CATGGTCCCAGCCTCCTCGCTGGCGCCGGCTGG-GCAACATGCTTCGGCATGGCGAATGGGAC-3' (SEQ ID NO: 13).

The Cas9 nuclease variant in the invention that has higher specificity as compared with wild type Cas9 nuclease can be derived from Cas9 of various species, for example, derived from Cas9 of *Streptococcus pyogenes* (SpCas9, nucleotide sequence shown in SEQ ID NO:2, amino acid sequence shown in SEQ ID NO:3).

In some embodiments of the invention, the Cas9 nuclease variant is a variant of SEQ ID NO:2, which comprises an amino acid substitution at position 855 of SEQ ID NO:2. In some specific embodiments, the amino acid substitution at position 855 is K855A.

In some embodiments of the invention, the Cas9 nuclease variant is a variant of SEQ ID NO:2, which comprises amino acid substitutions at positions 810, 1003 and 1060 of SEQ ID NO:2. In some specific embodiments, the amino acid substitutions respectively are K810A, K1003A and R1060A.

In some embodiments of the invention, the Cas9 nuclease variant is a variant of SEQ ID NO:2, which comprises amino acid substitutions at positions 848, 1003 and 1060 of SEQ ID NO:2. In some specific embodiments, the amino acid substitutions respectively are K848A, K1003A and R1060A.

In some embodiments of the invention, the Cas9 nuclease variant is a variant of SEQ ID NO:2, which comprises amino acid substitutions at positions 611, 695 and 926 of SEQ ID NO:2. In some specific embodiments, the amino acid substitutions respectively are R611A, Q695A and Q926A.

In some embodiments of the invention, the Cas9 nuclease variant is a variant of SEQ ID NO:2, which comprises amino acid substitutions at positions 497, 611, 695 and 926 of SEQ ID NO:2. In some specific embodiments, the amino acid substitutions respectively are N497A, R611A, Q695A and Q926A.

In some specific embodiments of the invention, the Cas9 nuclease variant comprises an amino acid sequence as shown in SEQ ID NO:4 (eSpCas9(1.0)), SEQ ID NO:5 (eSpCas9(1.1)) or SEQ ID NO:6 (SpCas9-HF1).

In some embodiments of the invention, the Cas9 nuclease variant of the invention further comprises a nuclear localization sequence (NLS). In general, one or more NLSs in the Cas9 nuclease variant should have sufficient strength to drive the accumulation of the Cas9 nuclease variant in the nucleus of the cell in an amount sufficient for the genome editing function. In general, the strength of the nuclear localization activity is determined by the number and position of NLSs, and one or more specific NLSs used in the Cas9 nuclease variant, or a combination thereof.

In some embodiments of the present invention, the NLSs of the Cas9 nuclease variant of the invention may be located at the N-terminus and/or the C-terminus. In some embodiments, the Cas9 nuclease variant comprises about 1, 2, 3, 4, 5, 6, 7, 8, 9, 10, or more NLSs. In some embodiments, the Cas9 nuclease variant comprises about 1, 2, 3, 4, 5, 6, 7, 8, 9, 10, or more NLSs at or near the N-terminus. In some embodiments, the Cas9 nuclease variant comprises about 1, 2, 3, 4, 5, 6, 7, 8, 9, 10, or more NLSs at or near the C-terminus. In some embodiments, the Cas9 nuclease variant comprises a combination of these, such as one or more NLSs at the N-terminus and one or more NLSs at the C-terminus. Where there are more than one NLS, each NLS may be selected as independent from other NLSs. In some preferred embodiments of the invention, the Cas9 nuclease variant comprises two NLSs, for example, the two NLSs are located at the N-terminus and the C-terminus, respectively.

In general, NLS consists of one or more short sequences of positively charged lysine or arginine exposed on the surface of a protein, but other types of NLS are also known in the art. Non-limiting examples of NLSs include KKRKV (nucleotide sequence 5'-AAGAAGAGAAAGGTC-3' (SEQ ID NO: 14)), PKKKRKV(nucleotide sequence 5'-CC-CAAGAAGAAGAGGAAGGTG-3' (SEQ ID NO: 15) or CCAAAGAAGAAGAGGAAGGTT (SEQ ID NO: 16), or SGGSPKKKRKV (SEQ ID NO: 17) (nucleotide sequence 5'-TCGGGGGGGAGCCCAAAGAAGAAGCG-GAAGGTG-3') (SEQ ID NO: 18).

In some embodiments of the invention, the N-terminus of the Cas9 nuclease variant comprises an NLS with an amino acid sequence shown by PKKKRKV (SEQ ID NO: 19). In some embodiments of the invention, the C-terminus of the Cas9 nuclease variant comprises an NLS with an amino acid sequence shown by SGGSPKKKRKV (SEQ ID NO: 17).

In addition, the Cas9 nuclease variant of the present invention may also include other localization sequences, such as cytoplasmic localization sequences, chloroplast localization sequences, mitochondrial localization sequences, and the like, depending on the location of the DNA to be edited.

For obtaining effective expression in the target cell, in some embodiments of the invention, the nucleotide sequence encoding the Cas9 nuclease variant is codon-optimized for the organism where the cell to be genome-edited is from.

Codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/ and these tables can be adapted in a number of ways. See Nakamura, Y., et al. "Codon usage tabulated from the international DNA sequence databases: status for the year 2000" Nucl. Acids Res. 28:292 (2000).

The organism, from which the cell that can be genome edited by the system of the invention is derived, includes but is not limited to, mammals such as human, mice, rat, monkey, dog, pig, sheep, cow and cat; poultry such as chicken, duck and goose; plants including monocotyledons and dicotyledons, e.g. rice, maize, wheat, sorghum, barley, soybean, peanut and *Arabidopsis thaliana* and the like.

In some specific embodiments of the invention, the codon-optimized nucleotide sequence encoding the Cas9 nuclease variant is as shown in SEQ ID NO:7(eSpCas9 (1.0)), SEQ ID NO:8(eSpCas9(1.1)) or SEQ ID NO:9(SpCas9-HF1).

In some embodiments of the invention, the guide RNA is a single guide RNA (sgRNA). Methods of constructing suitable sgRNAs according to a given target sequence are known in the art. See e.g., Wang, Y. et al. Simultaneous editing of three homoeoalleles in hexaploid bread wheat confers heritable resistance to powdery mildew. Nat. Biotechnol. 32, 947-951 (2014); Shan, Q. et al. Targeted genome modification of crop plants using a CRISPR-Cas system. Nat. Biotechnol. 31, 686-688 (2013); Liang, Z. et al. Targeted mutagenesis in *Zea mays* using TALENs and the CRISPR/Cas system. J Genet Genomics. 41, 63-68 (2014).

In some embodiments of the invention, the nucleotide sequence encoding the Cas9 nuclease variant and/or the nucleotide sequence encoding the guide RNA fusion are operatively linked to an expression regulatory element such as a promoter.

Examples of promoters that can be used in the present invention include but are not limited to polymerase (pol) I, pol II or pol III promoters. Examples of pol I promoters include chicken RNA pol I promoter. Examples of pol II promoters include but are not limited to cytomegalovirus immediate early (CMV) promoter, rous sarcoma virus long terminal repeat (RSV-LTR) promoter and simian virus 40(SV40) immediate early promoter. Examples of pol III promoters include U6 and H1 promoter. Inducible promoter such as metalothionein promoter can be used. Other examples of promoters include T7 bacteriophage promoter, T3 bacteriophage promoter, β-galactosidase promoter and Sp6 bacteriophage promoter etc. When used for plants, promoters that can be used include but are not limited to cauliflower mosaic virus 35S promoter, maize Ubi-1 promoter, wheat U6 promoter, rice U3 promoter, maize U3 promoter and rice actin promoter etc.

3. Method for Genetically Modifying a Cell

In another aspect, the invention provides a method for genetically modifying a cell, comprising: introducing the genome editing system of the invention to the cell, thereby the Cas9 nuclease variant is targeted to the target sequence in the genome of the cell by the guide RNA, and results in substitution, deletion and/or addition of one or more nucleotides in the target sequence.

The design of the target sequence that can be recognized and targeted by a Cas9 and guide RNA complex is within the technical skills of one of ordinary skill in the art. In general, the target sequence is a sequence that is complementary to a leader sequence of about 20 nucleotides comprised in guide RNA, and the 3'-end of which is immediately adjacent to the protospacer adjacent motif (PAM) NGG.

For example, in some embodiments of the invention, the target sequence has the structure: 5'-$N_x$-NGG-3', wherein N is selected independently from A, G, C, and T; X is an integer of $14 \leq X \leq 30$; NX represents X contiguous nucleotides, and NGG is a PAM sequence. In some specific embodiments of the invention, X is 20.

In the present invention, the target sequence to be modified may be located anywhere in the genome, for example, within a functional gene such as a protein-coding gene or, for example, may be located in a gene expression regulatory region such as a promoter region or an enhancer region, and thereby accomplish the functional modification of said gene or accomplish the modification of a gene expression.

The substitution, deletion and/or addition in the target sequence of the cell can be detected by T7EI, PCR/RE or sequencing methods, see e.g., Shan, Q., Wang, Y., Li, J. & Gao, C. Genome editing in rice and wheat using the CRISPR/Cas system. Nat. Protoc. 9, 2395-2410 (2014).

In the method of the present invention, the genome editing system can be introduced into the cell by using various methods well known by the skilled in the art.

Methods for introducing the genome editing system of the present invention into the cell include, but are not limited to calcium phosphate transfection, protoplast fusion, electroporation, liposome transfection, microinjection, viral infection (such as a baculovirus, a vaccinia virus, an adenovirus and other viruses), particle bombardment, PEG-mediated protoplast transformation or *Agrobacterium*-mediated transformation.

The cell which can be subjected to genome editing with the method of the present invention can be from, for example, mammals such as human, mouse, rat, monkey, dog, pig, sheep, cow and cat; poultry such as chicken, duck and goose; and plants including monocotyledons and dicotyledons such as rice, maize, wheat, sorghum, barley, soybean, peanut and *Arabidopsis thaliana* etc.

In some embodiments, the method of the present invention is performed in vitro. For example, the cell is an isolated cell. In some other embodiments, the method of the present invention can be performed in vivo. For example, the cell is a cell within an organism, and the system of the present invention can be introduced in-vivo into said cell by using, for example, a virus-mediated method. In some embodiments, the cell is a germ cell. In some implementations, the cell is a somatic cell.

In another aspect, the present invention further provides a genetically modified organism comprising a genetically modified cell produced by the method of the present invention.

The organism includes, but is not limited to mammals such as humans, mice, rats, monkeys, dogs, pigs, sheep, cows and cats; poultry such as chicken, ducks and geese; and plants including monocotyledons and dicotyledons such as rice, maize, wheat, sorghum, barley, soybean, peanuts and *Arabidopsis thaliana*.

EXAMPLES

Materials and Methods

Construction of Binary Expression Vectors pJIT163-SpCas9, pJIT163-eSpCas9(1.0), pJIT163-eSpCas9(1.1) and pJIT163-SpCas9-HF1

SpCas9, eSpCas9(1.0), eSpCas9(1.1) and SpCas9-HF1 sequences were codon-optimized for rice. SpCas9, eSpCas9 (1.0), eSpCas9(1.1) and SpCas9-HF1 were obtained by site-directed mutagenesis using Fast MultiSite Mutagenesis System (TransGen) with pJIT163-SpCas9 plasmid (SEQ ID NO: 10) as the template.

Construction of sgRNA Expression Vector sgRNA target sequences used in the experiments are showed in table 1 as follows:

TABLE 1

Target Gene and sgRNA Target Sequence

| sgRNA | Target sequence | Oligo-F | Oligo-R |
| --- | --- | --- | --- |
| OsCDKB2 | AGGTCGGGGAGGGGACGTACGGG (SEQ ID NO: 20) | GGCAAGGTCGGGGAGGGACGTAC (SEQ ID NO: 21) | AAACGTACGTCCCTCCCCGACCT (SEQ ID NO: 22) |
| OsMK4 | GACGTCGGCGAGGAAGGCCTCGG (SEQ ID NO: 23) | GGCAGACGTCGGCGAGGAAGGCCT (SEQ IN NO: 24) | AAACAGGCCTTCCTCGCCGACGTC (SEQ ID NO: 25) |
| A1 | CATGGTGGGGAAAGCTTGGAGGG (SEQ ID NO: 26) | GGCACATGGTGGGGAAAGCTTGGA (SEQ ID NO: 27) | AAACTCCAAGCTTTCCCCACCATG (SEQ ID NO: 28) |
| A2 | CCGGACGACGACGTCGACGACGG (SEQ ID NO: 29) | GGCACCGGACGACGACGTCGACGA (SEQ ID NO: 30) | AAACTCGTCGACGTCGTCGTCCGG (SEQ ID NO: 31) |
| A3 | TTGAAGTCCCTTCTAGATGGAGG (SEQ ID NO: 32) | GGCATTGAAGTCCCTTCTAGATGG (SEQ ID NO: 33) | AAACCCATCTAGAAGGGACTTCAA (SEQ ID NO: 34) |
| A4 | ACTGCGACACCCAGATATCGTGG (SEQ ID NO: 35) | GGCAACTGCGACACCCAGATATCG (SEQ ID NO: 36) | AAACCGATATCTGGGTGTCGCAGT (SEQ ID NO: 37) |
| PDS | GTTGGTCTTTGCTCCTGCAGAGG (SEQ ID NO: 38) | GGCAGTTGGTCTTTGCTCCTGCAG (SEQ ID NO: 39) | AAACCTGCAGGAGCAAAGACCAAC (SEQ ID NO: 40) | sgRNA expression vectors: pOsU3-CDKB2-sgRNA, pOsU3-MKK4-sgRNA, pOsU3-A1-sgRNA as well as pOsU3-A2-sgRNA, pOsU3-A3-sgRNA, pOsU3-A4-sgRNA and pOsU3-PDS-sgRNA are constructed on the basis of pOsU3-sgRNA (Addgene ID53063) as described previously (Shan, Q. et al. Targeted genome modification of crop plants using a CRISPR-Cas system. Nat. Biotechnol. 31, 686-688, 2013).

Figure 6A:
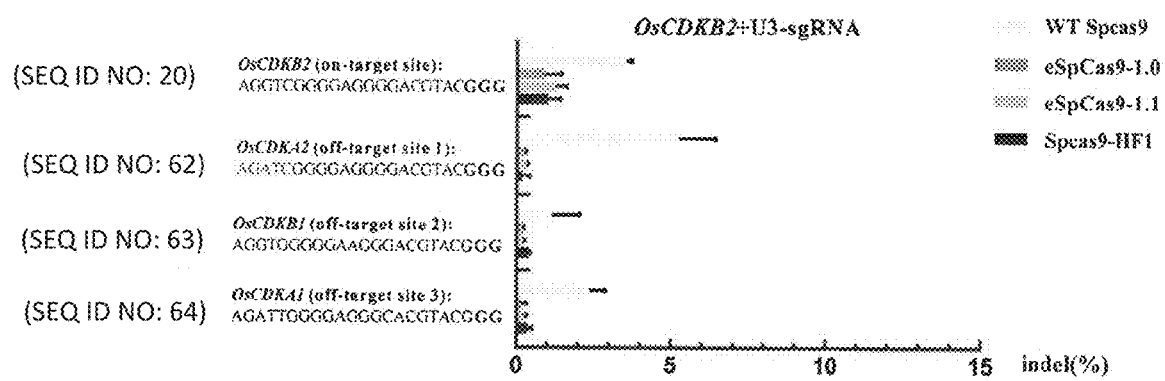
FIGS. 6A and 6B show that for the OsCDKB2 locus, the use of tRNA-sgRNA can increase the editing efficiency to the level of wild-type SpCas9, while maintaining high specificity.
Figure 6B:
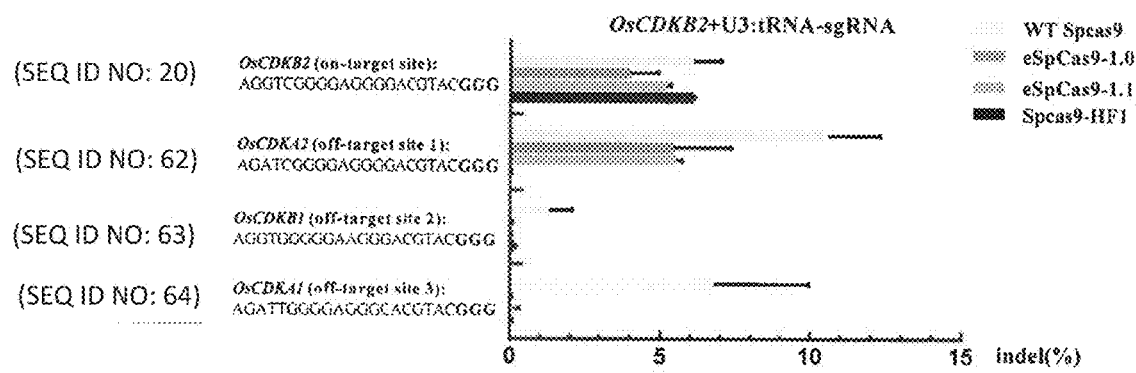

Construction of tRNA-sgRNA Expression Vectors tRNA-sgRNA expression vectors are constructed on the basis of the pUC57-U3-tRNA-sgRNA vector (SEQ ID NO: 11, FIG. 6). A linear vector is obtained after digestion of pUC57-U3-tRNA-sgRNA with BsaI, the corresponding oligo-F and oligo-R are annealed and connected into the linear vector, and the subsequent steps are similar to the construction of the sgRNA expression vectors.

TABLE 2

Target Genes and Oligonucleotide Sequences for Constructing tRNA-sgRNA Expression Vectors

| sgRNA | Target sequence | Oligo-F | Oligo-R |
|---|---|---|---|
| OsCDKB2 | AGGTCGGGGAGGGGACGTACGGG (SEQ ID NO: 20) | TGCAAGGTCGGGGAGGGGACGTAC (SEQ ID NO: 41) | AAACGTACGTCCCCTCCCCGACCT (SEQ ID NO: 22) |
| OsMKK4 | GACGTCGGCGAGGAAGGCCTCGG (SEQ ID NO: 23) | TGCAGACGTCGGCGAGGAAGGCCT (SEQ ID NO: 42) | AAACAGGCCTTCCTCGCCGACGTC (SEQ ID NO: 25) |
| A1 | CATGGTGGGGAAAGCTTGGAGGG (SEQ ID NO: 26) | TGCACATGGTGGGGAAAGCTTGGA (SEQ ID NO: 43) | AAACTCCAAGCTTTCCCCACCATG (SEQ ID NO: 28) |
| A2 | CCGGACGACGACGTCGACGACGG (SEQ ID NO: 29) | TGCACCGGACGACGACGTCGACGA (SEQ ID NO: 44) | AAACTCGTCGACGTCGTCGTCCGG (SEQ ID NO: 31) |
| A3 | TTGAAGTCCCTTCTAGATGGAGG (SEQ ID NO: 32) | TGCATTGAAGTCCCTTCTAGATGG (SEQ ID NO: 45) | AAACCCATCTAGAAGGGACTTCAA (SEQ ID NO: 34) |
| A4 | ACTGCGACACCCAGATATCGTGG (SEQ ID NO: 35) | TGCACTGCGACACCCAGATATCG (SEQ ID NO: 46) | AAACCGATATCTGGGTGTCGCAGT (SEQ ID NO: 37) |
| PDS | GTTGGTCTTTGCTCCTGCAGAGG (SEQ ID NO: 38) | TGCAGTTGGTCTTTGCTCCTGCAG (SEQ ID NO: 47) | AAACCTGCAGGAGCAAAGACCAAC (SEQ ID NO: 40) |

Protoplast Assays

Rice cultivar nipponbare is used in the research. Protoplasts transformation is performed as described below. Transformation is carried out with 10 μg of each plasmid by PEG-mediated transfection. Protoplasts were collected after 48 h and DNA was extracted for PCR-RE assay.

Preparation and Transformation of Rice Protoplast

1) Leaf sheath of the seedlings were used for protoplasts isolation, and cut into about 0.5 mm wide with a sharp blade.
2) Immediately after incision, transferred into 0.6M Mannitol solution, and placed in the dark for 10 min.
3) Mannitol solution was removed by filtration, and the products were transferred into enzymolysis solution, and evacuated for 30 min.
4) Enzymolysis was performed for 5-6 h in darkness with gently shaking (decolorization shaker, speed 10).
5) After enzymolysis completion, an equal volume of W5 was added, horizontal shake for 10 s to release protoplasts.
6) Protoplasts were filtered into a 50 ml round bottom centrifuge tube with a 40 μm nylon membrane and washed with W5 solution.
7) 250 g horizontal centrifugation for 3 min to precipitate the protoplasts, the supernatant was discarded.
8) Protoplasts were resuspended by adding 10 ml W5, and then centrifuged at 250 g for 3 min, and the supernatant was discarded.
9) An appropriate amount of MMG solution was added to resuspend the protoplasts to a concentration of $2 \times 10^6$/ml.

Note: All the above steps were carried out at room temperature.

10) 10-20 μg plasmid, 200 μl protoplasts (about $4 \times 10^5$ cells), and 220 μl fresh PEG solution were added into a 2 ml centrifugal tube, mixed, and placed at room temperature in darkness for 10-20 minutes to induce transformation.
11) After the completion of the transformation, 880 μl W5 solution was slowly added, and the tubes were gently turned upside down for mixing, 250 g horizontal centrifuged for 3 min, and the supernatant was discarded.
12) The products were resuspended in 2 ml WI solution, transferred to a six-well plate, cultivated in room temperature (or 25° C.) in darkness. For protoplast genomic DNA extraction, the products need to be cultivated for 48 h.

Mutation Identification by Deep Sequencing

Deep sequencing analysis is performed by reference to Liang, Z., Chen, K., Li, T., Zhang, Y., Wang, Y., Zhao, Q., Liu, J., Zhang, H., Liu, C., Ran, Y., et al. (2017). Efficient DNA-free genome editing of bread wheat using CRISPR/Cas9 ribonucleoprotein complexes. Nature Communications 8, 14261.

Example 1: Comparing Editing Capacities of WT SpCas9 and Variants Thereof to Target Sites WT SpCas9, eSpCas9(1.0), eSpCas9(1.1) and SpCas9-HF1 were respectively constructed in a transient expression vector pJIT163, and the expressions of WT SpCas9, eSpCas9(1.0), eSpCas9(1.1) and SpCas9-HF1 are driven by a maize ubiquitin gene promoter. sgRNAs were constructed in the pOsU3-sgRNA vector, and the expression of sgRNAs is driven by OsU3 promoter. Rice protoplasts were transformed, and protoplast DNA was extracted for PCR-RE analysis to evaluate the mutation efficiency. Five target sites (A1, A2, A3, A4 and PDS, see FIG. 2 and FIG. 3) are selected to compare the difference of editing capacities of wild-type SpCas9 and eSpCas9(1.0), eSpCas9(1.1) and SpCas9-HF1.

Figure 1B:
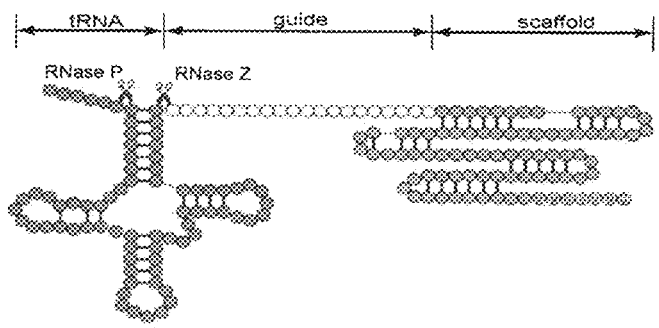

The OsU3 promoter has to initiate transcription with the nucleotide A, and therefore, the design of the sgRNA expression vectors for the target sites can be divided into two conditions as follows:

(1) If the first nucleotide at the 5' end of the desired sgRNA target sequence (20 bp) is any one of G/T/C, as the U3 promoter initiates transcription with an A, an additional A will be added to the 5' end of the transcribed sgRNA, and furthermore, the transcribed sgRNA cannot completely match with the target sequence. sgRNA expression vector can be constructed as U3+AN$_{20}$ in FIG. 1, while N$_{20}$ is the target sequence, A is the additional nucleotide at 5' end.

(2) If the first nucleotide at the 5' end of the desired sgRNA target sequence (20 bp) is A, it can used by the U3 promoter for initiating transcription, and therefore no additional nucleotide will exist at the 5' end of the transcribed sgRNA. sgRNA expression vector can be constructed as U3+AN$_{19}$ in FIG. 1, while AN$_{19}$ is the target sequence.

The selected target sites A1, A2, A3 and PDS belong to target sites of class (1), and target site A4 belongs to target sites of class (2).

The experiment results show (FIG. 2) that the editing efficiencies of eSpCas9(1.0), eSpCas9(1.1) and SpCas9-HF1 for the target sites of class (1) are extremely low. The difference of the editing efficiencies of eSpCas9(1.0), eSpCas9(1.1) and SpCas9-HF1 and the editing efficiency of WT SpCas9 is not significant for target sites of class (2). This shows that the additional nucleotide at the 5' end of the sgRNA resulted from the transcription can reduce the editing efficiencies of eSpCas9(1.0), eSpCas9(1.1) and SpCas9-HF1.

Similar to OsU3 promoter, maize U6 promoter (TaU6) has to initiate transcription with the nucleotide G, and therefore, the design of the sgRNA expression vectors for the target sites can be divided into two conditions as follows:

(1) If the first nucleotide at the 5' end of the desired sgRNA target sequence (20 bp) is any one of A/T/C, as the U6 promoter initiates transcription with a G, an additional G will be added to the 5' end of the transcribed sgRNA, and furthermore, the transcribed sgRNA cannot completely match with the target sequence.

(2) If the first nucleotide at the 5' end of the desired sgRNA target sequence (20 bp) is G, it can used by the U6 promoter for initiating transcription, and therefore no additional nucleotide will exist at the 5' end of the transcribed sgRNA.

The OsPDS target site belongs to target sites of class (2). TaU6 promoter was used to drive the transcription of GN$_{19}$ and GN$_{20}$ sgRNAs against OsPDS target site, where GN$_{20}$ can mimic the target sites of class (1), namely with an additional G at 5' end of the sgRNA.

TABLE 3

Target gene and oligonucleotide sequences for construction of TaU6-sgRNA expression vectors

| sgRNA | Target sequence | Oligo-F | Oligo-R |
|---|---|---|---|
| OsPDS-GN19 | GTTGGTCT TTGCTCC TGCAGAGG (SEQ ID NO. 38) | GGCGTTGGT CTTTGCTC CTGCAG (SEQ ID NO: 48) | AAACCTGC AGGAGCAA AGACCAA (SEQ ID NO: 40) |
| OsPDS-GN20 | GTTGGTCT TTGCTCC TGCAGAGG (SEQ ID NO: 38) | GGCGGTTGG TCTTTGCT CCTGCAG (SEQ ID NO: 49) | AAACCTGC AGGAGCAA AGACCAAC (SEQ ID NO: 40) |

The results show (FIG. 2) that one additional G at 5' end of the sgRNA significantly reduces the editing efficiency of eSpCas9(1.0), eSpCas9(1.1) and SpCas9-HF1.

Example 2: Increasing Editing Efficiency of Cas9 Variants by tRNA-sgRNA Fusion According to the result of the Example 1, an important factor influencing the editing efficiencies of eSpCas9(1.0), eSpCas9(1.1) and SpCas9-HF1 is weather the sgRNA is precisely initiated or not.

Figure 2:
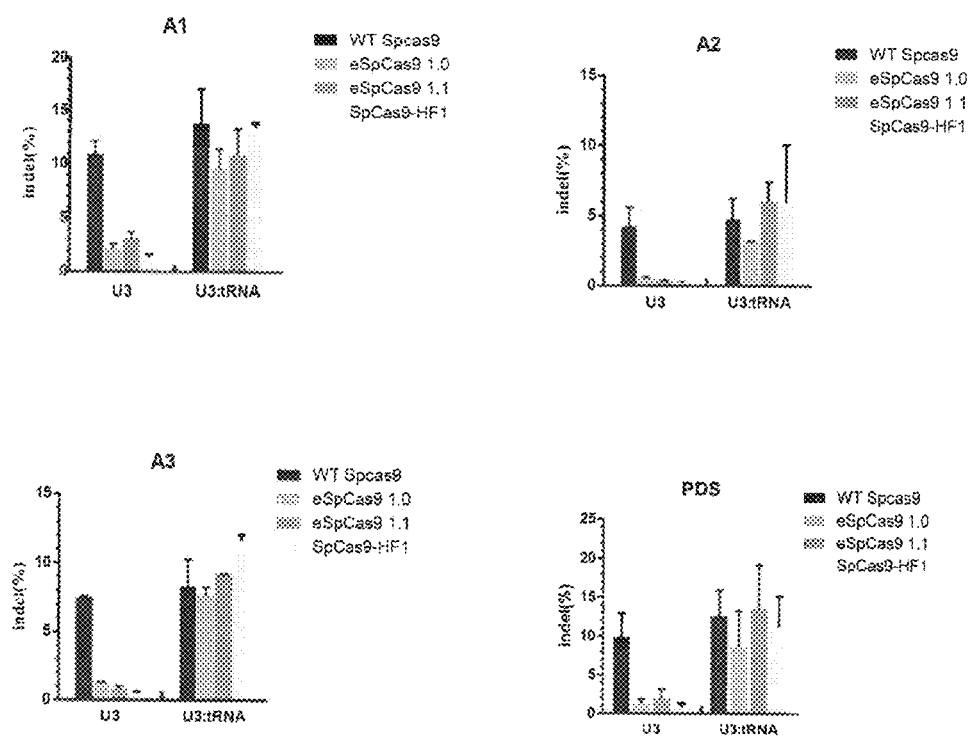
FIG. 2 shows the editing efficiency of WT SpCas9 (wild type SpCas9), eSpCas9(1.0), eSpCas9(1.1), SpCas9-HF1 on targets of class (1).
Figure 3:
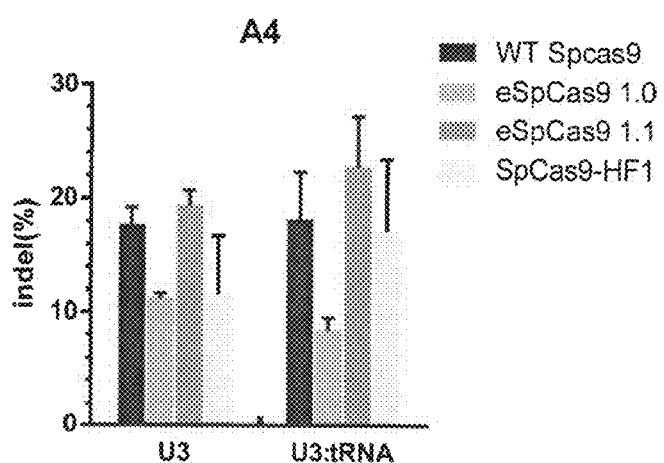
FIG. 3 shows the editing efficiency of WT SpCas9 (wild type SpCas9), eSpCas9(1.0), eSpCas9(1.1), SpCas9-HF1 on targets of class (2).
Figure 4:
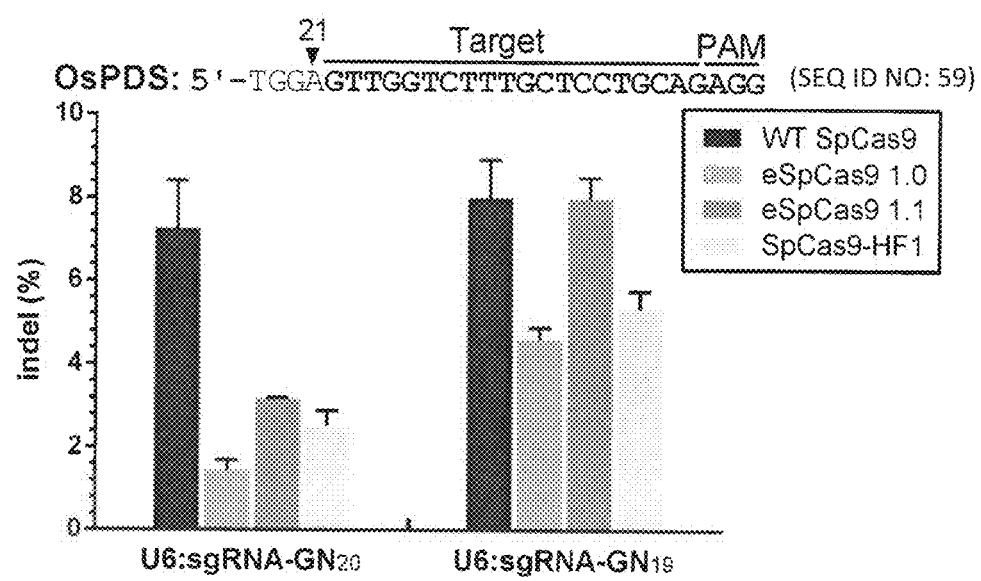
FIG. 4 shows that the additional nucleotide at 5' end of sgRNA affects the editing efficiency when U6 promoter is used.

According to previous report, fusion of a tRNA to the 5' end of an sgRNA may up-regulate the expression of the sgRNA and result in precise cleavage at the 5' end of the sgRNA, and thereby avoiding additional nucleotide at the 5' end of the sgRNA. (See Xie K, Minkenberg B, Yang Y. Boosting CRISPR/Cas9 multiplex editing capability with the endogenous tRNA-processing system. Proc Natl Acad Sci USA. 2015 Mar. 17; 112(11):3570-5. doi: 10.1073/pnas.1420294112. Epub 2015 Mar. 2.)

sgRNA for each target site in Example 1 was fused to tRNA and expressed under the control of the OsU3 promoter. Experiments were performed by the method in Example 1 with tRNA-sgRNAs instead of sgRNAs. As shown in FIG. 2, for the target sites A1, A2, A3 and PDS, the editing efficiencies of eSpCas9(1.0), eSpCas9(1.1) and SpCas9-HF1 are significantly increased using tRNA-sgRNAs instead of sgRNAs.

Example 3: Influences of tRNA-sgRNA Fusion to Editing Specificity of Cas9 Variants

3.1 Rice OsMKK4 Target Site

Figure 5A:
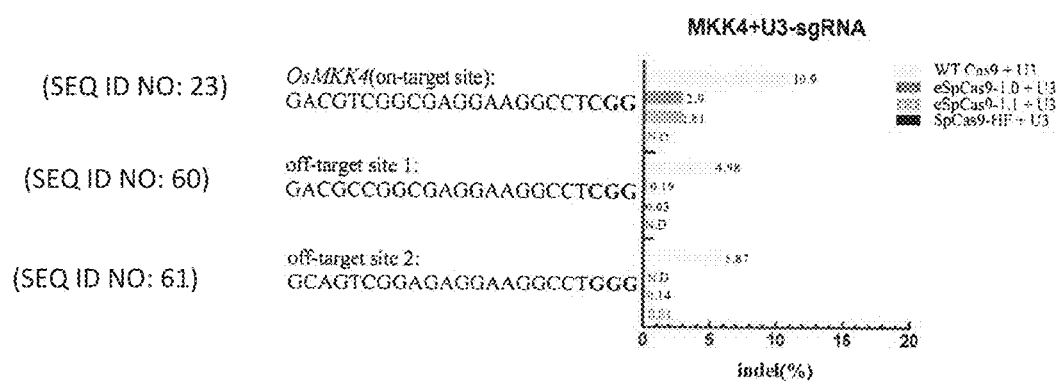
FIGS. 5A and 5B show that for the OsMKK4 locus, tRNA-sgRNA can improve the editing efficiency and maintain high specificity as compared to sgRNA.
Figure 5B:
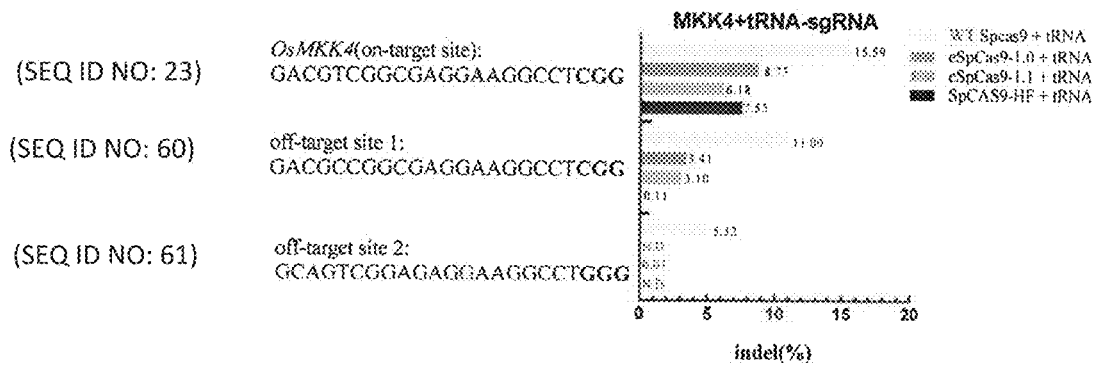

A target site GACGTCGGCGAGGAAGGCCTCGG (SEQ ID NO: 23) in rice gene MKK4 was selected to design sgRNA and tRNA-sgRNA. This target site has two possible off-target sites as shown in FIG. 5. A vector for expressing sgRNA or tRNA-sgRNA and vectors for expressing WTSpCas9, eSpCas9(1.0), eSpCas9(1.1) and SpCas9-HF1 were respectively co-transformed into rice protoplasts. Two days after transformation, protoplast DNA was extracted, and genomic fragments of the target site and the off-target sites were amplified by using specific primers. Mutation rates of the three sites were analyzed by using second-generation sequencing technology.

The experiment result is shown in FIG. 5:

When sgRNAs were used, compared with WTSpCas9, eSpCas9(1.0), eSpCas9(1.1) and SpCas9-HF1 have extremely low off-target effect, but have significantly lower editing efficiencies.

When tRNA-sgRNAs were used, the editing efficiency of each group was increased, however, eSpCas9(1.0), eSpCas9(1.1) and SpCas9-HF1 can maintain relatively high specificity. Particularly for SpCas9-HF1, only extremely low-level mutation can be detected for both two off-target sites. Therefore, the combination of tRNA-sgRNA and SpCas9-HF1 is particularly suitable for genome editing with high efficiency and high specificity.

3.2 Rice OsCDKB2 Target Site

A target site AGGTCGGGGAGGGGACGTACGGG (SEQ ID NO: 20) in rice gene OsCDKB2 was selected to design sgRNA. This target site has three possible off-target sites as shown in FIG. 6. A vector for expressing sgRNA or tRNA-sgRNA and vectors for expressing WTSpCas9, eSpCas9(1.0), eSpCas9(1.1) and SpCas9-HF1 were respectively co-transformed into rice protoplasts. Two days after transformation, protoplast DNA was extracted, and genomic fragments of the target site and the off-target sites were amplified by using specific primers. Mutation rates of the four sites were analyzed by deep sequencing.

The experiment results are shown in FIG. 6. The editing efficiencies of eSpCas9(1.0), eSpCas9(1.1) and SpCas9-HF1 to the target sites are effectively increased by using tRNA-sgRNA instead of sgRNA. In particular, the editing efficiency of SpCas9-HF1 can be restored to a wild-type level, and high specificity can be maintained. As this target sequence starts with an A, by which the U3 promoter can precisely initiate transcription, the increased editing efficiency may result from the increased expression level of sgRNA due to the fusion with tRNA.

Example 4: Editing Specificity of Cas9 Variants to Mismatch Between gRNA and Target Sequence When designing sgRNA for a target site GACGTCGGCGAGGAAGGCCTCGG (SEQ ID NO: 23) in rice gene MKK4, mismatches of two adjacent bases were artificially introduced (purine for purine, and pyrimidine for pyrimidine). Edition under the condition that sgRNA cannot completely match with the target site was detected. It is considered as off-target if edition can be detected. The experiments were performed in a way similar to that in Example 3.1.

Figure 7A:
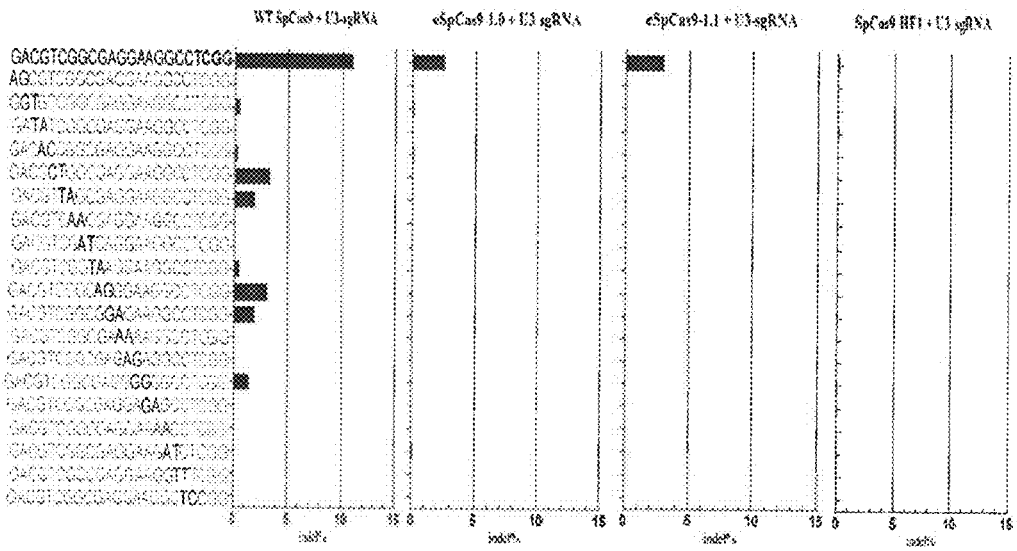
FIGS. 7A and 7B show the editing specificity of Cas9 variant for mismatch between gRNA and target sequence.
Figure 7B:
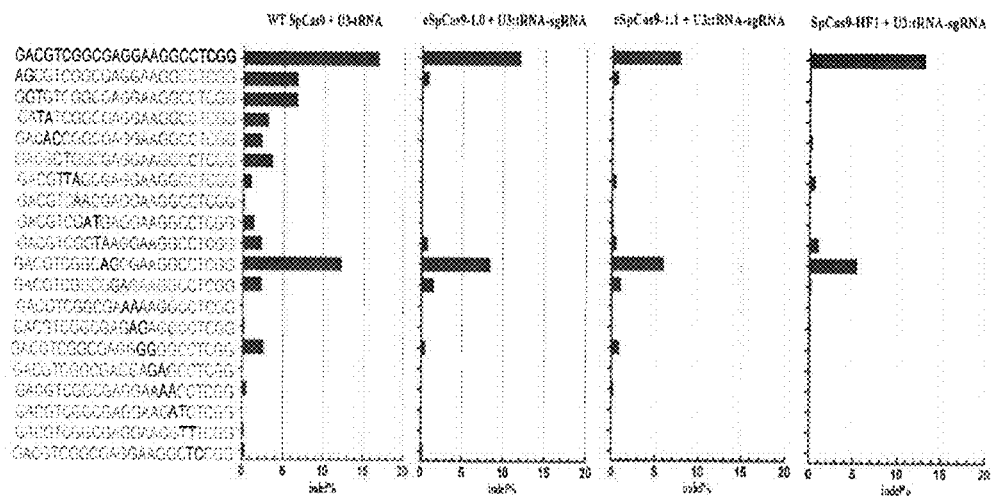

The experiment results were shown in FIG. 7. When tRNA-sgRNA is used, SpCas9 variants showed higher sensitivity to mismatches between gRNA and the target sequence (particularly the mismatch closer to either ends).

Example 5: Editing Efficiency and Specificity of Cas9 Variants in Human Embryonic Kidney 293 Cells sgRNAs were designed against a target sequence GGTGAGTGAGTGTGTGCGTGTGG (SEQ ID NO: 50) within human VEGFA gene. U6:sgRNA-GN$_{19}$ and U6:tRNA-sgRNA-N$_{20}$ represent that the sgRNAs transcribed with U6 promoter are 20 nt in length and completely match the target sequence; U6:sgRNA-GN$_{20}$ represents that the sgRNA transcribed with U6 promoter is 21 nt in length and contains an additional G at 5' end.

Figure 8:
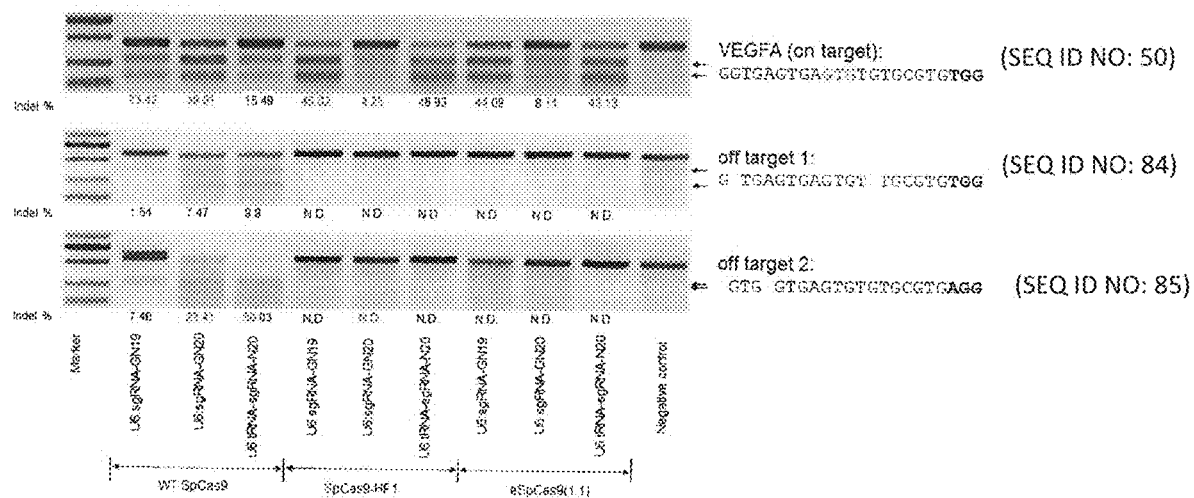
FIG. 8 shows tRNA-sgRNA improved the editing efficiency of eSpCas9(1.1) and SpCas9-HF1 to that of wild-type SpCas9 in human cells.

The T7E1 assay results show (FIG. 8) that WT Cas9 exhibits similar editing efficiency when sgRNA transcribed with different strategies were used. However, the editing efficiency of eSpCas9(1.1) and SpCas9-HF1 were significantly reduced when the sgRNA contains an additional nucleotide at 5' end. And by using tRNA-sgRNA fusions, the editing efficiency of eSpCas9(1.1) and SpCas9-HF1 were increased to that of WT Cas9 or even higher.

With respect to editing specificity, WT Cas9 resulted in off-target editing in both sites off target1 and off target2. eSpCas9(1.1) and SpCas9-HF1 did not result in off-target editing when tRNA-sgRNA fusions were used.

TABLE 4

Target gene and oligonucleotide sequences for construction of sgRNA expression vectors

| sgRNA | Target sequence | Oligo-F | Oligo-R |
|---|---|---|---|
| VEGFA-GN19 | GGTGAGTG AGTGTGT GCGTGTGG (SEQ ID NO: 50) | CACCGGTG AGTGAGTG TGTGCGTG (SEQ ID NO: 51) | AAACCACG CACACACTC ACTCACC (SEQ ID NO: 52) |
| VEGFA-GN20 | GGTGAGTG AGTGTGT GCGTGTGG (SEQ ID NO: 50) | CACCGGGTG AGTGAGT GTGTGCGTG (SEQ ID NO: 53) | AAACCACGC ACACACTC ACTCACCC (SEQ ID NO: 54) |
| VEGFA-tRNA-N20 | GGTGAGTG AGTGTGT GCGTGTGG (SEQ ID NO: 50) | CACCGaaca aagcaccag tggtctagt ggtagaata gtaccctgc cacggtaca gacccgggt tcgattccc ggctggtgc aGGTGAGTG AGTGTGTGC GTG (SEQ ID NO: 55) | AAACCACG CACACACT CACTCACC tgcaccag ccgggaat cgaacccg ggtctgta ccgtggca gggtacta ttctacca ctagacca ctggtgct ttgttC (SEQ ID NO: 56) |

```
Sequence listing
tRNA encoding sequence
                                    SEQ ID NO: 1
aacaaagcaccagtggtctagtggtagaatagtaccctgc cacggtacagacccgggttcgattcccggctggtgca SpCas9 nucleotide sequence
                                    SEQ ID NO: 2
atggcccctaagaagaagagaaaggtcggtattcacggcg ttcctgcggcgatggacaagaagtatagtattggtctgga cattgggacgaattccgttggctgggccgtgatcaccgat gagtacaaggtcccttccaagaagtttaaggttctgggga acaccgatcggcacagcatcaagaagaatctcattggagc cctcctgttcgactcaggcgagaccgccgaagcaacaagg ctcaagagaaccgcaaggagacggtatacaagaaggaaga ataggatctgctacctgcaggagattttcagcaacgaaat ggcgaaggtggacgattcgttctttcatagattggaggag agtttcctcgtcgaggaagataagaagcacgagaggcatc
```

-continued

```
ctatctttggcaacattgtcgacgaggttgcctatcacga
aaagtaccccacaatctatcatctgcggaagaagcttgtg
gactcgactgataaggcggaccttagattgatctacctcg
ctctggcacacatgattaagttcaggggccattttctgat
cgaggggatcttaacccggacaatagcgatgtggacaag
ttgttcatccagctcgtccaaacctacaatcagctctttg
aggaaaacccaattaatgcttcaggcgtcgacgccaaggc
gatcctgtctgcacgcctttcaaagtctcgccggcttgag
aacttgatcgctcaactcccgggcgaaaagaagaacggct
tgttcgggaatctcattgcactttcgttggggctcacacc
aaacttcaagagtaattttgatctcgctgaggacgcaaag
ctgcagctttccaaggacacttatgacgatgacctggata
accttttggcccaaatcggcgatcagtacgcggacttgtt
cctcgccgcgaagaatttgtcggacgcgatcctcctgagt
gatattctccgcgtgaacaccgagattacaaaggccccgc
tctcggcgagtatgatcaagcgctatgacgagcaccatca
ggatctgacccttttgaaggctttggtccggcagcaactc
ccagagaagtacaaggaaatcttctttgatcaatccaaga
acggctacgctggttatattgacggcggggcatcgcagga
ggaattctacaagtttatcaagccaattctggagaagatg
gatggcacagaggaactcctggtgaagctcaatagggagg
accttttgcggaagcaaagaactttcgataacggcagcat
ccctcaccagattcatctcggggagctgcacgccatcctg
agaaggcaggaagacttctaccccttcttaaggataacc
gggagaagatcgaaaagattctgacgttcagaattccgta
ctatgtcggaccactcgcccggggtaattccagatttgcg
tggatgaccagaaagagcgaggaaaccatcacaccttgga
acttcgaggaagtggtcgataagggcgcttccgcacagag
cttcattgagcgcatgacaaattttgacaagaacctgcct
aatgagaaggtccttcccaagcattcctcctgtacgagt
atttcactgtttataacgaactcacgaaggtgaagtatgt
gaccgagggaatgcgcaagcccgccttcctgagcggcgag
caaaagaaggcgatcgtggaccttttgtttaagaccaatc
ggaaggtcacagttaagcagctcaaggaggactacttcaa
gaagattgaatgcttcgattccgttgagatcagcggcgtg
gaagacaggtttaacgcgtcactggggacttaccacgatc
tcctgaagatcattaaggataaggacttcttggacaacga
ggaaaatgaggatatcctcgaagacattgtcctgactctt
acgttgtttgaggataggaaatgatcgaggaacgcttga
agacgtatgccccatctcttcgatgacaaggttatgaagca
gctcaagagaagaagatacaccggatggggaaggctgtcc
```

```
cgcaagcttatcaatggcattagagacaagcaatcaggga
agacaatccttgacttttttgaagtctgatggcttcgcgaa
caggaattttatgcagctgattcacgatgactcacttact
ttcaaggaggatatccgaaaggctcaagtgtcgggacaag
gtgacagtctgcacgagcatatcgccaaccttgcgggatc
tcctgcaatcaagaagggtattctgcagacagtcaaggtt
gtggatgagcttgtgaaggtcatgggacggcataagcccg
agaacatcgttattgagatggccagagaaaatcagaccac
acaaaagggtcagaagaactcgagggagcgcatgaagcgc
atcgaggaaggcattaaggagctggggagtcagatcctta
aggagcacccggtggaaaacacgcagttgcaaaatgagaa
gctctatctgtactatctgcaaaatggcagggatatgtat
gtggaccaggagttggatattaaccgcctctcggattacg
acgtcgatcatatcgttcctcagtccttccttaaggatga
cagcattgacaataaggttctccaccaggtccgacaagaac
cgcggaagtccgataatgtgcccagcgaggaagtcgtta
agaagatgaagaactactggaggcaacttttgaatgccaa
gttgatcacacagaggaagtttgataacctcactaaggcc
gagcgcggaggtctcagcgaactggacaaggcgggcttca
ttaagcggcaactggttgagactagacagatcacgaagca
cgtggcgcagattctcgattcacgcatgaacacgaagtac
gatgagaatgacaagctgatccgggaagtgaaggtcatca
ccttgaagtcaaagctcgtttctgacttcaggaaggattt
ccaattttataaggtgcgcgagatcaacaattatcaccat
gctcatgacgcatacctcaacgctgtggtcggaacagcat
tgattaagaagtacccgaagctcgagtccgaattcgtgta
cggtgactataaggtttacgatgtgcgcaagatgatcgcc
aagtcagagcaggaaattggcaaggccactgcgaagtatt
tcttttactctaacattatgaatttcttaagactgagat
cacgctggctaatggcgaaatccggaagagaccacttatt
gagaccaacggcgagacaggggaaatcgtgtgggacaagg
ggagggatttcgccacagtccgcaaggttctctctatgcc
tcaagtgaatattgtcaagaagactgaagtccagacgggc
gggttctcaaaggaatctattctgcccaagcggaactcgg
ataagcttatcgccagaaagaaggactgggaccccgaagaa
gtatggaggtttcgactcaccaacggtggcttactctgtc
ctggttgtggcaaaggtggagaagggaaagtcaaagaagc
tcaagtctgtcaaggagctcctgggtatcaccattatgga
gaggtccagcttcgaaaagaatccgatcgattttctcgag
gcgaagggatataaggaagtgaagaaggacctgatcatta
```

-continued

```
agcttccaaagtacagtctttctcgagttggaaaacggcag
gaagcgcatgttggcttccgcaggagagctccagaagggt
aacgagcttgctttgccgtccaagtatgtgaacttcctct
atctggcatcccactacgagaagctcaagggcagcccaga
ggataacgaacagaagcaactgtttgtggagcaacacaag
cattatcttgacgagatcattgaacagatttcggagttca
gtaagcgcgtcatcctcgccgacgcgaatttggataaggt
tctctcagcctacaacaagcacccgggacaagcctatcaga
gagcaggcggaaaatatcattcatctcttcaccctgacaa
accttggggctcccgctgcattcaagtattttgacactac
gattgatcggaagagatacacttctacgaaggaggtgctg
gatgcaacccttatccaccaatcgattactggcctctacg
agacgcggatcgacttgagtcagctcggggggggataagag
accagcggcaaccaagaaggcaggacaagcgaagaagaag
aagtag
```

SpCas9 amino acid sequence
                              SEQ ID NO: 3
```
MAPKKKRKVGIHGVPAAMDKKYSIGLDIGTNSVGWAVITD
EYKVPSKKFKVLGNTDRHSIKKNLIGALLFDSGETAEATR
LKRTARRRYTRRKNRICYLQEIFSNEMAKVDDSFFHRLEE
SFLVEEDKKHERHPIFGNIVDEVAYHEKYPTIYHLRKKLV
DSTDKADLRLIYLALAHMIKFRGHFLIEGDLNPDNSDVDK
LFIQLVQTYNQLFEENPINASGVDAKAILSARLSKSRRLE
NLIAQLPGEKKNGLFGNLIALSLGLTPNFKSNFDLAEDAK
LQLSKDTYDDDLDNLLAQIGDQYADLFLAAKNLSDAILLS
DILRVNTEITKAPLSASMIKRYDEHHQDLTLLKALVRQQL
PEKYKEIFFDQSKNGYAGYIDGGASQEEFYKFIKPILEKM
DGTEELLVKLNREDLLRKQRTFDNGSIPHQIHLGELHAIL
RRQEDFYPFLKDNREKIEKILTFRIPYYVGPLARGNSRFA
WMTRKSEETITPWNFEEVVDKGASAQSFIERMTNFDKNLP
NEKVLPKHSLLYEYFTVYNELTKVKYVTEGMRKPAFLSGE
QKKAIVDLLFKTNRKVTVKQLKEDYFKKIECFDSVEISGV
EDRFNASLGTYHDLLKIIKDKDFLDNEENEDILEDIVLTL
TLFEDREMIEERLKTYAHLFDDKVMKQLKRRRYTGWGRLS
RKLINGIRDKQSGKTILDFLKSDGFANRNFMQLIHDDSLT
FKEDIQKAQVSGQGDSLHEHIANLAGSPAIKKGILQTVKV
VDELVKVMGRHKPENIVIEMARENQTTQKGQKNSRERMKR
IEEGIKELGSQILKEHPVENTQLQNEKLYLYYLQNGRDMY
VDQELDINRLSDYDVDHIVPQSFLKDDSIDNKVLTRSDKN
RGKSDNVPSEEVVKKMKNYWRQLLNAKLITQRKFDNLTKA
ERGGLSELDKAGFIKRQLVETRQITKHVAQILDSRMNTKY
DENDKLIREVKVITLKSKLVSDFRKDFQFYKVREINNYHH
AHDAYLNAVVGTALIKKYPKLESEFVYGDYKVYDVRKMIA
KSEQEIGKATAKYFFYSNIMNFFKTEITLANGEIRKRPLI
ETNGETGEIVWDKGRDFATVRKVLSMPQVNIVKKTEVQTG
GFSKESILPKRNSDKLIARKKDWDPKKYGGFDSPTVAYSV
LVVAKVEKGKSKKLKSVKELLGITIMERSSFEKNPIDFLE
AKGYKEVKKDLIIKLPKYSLFELENGRKRMLASAGELQKG
NELALPSKYVNFLYLASHYEKLKGSPEDNEQKQLFVEQHK
HYLDEIIEQISEFSKRVILADANLDKVLSAYNKHRDKPIR
EQAENIIHLFTLTNLGAPAAFKYFDTTIDRKRYTSTKEVL
DATLIHQSITGLYETRIDLSQLGGDKRPAATKKAGQAKKK
K
``` eSpCas9(1.0) amino acid sequence
                              SEQ ID NO: 4
```
MAPKKKRKVGIHGVPAAMDKKYSIGLDIGTNSVGWAVITD
EYKVPSKKFKVLGNTDRHSIKKNLIGALLFDSGETAEATR
LKRTARRRYTRRKNRICYLQEIFSNEMAKVDDSFFHRLEE
SFLVEEDKKHERHPIFGNIVDEVAYHEKYPTIYHLRKKLV
DSTDKADLRLIYLALAHMIKFRGHFLIEGDLNPDNSDVDK
LFIQLVQTYNQLFEENPINASGVDAKAILSARLSKSRRLE
NLIAQLPGEKKNGLFGNLIALSLGLTPNFKSNFDLAEDAK
LQLSKDTYDDDLDNLLAQIGDQYADLFLAAKNLSDAILLS
DILRVNTEITKAPLSASMIKRYDEHHQDLTLLKALVRQQL
PEKYKEIFFDQSKNGYAGYIDGGASQEEFYKFIKPILEKM
DGTEELLVKLNREDLLRKQRTFDNGSIPHQIHLGELHAIL
RRQEDFYPFLKDNREKIEKILTFRIPYYVGPLARGNSRFA
WMTRKSEETITPWNFEEVVDKGASAQSFIERMTNFDKNLP
NEKVLPKHSLLYEYFTVYNELTKVKYVTEGMRKPAFLSGE
QKKAIVDLLFKTNRKVTVKQLKEDYFKKIECFDSVEISGV
EDRFNASLGTYHDLLKIIKDKDFLDNEENEDILEDIVLTL
TLFEDREMIEERLKTYAHLFDDKVMKQLKRRRYTGWGRLS
RKLINGIRDKQSGKTILDFLKSDGFANRNFMQLIHDDSLT
FKEDIQKAQVSGQGDSLHEHIANLAGSPAIKKGILQTVKV
VDELVKVMGRHKPENIVIEMARENQTTQKGQKNSRERMKR
IEEGIKELGSQILKEHPVENTQLQNEALYLYYLQNGRDMY
VDQELDINRLSDYDVDHIVPQSFLKDDSIDNKVLTRSDKN
RGKSDNVPSEEVVKKMKNYWRQLLNAKLITQRKFDNLTKA
ERGGLSELDKAGFIKRQLVETRQITKHVAQILDSRMNTKY
DENDKLIREVKVITLKSKLVSDFRKDFQFYKVREINNYHH
AHDAYLNAVVGTALIKKYPALESEFVYGDYKVYDVRKMIA
KSEQEIGKATAKYFFYSNIMNFFKTEITLANGEIRKAPLI
ETNGETGEIVWDKGRDFATVRKVLSMPQVNIVKKTEVQTG
```

-continued

GFSKESILPKRNSDKLIARKKDWDPKKYGGFDSPTVAYSV

LVVAKVEKGKSKKLKSVKELLGITIMERSSFEKNPIDFLE

AKGYKEVKKDLIIKLPKYSLFELENGRKRMLASAGELQKG

NELALPSKYVNFLYLASHYEKLKGSPEDNEQKOLFVEQHK

HYLDEIIEQISEFSKRVILADANLDKVLSAYNKHRDKPIR

EQAENIIHLFTLTNLGAPAAFKYFDTTIDRKRYTSTKEVL

DATLIHQSITGLYETRIDLSQLGGDKRPAATKKAGQAKKK

K eSpCas9(1.1) amino acid sequence
SEQ ID NO: 5

MAPKKKRKVGIHGVPAAMDKKYSIGLDIGTNSVGWAVITD

EYKVPSKKFKVLGNTDRHSIKKNLIGALLFDSGETAEATR

LKRTARRRYTRRKNRICYLQEIFSNEMAKVDDSFFHRLEE

SFLVEEDKKHERHPIFGNIVDEVAYHEKYPTIYHLRKKLV

DSTDKADLRLIYLALAHMIKFRGHFLIEGDLNPDNSDVDK

LFIQLVQTYNQLFEENPINASGVDAKAILSARLSKSRRLE

NLIAQLPGEKKNGLFGNLIALSLGLTPNFKSNFDLAEDAK

LQLSKDTYDDDLDNLLAQIGDQYADLFLAAKNLSDAILLS

DILRVNTEITKAPLSASMIKRYDEHHQDLTLLKALVRQQL

PEKYKEIFFDQSKNGYAGYIDGGASQEEFYKFIKPILEKM

DGTEELLVKLNREDLLRKQRTFDNGSIPHQIHLGELHAIL

RRQEDFYPFLKDNREKIEKILTFRIPYYVGPLARGNSRFA

WMTRKSEETITPWNFEEVVDKGASAQSFIERMTNFDKNLP

NEKVLPKHSLLYEYFTVYNELTKVKYVTEGMRKPAFLSGE

QKKAIVDLLFKTNRKVTVKQLKEDYFKKIECFDSVEISGV

EDRFNASLGTYHDLLKIIKDKDFLDNEENEDILEDIVLTL

TLFEDREMIEERLKTYAHLFDDKVMKQLKRRRYTGWGRLS

RKLINGIRDKQSGKTILDFLKSDGFANRNFMQLIHDDSLT

FKEDIQKAQVSGQGDSLHEHIANLAGSPAIKKGILQTVKV

VDELVKVMGRHKPENIVIEMARENQTTQKGQKNSRERMKR

IEEGIKELGSQILKEHPVENTQLQNEKLYLYYLQNGRDMY

VDQELDINRLSDYDVDHIVPQSFLADDSIDNKVLTRSDKN

RGKSDNVPSEEVVKKMKNYWRQLLNAKLITQRKFDNLTKA

ERGGLSELDKAGFIKRQLVETRQITKHVAQILDSRMNTKY

DENDKLIREVKVITLKSKLVSDFRKDFQFYKVREINNYHH

AHDAYLNAVVGTALIKKYPALESEFVYGDYKVYDVRKMIA

KSEQEIGKATAKYFFYSNIMNFFKTEITLANGEIRKAPLI

ETNGETGEIVWDKGRDFATVRKVLSMPQVNIVKKTEVQTG

GFSKESILPKRNSDKLIARKKDWDPKKYGGFDSPTVAYSV

LVVAKVEKGKSKKLKSVKELLGITIMERSSFEKNPIDFLE

AKGYKEVKKDLIIKLPKYSLFELENGRKRMLASAGELQKG

NELALPSKYVNFLYLASHYEKLKGSPEDNEQKOLFVEQHK

HYLDEIIEQISEFSKRVILADANLDKVLSAYNKHRDKPIR

EQAENIIHLFTLTNLGAPAAFKYFDTTIDRKRYTSTKEVL

DATLIHQSITGLYETRIDLSQLGGDKRPAATKKAGQAKKK

K

SpCas9-HF1 amino acid sequence
SEQ ID NO: 6

MAPKKKRKVGIHGVPAAMDKKYSIGLDIGTNSVGWAVITD

EYKVPSKKFKVLGNTDRHSIKKNLIGALLFDSGETAEATR

LKRTARRRYTRRKNRICYLQEIFSNEMAKVDDSFFHRLEE

SFLVEEDKKHERHPIFGNIVDEVAYHEKYPTIYHLRKKLV

DSTDKADLRLIYLALAHMIKFRGHFLIEGDLNPDNSDVDK

LFIQLVQTYNQLFEENPINASGVDAKAILSARLSKSRRLE

NLIAQLPGEKKNGLFGNLIALSLGLTPNFKSNFDLAEDAK

LQLSKDTYDDDLDNLLAQIGDQYADLFLAAKNLSDAILLS

DILRVNTEITKAPLSASMIKRYDEHHQDLTLLKALVRQQL

PEKYKEIFFDQSKNGYAGYIDGGASQEEFYKFIKPILEKM

DGTEELLVKLNREDLLRKQRTFDNGSIPHQIHLGELHAIL

RRQEDFYPFLKDNREKIEKILTFRIPYYVGPLARGNSRFA

WMTRKSEETITPWNFEEVVDKGASAQSFIERMTAFDKNLP

NEKVLPKHSLLYEYFTVYNELTKVKYVTEGMRKPAFLSGE

QKKAIVDLLFKTNRKVTVKQLKEDYFKKIECFDSVEISGV

EDRFNASLGTYHDLLKIIKDKDFLDNEENEDILEDIVLTL

TLFEDREMIEERLKTYAHLFDDKVMKQLKRRRYTGWGALS

RKLINGIRDKQSGKTILDFLKSDGFANRNFMALIHDDSLT

FKEDIQKAQVSGQGDSLHEHIANLAGSPAIKKGILQTVKV

VDELVKVMGRHKPENIVIEMARENQTTQKGQKNSRERMKR

IEEGIKELGSQILKEHPVENTQLQNEKLYLYYLQNGRDMY

VDQELDINRLSDYDVDHIVPQSFLKDDSIDNKVLTRSDKN

RGKSDNVPSEEVVKKMKNYWRQLLNAKLITQRKFDNLTKA

ERGGLSELDKAGFIKRQLVETRAITKHVAQILDSRMNTKY

DENDKLIREVKVITLKSKLVSDFRKDFQFYKVREINNYHH

AHDAYLNAVVGTALIKKYPKLESEFVYGDYKVYDVRKMIA

KSEQEIGKATAKYFFYSNIMNFFKTEITLANGEIRKRPLI

ETNGETGEIVWDKGRDFATVRKVLSMPQVNIVKKTEVQTG

GFSKESILPKRNSDKLIARKKDWDPKKYGGFDSPTVAYSV

LVVAKVEKGKSKKLKSVKELLGITIMERSSFEKNPIDFLE

AKGYKEVKKDLIIKLPKYSLFELENGRKRMLASAGELQKG

NELALPSKYVNFLYLASHYEKLKGSPEDNEQKOLFVEQHK

HYLDEIIEQISEFSKRVILADANLDKVLSAYNKHRDKPIR

EQAENIIHLFTLTNLGAPAAFKYFDTTIDRKRYTSTKEVL

DATLIHQSITGLYETRIDLSQLGGDKRPAATKKAGQAKKK

K eSpCas9(1.0) codon-optimized
nucleotide sequence
                         SEQ ID NO: 7
atggcccctaagaagaagagaaaggtcggtattcacggcg ttcctgcggcgatggacaagaagtatagtattggtctgga cattgggacgaattccgttggctgggccgtgatcaccgat gagtacaaggtccctttccaagaagtttaaggttctggga acaccgatcggcacagcatcaagaagaatctcattggagc cctcctgttcgactcaggcgagaccgccgaagcaacaagg ctcaagagaaccgcaaggagacggtatacaagaaggaaga ataggatctgctacctgcaggagattttcagcaacgaaat ggcgaaggtggacgattcgttctttcatagattggaggag agtttcctcgtcgaggaagataagaagcacgagaggcatc ctatctttggcaacattgtcgacgaggttgcctatacga aaagtaccccacaatctatcatctgcggaagaagcttgtg gactcgactgataaggcggaccttagattgatctacctcg ctctggcacacatgattaagttcaggggccattttctgat cgagggggatcttaacccggacaatagcgatgtggacaag ttgttcatccagctcgtccaaacctacaatcagctctttg aggaaaacccaattaatgcttcaggcgtcgacgccaaggc gatcctgtctgcacgcctttcaaagtctcgccggcttgag aacttgatcgctcaactcccgggcgaaaagaagaacggct tgttcgggaatctcattgcactttcgttggggctcacacc aaacttcaagagtaattttgatctcgctgaggacgcaaag ctgcagctttccaaggacacttatgacgatgacctggata accttttggcccaaatcggcgatcagtacgcggacttgtt cctcgccgcgaagaatttgtcggacgcgatcctcctgagt gatattctccgcgtgaacaccgagattacaaaggccccgc tctcggcgagtatgatcaagcgctatgacgagcaccatca ggatctgacccttttgaaggctttggtccggcagcaactc ccagagaagtacaaggaaatcttctttgatcaatccaaga acggctacgctggttatattgacggcggggcatcgcagga ggaattctacaagtttatcaagccaattctggagaagatg gatggcacagaggaactcctggtgaagctcaatagggagg accttttgcggaagcaaagaactttcgataacggcagcat ccctcaccagattcatctcggggagctgcacgccatcctg agaaggcaggaagacttctaccccttcttaaggataacc gggagaagatcgaaaagattctgacgttcagaattccgta ctatgtcggaccactcgcccggggtaattccagatttgcg tggatgaccagaaagagcgaggaaaccatcacaccttgga acttcgaggaagtggtcgataagggcgcttccgcacagag cttcattgagcgcatgacaaattttgacaagaacctgcct aatgagaaggtccttcccaagcattccctcctgtacgagt atttcactgtttataacgaactcacgaaggtgaagtatgt gaccgagggaatgcgcaagcccgccttcctgagcggcgag caaaagaaggcgatcgtggaccttttgtttaagaccaatc ggaaggtcacagttaagcagctcaaggaggactacttcaa gaagattgaatgcttcgattccgttgagatcagcggcgtg gaagacaggtttaacgcgtcactggggacttaccacgatc tcctgaagatcattaaggataaggacttcttggacaacga ggaaaatgaggatatcctcgaagacattgtcctgactctt acgttgtttgaggataggaaatgatcgaggaacgcttga gacgtatgcccatctcttcgatgacaaggttatgaagca gctcaagagaagaagatacaccggatggggaaggctgtcc cgcaagcttatcaatggcattagagacaagcaatcaggga agacaatccttgacttttgaagtctgatggcttcgcgaa caggaattttatgcagctgattcacgatgactcacttact ttcaaggaggatatccgaaggctcaagtgtcgggacaag gtgacagtctgcacgagcatatcgccaaccttgcgggatc tcctgcaatcaagaagggtattctgcagacagtcaaggtt gtggatgagcttgtgaaggtcatgggacggcataagcccg agaacatcgttattgagatggccagagaaaatcagaccac acaaaagggtcagaagaactcgagggagcgcatgaagcgc atcgaggaaggcattaaggagctggggagtcagatcctta aggagcacccggtggaaaacacgcagttgcaaaatgaggc cctctatctgtactatctgcaaaatggcagggatatgtat gtggaccaggagttggatattaaccgcctctcggattacg acgtcgatcatatcgttcctcagtccttccttaaggatga cagcattgacaataaggttctcaccaggtccgacaagaac cgcggaagtccgataatgtgcccagcgaggaagtcgtta agaagatgaagaactactggaggcaacttttgaatgccaa gttgatcacacagaggaagtttgataacctcactaaggcc gagcgcggaggtctcagcgaactggacaaggcgggcttca ttaagcggcaactggttgagactagacagatcacgaagca cgtggcgcagattctcgattcacgcatgaacacgaagtac gatgagaatgacaagctgatccgggaagtgaaggtcatca ccttgaagtcaaagctcgtttctgacttcaggaaggattt ccaattttataaggtgcgcgagatcaacaattataccat gctcatgacgcatacctcaacgctgtggtcggaacagcat tgattaagaagtacccggcgctcgagtccgaattcgtgta cggtgactataaggtttacgatgtgcgcaagatgatcgcc aagtcagagcaggaaattggcaaggccactgcgaagtatt tcttttactctaacattatgaatttctttaagactgagat cacgctggctaatggcgaaatccggaaggcgccacttatt gagaccaacggcgagacaggggaaatcgtgtgggacaagg ggagggatttcgccacagtccgcaaggttctctctatgcc tcaagtgaatattgtcaagaagactgaagtccagacgggg ggttctcaaaggaatctattctgcccaagcggaactcgga taagcttatcgccagaaagaaggactgggacccgaagaag tatggaggtttcgactcaccaacggtggcttactctgtcc tggttgtggcaaaggtggagaagggaaagtcaaagaagct caagtctgtcaaggagctcctgggtatcaccattatggag aggtccagcttcgaaaagaatccgatcgattttctcgagg cgaaggatataaggaagtgaagaaggacctgatcattaa gcttccaaagtacagtcttttcgagttggaaaacggcagg aagcgcatgttggcttccgcaggagagctccagaagggta acgagcttgctttgccgtccaagtatgtgaacttcctcta tctggcatcccactacgaagctcaagggcagcccagag gataacgaacagaagcaactgtttgtggagcaacacaagc attatcttgacgagatcattgaacagatttcggagttcag taagcgcgtcatcctcgccgacgcgaatttggataaggtt ctctcagcctacaacaagcaccgggacaagcctatcagag agcaggcggaaaatatcattcatctcttcaccctgacaaa ccttggggctcccgctgcattcaagtattttgacactacg attgatcggaagagatacacttctacgaaggaggtgctgg atgcaaccctatccaccaatcgattactggcctctacga gacgcggatcgacttgagtcagctcgggggggataagaga ccagcggcaaccaagaaggcaggacaagcgaagaagaaga agtag eSpCas9(1.1) codon-optimized nucleotide sequence

SEQ ID NO: 8 atggcccctaagaagaagagaaaggtcggtattcacggcg ttcctgcggcgatggacaagaagtatagtattggtctgga cattgggacgaattccgttggctgggccgtgatcaccgat gagtacaaggtccccttccaagaagtttaaggttctggga acaccgatcggcacagcatcaagaagaatctcattggagc cctcctgttcgactcaggcgagaccgccgaagcaacaagg ctcaagagaaccgcaaggagacggtatacaagaaggaaga ataggatctgctacctgcaggagattttcagcaacgaaat ggcgaaggtggacgattcgttctttcatagattggaggag agtttcctcgtcgaggaagataagaagcacgagaggcatc ctatctttggcaacattgtcgacgaggttgcctatcacga aaagtaccccacaatctatcatctgcggaagaagcttgtg gactcgactgataaggcggaccttagattgatctacctcg ctctggcacacatgattaagttcaggggccatttcctgat cgaggggatcttaacccggacaatagcgatgtggacaag ttgttcatccagctcgtccaaacctacaatcagctctttg aggaaaacccaattaatgcttcaggcgtcgacgccaaggc gatcctgtctgcacgcctttcaaagtctcgccggcttgag aacttgatcgctcaactcccgggcgaaaagaagaacggct tgttcgggaatctcattgcacttcgttggggctcacacc aaacttcaagagtaattttgatctcgctgaggacgcaaag ctgcagctttccaaggacacttatgacgatgacctggata accttttggcccaaatcggcgatcagtacgcggacttgtt cctcgccgcgaagaatttgtcggacgcgatcctcctgagt gatattctccgcgtgaaccaccgagattacaaaggccccgc tctcggcgagtatgatcaagcgctatgacgagcaccatca ggatctgacccttttgaaggctttggtccggcagcaactc ccagagaagtacaaggaaatcttctttgatcaatccaaga acggctacgctggttatattgacggcggggcatcgcagga ggaattctacaagtttatcaagccaattctggagaagatg gatggcacagaggaactcctggtgaagctcaatagggagg accttttgcggaagcaaagaactttcgataacggcagcat ccctcaccagattcatctcggggagctgcacgccatcctg agaaggcaggaagacttctacccctttcttaaggataacc gggagaagatcgaaaagattctgacgttcagaattccgta ctatgtcggaccactcgcccggggtaattccagatttgcg tggatgaccagaaagagcgaggaaaccatcacaccttgga acttcgaggaagtggtcgataagggcgcttccgcacagag cttcattgagcgcatgacaaattttgacaagaacctgcct aatgagaaggtccttcccaagcattccctcctgtacgagt atttcactgtttataacgaactcacgaaggtgaagtatgt gaccgagggaatgcgcaagcccgccttcctgagcggcgag caaaagaaggcgatcgtggaccttgttaagaccaatc ggaaggtcacagttaagcagctcaaggaggactacttcaa gaagattgaatgcttcgattccgttgagatcagcggcgtg gaagacaggtttaacgcgtcactggggacttaccacgatc tcctgaagatcattaaggataaggacttcttggacaacga ggaaaatgaggatatcctcgaagacattgtcctgactctt acgttgtttgaggataggaaatgatcgaggaacgcttga agacgtatgcccatctcttcgatgacaaggttatgaagca gctcaagagaagaagatacaccggatggggaaggctgtcc cgcaagcttatcaatggcattagagacaagcaatcaggga

```
agacaatccttgacttttgaagtctgatggcttcgcgaa
caggaattttatgcagctgattcacgatgactcacttact
ttcaaggaggatatccagaaggctcaagtgtcgggacaag
gtgacagtctgcacgagcatatcgccaaccttgcgggatc
tcctgcaatcaagaagggtattctgcagacagtcaaggtt
gtggatgagcttgtgaaggtcatgggacggcataagcccg
agaacatcgttattgagatggccagagaaaatcagaccac
acaaaagggtcagaagaactcgagggagcgcatgaagcgc
atcgaggaaggcattaaggagctggggagtcagatcctta
aggagcacccggtggaaaacacgcagttgcaaaatgagaa
gctctatctgtactatctgcaaaatggcagggatatgtat
gtggaccaggagttggatattaaccgcctctcggattacg
acgtcgatcatatcgttcctcagtccttccttgcggatga
cagcattgacaataaggttctcaccaggtccgacaagaac
cgcgggaagtccgataatgtgcccagcgaggaagtcgtta
agaagatgaagaactactggaggcaacttttgaatgccaa
gttgatcacacagaggaagtttgataacctcactaaggcc
gagcgcggaggtctcagcgaactggacaaggcgggcttca
ttaagcggcaactggttgagactagacagatcacgaagca
cgtggcgcagattctcgattcacgcatgaacacgaagtac
gatgagaatgacaagctgatccgggaagtgaaggtcatca
ccttgaagtcaaagctcgtttctgacttcaggaaggattt
ccaattttataaggtgcgcgagtcaacaattatccaccat
gctcatgacgcatacctcaacgctgtggtcggaacagcat
tgattaagaagtaccggcgctcgagtccgaattcgtgta
cggtgactataaggtttacgatgtgcgcaagatgatcgcc
aagtcagagcaggaaattggcaaggccactgcgaagtatt
tcttttactctaacattatgaatttctttaagactgagat
cacgctggctaatggcgaaatccggaaggcgccacttatt
gagaccaacggcgagacaggggaaatcgtgtgggacaagg
ggagggatttcgccacagtccgcaaggttctctctatgcc
tcaagtgaatattgtcaagaagactgaagtccagacgggc
gggttctcaaaggaatctattctgcccaagcggaactcgg
ataagcttatcgccagaaagaaggactgggacccgaagaa
gtatggaggtttcgactcaccaacggtggcttactctgtc
ctggttgtggcaaaggtggagaagggaaagtcaagaagc
tcaagtctgtcaaggagctcctgggtatcaccattatgga
gaggtccagcttcgaaaagaatccgatcgattttctcgag
gcgaagggatataaggaagtgaagaaggacctgatcatta
agcttccaaagtacagtctttctgagttggaaaacggcag
gaagcgcatgttggcttccgcaggagagctccagaagggt
```

```
aacgagcttgctttgccgtccaagtatgtgaacttcctct
atctggcatcccactacgagaagctcaagggcagcccaga
ggataacgaacagaagcaactgtttgtggagcaacacaag
cattatcttgacgagatcattgaacagatttcggagttca
gtaagcgcgtcatcctcgccgacgcgaatttggataaggt
tctctcagcctacaacaagcacgggacaagcctatcaga
gagcaggcggaaaatatcattcatctcttcaccctgacaa
accttgggctccgctgcattcaagtattttgacactac
gattgatcggaagagatacacttctacgaaggaggtgctg
gatgcaacccttatccaccaatcgattactggcctctacg
agacgcggatcgacttgagtcagctcggggggataagag
accagcggcaaccaagaaggcaggacaagcgaagaagaag
aagtag SpCas9-HF1 codon-optimized nucleotide
sequence
                                    SEQ ID NO: 9
atggcccctaagaagaagagaaaggtcggtattcacggcg
ttcctgcggcgatggacaagaagtatagtattggtctgga
cattgggacgaattccgttggctgggccgtgatcaccgat
gagtacaaggtcccttccaagaagtttaaggttctgggga
acaccgatcggcacagcatcaagaagaatctcattggagc
cctcctgttcgactcaggcgagaccgccgaagcaacaagg
ctcaagagaaccgcaaggagacggtatacaagaaggaaga
ataggatctgctacctgcaggagattttcagcaacgaaat
ggcgaaggtggacgattcgttctttcatagattggaggag
agtttcctcgtcgaggaagataagaagcacgagaggcatc
ctatctttggcaacattgtcgacgaggttgcctatcacga
aaagtaccccacaatctatcatctgcggaagaagcttgtg
gactcgactgataaggcggaccttagattgatctacctcg
ctctggcacacatgattaagttcaggggccatttcctgat
cgaggggatcttaacccggacaatagcgatgtggacaag
ttgttcatccagctcgtccaaacctacaatcagctctttg
aggaaaacccaattaatgcttcaggcgtcgacgccaaggc
gatcctgtctgcacgcctttcaaagtctcgccggcttgag
aacttgatcgctcaactcccgggcgaaaagaagaacggct
tgttcgggaatctcattgcactttcgttggggctcacacc
aaacttcaagagtaattttgatctcgctgaggacgcaaag
ctgcagctttccaaggacacttatgacgatgacctggata
accttttggcccaaatcggcgatcagtacgcggacttgtt
cctcgccgcgaagaatttgtcggacgcgatcctcctgagt
gatattctccgcgtgaacaccgagattacaaaggccccgc
tctcggcgagtatgatcaagcgctatgacgagcaccatca
```

-continued ggatctgacccttttgaaggctttggtccggcagcaactc ccagagaagtacaaggaaatcttctttgatcaatccaaga acggctacgctggttatattgacggggggcatcgcaggag gaattctcaagtttatcaagccaattctggagaagatgg atggcacagaggaactcctggtgaagctcaatagggagga ccttttgcggaagcaaagaactttcgataacggcagcatc cctcaccagattcatctcggggagctgcacgccatcctga gaaggcaggaagacttctacccctttcttaaggataaccg ggagaagatcgaaaagattctgacgttcagaattccgtac tatgtcggaccactcgcccggggtaattccagatttgcgt ggatgaccagaaagagcgaggaaaccatcacaccttggaa cttcgaggaagtggtcgataagggcgcttccgcacagagc ttcattgagcgcatgacaGCCtttgacaagaacctgccta atgagaaggtccttcccaagcattccctcctgtacgagta tttcactgtttataacgaactcacgaaggtgaagtatgtg accgagggaatgcgcaagcccgccttcctgagcggcgagc aaaagaaggcgatcgtggaccttttgtttaagaccaatcg gaaggtcacagttaagcagctcaaggaggactacttcaag aagattgaatgcttcgattccgttgagatcagcggcgtgg aagacaggtttaacgcgtcactggggacttaccacgatct cctgaagatcattaaggataaggacttcttggacaacgag gaaaatgaggatatcctcgaagacattgcctgactctta cgttgtttgaggatagggaaatgatcgaggaacgcttgaa gacgtatgcccatctcttcgatgacaaggttatgaagcag ctcaagagaagaagatacaccggatggggaGCCctgtccc gcaagcttatcaatggcattagagacaagcaatcagggaa gacaatccttgacttttttgaagtctgatggcttcgcgaac aggaattttatgGCCctgattcacgatgactcacttactt tcaaggaggatatccagaaggctcaagtgtcgggacaagg tgacagtctgcacgagcatatcgccaaccttgcgggatct cctgcaatcaagaagggtattctgcagacagtcaaggttg tggatgagcttgtgaaggtcatgggacggcataagcccga gaacatcgttattgagatggccagagaaaatcagaccaca caaaagggtcagaagaactcgagggagcgcatgaagcgca tcgaggaaggcattaaggagctggggagtcagatccttaa ggagcacccggtggaaaacacgcagttgcaaaatgagaag ctctatctgtactatctgcaaaatggcagggatatgtatg tggaccaggagttggatattaaccgcctctcggattacga cgtcgatcatatcgttcctcagtccttccttaaggatgac agcattgacaataaggttctcaccaggtccgacaagaacc gcgggaagtccgataatgtgcccagcgaggaagtcgttaa gaagatgaagaactactggaggcaacttttgaatgccaag ttgatcacacagaggaagtttgataacctcactaaggccg agcgcggaggtctcagcgaactggacaagggggcttcatt aagcggcaactggttgagactagaGCCatcacgaagcacg tggcgcagattctcgattcacgcatgaacacgaagtacga tgagaatgacaagctgatccgggaagtgaaggtcatcacc ttgaagtcaaagctcgtttctgacttcaggaaggatttcc aattttataaggtgcgcgagatcaacaattatcaccatgc tcatgacgcatacctcaacgctgtggtcggaacagcattg attaagaagtacccgaagctcgagtccgaattcgtgtacg gtgactataaggtttacgatgtgcgcaagatgatcgccaa gtcagagcaggaaattggcaaggccactgcgaagtatttc ttttactctaacattatgaatttctttaagactgagatca cgctggctaatggcgaaatccggaagagaccacttattga gaccaacggcgagacaggggaaatcgtgtgggacaagggg agggatttcgccacagtccgcaaggttctctctatgcctc aagtgaatattgtcaagaagactgaagtccagacgggcgg gttctcaaaggaatctattctgcccaagcggaactcggat aagcttatcgccagaaagaaggactgggacccgaagaagt atggaggtttcgactcaccaacggtggcttactctgtcct ggttgtggcaaaggtggagaaggaaagtcaaagaagctc aagtctgtcaaggagctcctgggtatcaccattatggaga ggtccagcttcgaaaagaatccgatcgattttctcgaggc gaagggatataaggaagtgaagaaggacctgatcattaag cttccaaagtacagtcttttcgagttggaaaacggcagga agcgcatgttggcttccgcaggagagctccagaagggtaa cgagcttgctttgccgtccaagtatgtgaacttcctctat ctggcatcccactacgagaagctcaagggcagcccagagg ataacgaacagaagcaactgtttgtggagcaacacaagca ttatcttgacgagatcattgaacagatttcggagttcagt aagcgcgtcatcctcgccgacgcgaatttggataaggttc tctcagcctacaacaagcaccgggacaagcctatcagaga gcaggcggaaaatatcattcatctcttcacccctgacaaac cttggggctcccgctgcattcaagtattttgacactacga ttgatcggaagagatacacttctacgaaggaggtgctgga tgcaacccttatccaccaatcgattactggcctctacgag acgcggatcgacttgagtcagctcggggggggataagagac cagcggcaaccaagaaggcaggacaagcgaagaagaagaa gtag pJIT163-SpCas9 vector sequence

SEQ ID NO: 10 gagctcggtacctgacccggtcgtgcccctctctagagat aatgagcattgcatgtctaagttataaaaaattaccacat atttttttttgtcacacttgtttgaagtgcagtttatctat ctttatacatatatttaaactttactctacgaataatata atctatagtactacaataatatcagtgttttagagaatca tataaatgaacagttagacatggtctaaaggacaattgag tattttgacaacaggactctacagttttatcttttagtg tgcatgtgttctcctttttttttgcaaatagcttcaccta tataatacttcatccattttattagtacatccatttaggg tttaggggttaatggttttatagactaattttttttagtac atctattttattctatttagcctctaaattaagaaaact aaaactctatttagttttttttatttaataatttagatat aaaatagaataaaataaagtgactaaaaaattaaacaaata cccctttaagaaattaaaaaaactaaggaaacattttctt gtttcgagtagataatgccagcctgttaaacgccgtcgac gagtctaacggacaccaaccagcgaaccagcagcgtcgcg tcgggccaagcgaagcagacggcacggcatctctgtcgct gcctctggaccctctcgatcgagagttccgctccaccgt tggacttgctccgctgtcggcatccagaaattgcgtggcg gagcggcagacgtgagccggcacggcaggcggcctcctcc tcctctcacggcaccggcagctacggggattccttccc accgctccttcgctttcccttcctcgcccgccgtaataaa tagacaccccctccacaccctctttccccaacctcgtgtt gttcggagcgcacacacacaaccagatctcccccaaat ccaccgtcggcacctccgcttcaaggtacgccgctcgtc ctccccccccccctctctaccttctctagatcggcgtt ccggtccatggttagggcccggtagttctacttctgttca tgtttgtgttagatccgtgtttgtgttagatccgtgctgc tagcgttcgtacacggatgcgacctgtacgtcagacacgt tctgattgctaacttgccagtgtttctcttttggggaatcc tgggatggctctagccgttccgcagacgggatcgatttca tgatttttttttgtttcgttgcatagggttttggtttgccct tttcctttatttcaatatatgccgtgcacttgtttgtcgg gtcatcttttcatgctttttttgtcttggttgtgatgat gtggtctggttgggcggtcgttctagatcggagtagaatt aattctgtttcaaactacctggtggatttattaattttgg atctgtatgtgtgtgccatacatattcatagttacgaatt gaagatgatggatggaaatatcgatctaggataggtatac atgttgatgcgggttttactgatgcatatacagagatgct ttttgttcgcttggttgtgatgatgtggtgtggttgggcg gtcgttcattcgttctagatcggagtagaatactgtttca aactacctggtgtatttattaattttggaactgtatgtgt gtgtcatacatcttcatagttacgagtttaagatggatgg aaatatcgatctaggataggtatacatgttgatgtgggtt ttactgatgcatatacatgatggcatatgcagcatctatt catatgctctaaccttgagtacctatctattataataaac aagtatgttttataattattttgatcttgatatacttgga tgatggcatatgcagcagctatatgtggattttttttagcc ctgccttcatacgctatttatttgcttggtactgtttctt ttgtcgatgctcaccctgttgtttggtgttacttctgcaa agcttccaccatggcgtgcaggtcgactctagaggatccc catggcccctaagaagaagagaaaggtcggtattcacggc gttcctgcggcgatggacaagaagtatagtattggtctgg acattgggacgaattccgttggctgggccgtgatcaccga tgagtacaaggtccttccaagaagtttaaggttctgggg aacaccgatcggcacagcatcaagaagaatctcattggag ccctcctgttcgactcaggcgagaccgccgaagcaacaag gctcaagagaaccgcaaggagacggtatacaagaaggaag aataggatctgctacctgcaggagattttcagcaacgaaa tggcgaaggtggacgattcgttctttcatagattggagga gagtttcctcgtcgaggaagataagaagcacgagaggcat cctatctttggcaacattgtcgacgaggttgcctatcacg aaaagtaccccacaatctatcatctgcggaagaagcttgt ggactcgactgataaggcggaccttagattgatctacctc gctctggcacacatgattaagttcaggggccattttctga tcgaggggatcttaacccggacaatagcgatgtggacaa gttgttcatccagctcgtccaaacctacaatcagctctt gaggaaaacccaattaatgcttcaggcgtcgacgccaagg cgatcctgtctgcacgcctttcaaagtctcgccggcttga gaacttgatcgctcaactcccggcgaaaagaagaacggc ttgttcgggaatctcattgcactttcgttggggctcacac caaacttcaagagtaattttgatctcgctgaggacgcaaa gctgcagctttccaaggacacttatgacgatgacctggat aaccttttggcccaaatcggcgatcagtacgcggacttgt tcctcgccgcgaagaatttgtcggacgcgatcctcctgag tgatattctccgcgtgaacaccgagattacaaaggcccg ctctcggcgagtatgatcaagcgctatgacgagcaccatc -continued aggatctgacccttttgaaggctttggtccggcagcaact
cccagagaagtacaaggaaatcttctttgatcaatccaag
aacggctacgctggttatattgacggcggggcatcgcagg
aggaattctacaagtttatcaagccaattctggagaagat
ggatggcacagaggaactcctggtgaagctcaatagggag
gaccttttgcggaagcaaagaactttcgataacggcagca
tccctcaccagattcatctcggggagctgcacgccatcct
gagaaggcaggaagacttctaccccttttcttaaggataac
cgggagaagatcgaaaagattctgacgttcagaattccgt
actatgtcggaccactcgcccggggtaattccagatttgc
gtggatgaccagaaagagcgaggaaaccatcacaccttgg
aacttcgaggaagtggtcgataagggcgcttccgcacaga
gcttcattgagcgcatgacaaattttgacaagaacctgcc
taatgagaaggtccttcccaagcattccctcctgtacgag
tatttcactgtttataacgaactcacgaaggtgaagtatg
tgaccgagggaatgcgcaagcccgccttcctgagcggcga
gcaaaagaaggcgatcgtggaccttttgtttaagaccaat
cggaaggtcacagttaagcagctcaaggaggactacttca
agaagattgaatgcttcgattccgttgagatcagcggcgt
ggaagacaggtttaacgcgtcactggggacttaccacgat
ctcctgaagatcattaaggataaggacttcttggacaacg
aggaaaatgaggatatcctcgaagacattgtcctgactct
tacgttgtttgaggataggaaatgatcgaggaacgcttg
aagacgtatgcccatctcttcgatgacaaggttatgaagc
agctcaagagaagaagatacaccggatgggaaggctgtc
ccgcaagcttatcaatggcattagagacaagcaatcaggg
aagacaatccttgacttttgaagtctgatggcttcgcga
acaggaattttatgcagctgattcacgatgactcacttac
tttcaaggaggatatccagaaggctcaagtgtcgggacaa
ggtgacagtctgcacgagcatatcgccaaccttgcggat
ctcctgcaatcaagaagggtattctgcagacagtcaaggt
tgtggatgagcttgtgaaggtcatgggacggcataagccc
gagaacatcgttattgagatggccagagaaaatcagacca
cacaaaagggtcagaagaactcgagggagcgcatgaagcg
catcgaggaaggcattaaggagctggggagtcagatcctt
aaggagcacccggtggaaaacacgcagttgcaaaatgaga
agctctatctgtactatctgcaaaatggcagggatatgta
tgtggaccaggagttggatattaaccgcctctcggattac
gacgtcgatcatatcgttcctcagtccttccttaaggatg
acagcattgacaataaggttctcaccaggtccgacaagaa
ccgcgggaagtccgataatgtgcccagcgaggaagtcgtt -continued aagaagatgaagaactactggaggcaacttttgaatgcca
agttgatcacacagaggaagtttgataacctcactaaggc
cgagcgcggaggtctcagcgaactggacaaggcgggcttc
attaagcggcaactggttgagactagacagatcacgaagc
acgtggcgcagattctcgattcacgcatgaacacgaagta
cgatgagaatgacaagctgatccgggaagtgaaggtcatc
accttgaagtcaaagctcgtttctgacttcaggaaggatt
ccaattttataaggtgcgcgagatcaacaattatcacca
tgctcatgacgcatacctcaacgctgtggtcggaacagca
ttgattaagaagtacccgaagctcgagtccgaattcgtgt
acggtgactataaggtttacgatgtgcgcaagatgatcgc
caagtcagagcaggaaattggcaaggccactgcgaagtat
ttcttttactctaacattatgaatttctttaagactgaga
tcacgctggctaatggcgaaatccggaagagaccacttat
tgagaccaacggcgagacaggggaaatcgtgtgggacaag
gggagggatttcgccacagtccgcaaggttctctctatgc
ctcaagtgaatattgtcaagaagactgaagtccagacggg
gggttctcaaaggaatctattctgcccaagcggaactcgg
ataagcttatcgccagaaagaaggactgggacccgaagaa
gtatggaggtttcgactcaccaacggtggcttactctgtc
ctggttgtggcaaaggtggagaagggaaagtcaaagaagc
tcaagtctgtcaaggagctcctgggtataccattatgga
gaggtccagcttcgaaaagaatccgatcgattttctcgag
gcgaagggatataaggaagtgaagaaggacctgatcatta
agcttccaaagtacagtcttttcgagttggaaaacggcag
gaagcgcatgttggcttccgcaggagagctccagaagggt
aacgagcttgctttgccgtccaagtatgtgaacttcctct
atctggcatcccactacgagaagctcaagggcagcccaga
ggataacgaacagaagcaactgtttgtggagcaacacaag
cattatcttgacgagatcattgaacagatttcggagttca
gtaagcgcgtcatcctcgccgacgcgaatttggataaggt
tctctcagcctacaacaagcaccgggacaagcctatcaga
gagcaggcggaaaatatcattcatctcttcaccctgacaa
accttggggctcccgctgcattcaagtattttgacactac
gattgatcggaagagatacacttctacgaaggaggtgctg
gatgcaacccttatccaccaatcgattactggcctctacg
agacgcggatcgacttgagtcagctcgggggggataagag
accagcggcaaccaagaaggcaggacaagcgaagaagaag
aagtaggggcgagctcgaattcgctgaaatcaccagtctc
tctctacaaatctatctctctctattttctccataaataa -continued

```
tgtgtgagtagtttcccgataagggaaattagggttctta
tagggtttcgctcatgtgttgagcatataagaaacccttta
gtatgtatttgtatttgtaaaatacttctatcaataaaat
ttctaattcctaaaaccaaaatccagtactaaaatccaga
tctcctaaagtccctatagatctttgtcgtgaatataaac
cagacacgagacgactaaacctggagcccagacgccgttc
gaagctagaagtaccgcttaggcaggaggccgttagggaa
aagatgctaaggcagggttggttacgttgactccccgta
ggtttggtttaaatatgatgaagtggacggaaggaaggag
gaagacaaggaaggataaggttgcaggccctgtgcaaggt
aagaagatggaaatttgatagaggtacgctactatactta
tactatacgctaagggaatgcttgtatttataccctatac
cccctaataaccccttatcaatttaagaaataatccgcat
aagcccccgcttaaaaattggtatcagagccatgaatagg
tctatgaccaaaactcaagaggataaaacctcaccaaaat
acgaaagagttcttaactctaaagataaaagatctttcaa
gatcaaaactagttccctcacaccggagcatgcgatatcc
tcgagagatctaggcgtaatcatggtcatagctgtttcct
gtgtgaaattgttatccgctcacaattccacacaacatac
gagccggaagcataaagtgtaaagcctggggtgcctaatg
agtgagctaactcacattaattgcgttgcgctcactgccc
gctttccagtcgggaaacctgtcgtgccagctgcattaat
gaatcggccaacgcgcggggagaggcggtttgcgtattgg
gcgctcttccgcttcctcgctcactgactcgctgcgctcg
gtcgttcggctgcggcgagcggtatcagctcactcaaagg
cggtaatacggttatccacagaatcaggggataacgcagg
aaagaacatgtgagcaaaaggccagcaaaaggccaggaac
cgtaaaaaggccgcgttgctggcgtttttccataggctcc
gcccccctgacgagcatcacaaaaatcgacgctcaagtca
gaggtggcgaaacccgacaggactataaagataccaggcg
tttccccctggaagctccctcgtgcgctctcctgttccga
ccctgccgcttaccggatacctgtccgcctttctcccttc
gggaagcgtggcgctttctcaatgctcacgctgtaggtat
ctcagttcggtgtaggtcgttcgctccaagctgggctgtg
tgcacgaaccccccgttcagcccgaccgctgcgccttatc
cggtaactatcgtcttgagtccaacccggtaagacacgac
ttatcgccactggcagcagccactggtaacaggattagca
gagcgaggtatgtaggcggtgctacagagttcttgaagtg
gtggcctaactacggctacactagaaggacagtatttggt
atctgcgctctgctgaagccagttaccttcggaaaagag
ttggtagctcttgatccggcaaacaaaccaccgctggtag
```

-continued

```
cggtggtttttttgtttgcaagcagcagattacgcgcaga
aaaaaaggatctcaagaagatcctttgatcttttctacgg
ggtctgacgctcagtggaacgaaaactcacgttaagggat
tttggtcatgagattatcaaaaaggatcttcacctagatc
cttttaaattaaaaatgaagttttaaatcaatctaaagta
tatatgagtaaacttggtctgacagttaccaatgcttaat
cagtgaggcacctatctcagcgatctgtctatttcgttca
tccatagttgcctgactccccgtcgtgtagataactacga
tacgggagggcttaccatctggccccagtgctgcaatgat
accgcgagacccacgctcaccggctccagatttatcagca
ataaaccagccagccggaagggccgagcgcagaagtggtc
ctgcaactttatccgcctccatccagtctattaattgttg
ccgggaagctagagtaagtagttcgccagttaatagtttg
cgcaacgttgttgccattgctacaggcatcgtggtgtcac
gctcgtcgtttggtatggcttcattcagctccggttccca
acgatcaaggcgagttacatgatcccccatgttgtgcaaa
aaagcggttagctccttcggtcctccgatcgttgtcagaa
gtaagttggccgcagtgttatcactcatggttatggcagc
actgcataattctcttactgtcatgccatccgtaagatgc
ttttctgtgactggtgagtactcaaccaagtcattctgag
aatagtgtatgcggcgaccgagttgctcttgcccggcgtc
aatacgggataataccgcgccacatagcagaactttaaaa
gtgctcatcattggaaaacgttcttcggggcgaaaactct
caaggatcttaccgctgttgagatccagttcgatgtaacc
cactcgtgcacccaactgatcttcagcatcttttactttc
accagcgtttctgggtgagcaaaaacaggaaggcaaaatg
ccgcaaaaaagggaataagggcgacacggaaatgttgaat
actcatactcttcctttttcaatattattgaagcatttat
cagggttattgtctcatgagcggatacatatttgaatgta
tttagaaaaataaacaaataggggttccgcgcacatttcc
ccgaaaagtgccacctgacgt
``` pUC57-U3-tRNA-sgRNA vector sequence

SEQ ID NO: 11

```
tcgcgcgtttcggtgatgacggtgaaaacctctgacacat
gcagctcccggagacggtcacagcttgtctgtaagcggat
gccgggagcagacaagcccgtcagggcgcgtcagcgggtg
ttggcgggtgtcggggctggcttaactatgcggcatcaga
gcagattgtactgagagtgcaccagatgcggtgtgaaata
ccgcacagatgcgtaaggagaaaataccgcatcaggcgcc
attcgccattcaggctgcgcaactgttgggaagggcgatc
ggtgcgggcctcttcgctattacgccagctggcgaaaggg
```

-continued ggatgtgctgcaaggcgattaagttgggtaacgccagggt tttcccagtcacgacgttgtaaaacgacggccagtgcctg caggtcgacgattaaggaatctttaaacatacgaacagat cacttaaagttcttctgaagcaacttaaagttatcaggca tgcatggatcttggaggaatcagatgtgcagtcagggacc atagcacaagacaggcgtcttctactggtgctaccagcaa atgctggaagccgggaacactgggtacgtcggaaaccacg tgatgtgaagaagtaagataaactgtaggagaaaagcatt tcgtagtgggccatgaagcctttcaggacatgtattgcag tatgggccggcccattacgcaattggacgacaacaaagac tagtattagtaccacctcggctatccacatagatcaaagc tgatttaaaagagttgtgcagatgatccgtggcaacaaag caccagtggtctagtggtagaatagtaccctgccacggta cagacccgggttcgattcccggctggtgcaagagaccgat atcccatggctcgagggtctcggttttagagctagaaata gcaagttaaaataaggctagtccgttatcaacttgaaaaa gtggcaccgagtcggtgctttttttccacataatctctag aggatccccggcgtaatcatggtcatagctgtttcctgtg tgaaattgttatccgctcacaattccacacaacatacgag ccggaagcataaagtgtaaagcctggggtgcctaatgagt gagctaactcacattaattgcgttgcgctcactgcccgct ttccagtcgggaaacctgtcgtgccagctgcattaatgaa tcggccaacgcgcggggagaggcggtttgcgtattgggcg ctcttccgcttcctcgctcactgactcgctgcgctcggtc gttcggctgcggcgagcggtatcagctcactcaaaggcgg taatacggttatccacagaatcaggggataacgcaggaaa gaacatgtgagcaaaaggccagcaaaaggccaggaaccgt aaaaaggccgcgttgctggcgtttttccataggctccgcc cccctgacgagcatcacaaaaatcgacgctcaagtcagag gtggcgaaacccgacaggactataaagataccaggcgttt ccccctggaagctccctcgtgcgctctcctgttccgaccc tgccgcttaccggatacctgtccgcctttctcccttcggg aagcgtggcgctttctcatagctcacgctgtaggtatctc agttcggtgtaggtcgttcgctccaagctgggctgtgtgc acgaaccccccgttcagcccgaccgctgcgccttatccgg taactatcgtcttgagtccaacccggtaagacacgactta tcgccactggcagcagccactggtaacaggattagcagag cgaggtatgtaggcggtgctacagagttcttgaagtggtg gcctaactacggctacactagaagaacagtatttggtatc tgcgctctgctgaagccagttaccttcggaaaaagagttg gtagctcttgatccggcaaacaaaccaccgctggtagcgg -continued tggtttttttgtttgcaagcagcagattacgcgcagaaaa aaaggatctcaagaagatcctttgatcttttctacggggt ctgacgctcagtggaacgaaaactcacgttaagggatttt ggtcatgagattatcaaaaaggatcttcacctagatcctt ttaaattaaaaatgaagttttaaatcaatctaaagtatat atgagtaaacttggtctgacagttaccaatgcttaatcag tgaggcacctatctcagcgatctgtctatttcgttcatcc atagttgcctgactccccgtcgtgtagataactacgatac gggagggcttaccatctggccccagtgctgcaatgatacc gcgactcccacgctcaccggctccagatttatcagcaata aaccagccagccggaagggccgagcgcagaagtggtcctg caactttatccgcctccatccagtctattaattgttgccg ggaagctagagtaagtagttcgccagttaatagtttgcgc aacgttgttgccattgctacaggcatcgtggtgtcacgct cgtcgtttggtatggcttcattcagctccggttcccaacg atcaaggcgagttacatgatcccccatgttgtgcaaaaaa gcggttagctccttcggtcctccgatcgttgtcagaagta agttggccgcagtgttatcactcatggttatggcagcact gcataattctcttactgtcatgccatccgtaagatgcttt tctgtgactggtgagtactcaaccaagtcattctgagaat agtgtatgcggcgaccgagttgctcttgcccggcgtcaat acgggataataccgcgccacatagcagaactttaaaagtg ctcatcattggaaaacgttcttcggggcgaaaactctcaa ggatcttaccgctgttgagatccagttcgatgtaacccac tcgtgcacccaactgatcttcagcatcttttactttcacc agcgtttctgggtgagcaaaaacaggaaggcaaaatgccg caaaaaagggaataagggcgacacgaaatgttgaatact catactcttcctttttcaatattattgaagcatttatcag ggttattgtctcatgagcggatacatatttgaatgtattt agaaaaataaacaaatagggggttccgcgcacatttcccg aaaagtgccacctgacgtctaagaaaccattattatcatg acattaacctataaaaataggcgtatcacgaggccctttc gtc sequence of 5' end ribozyme

SEQ ID NO: 12
NNNNNNCTGATGAGTCCGTGAGGACGAAACGAGTAAGCTCGTC sequence of 3' end ribozyme

SEQ ID NO: 13
GGCCGGCATGGTCCCAGCCTCCTCGCTGGCGCCGGCTGGG

CAACATGCTTCGGCATGGCGAATGGGAC

AAGAAGAGAAAGGTC

SEQ ID NO: 15
CCCAAGAAGAAGAGGAAGGTG

SEQ ID NO: 16
CCAAAGAAGAAGAGGAAGGTT

SEQ ID NO: 17
SGGSPKKKRKV

SEQ ID NO: 18
TCGGGGGGAGCCCAAGAAGAAGCGGAAGGTG

SEQ ID NO: 19
PKKKRKV

SEQ ID NO: 20
AGGTCGGGGAGGGGACGTACGGG

SEQ ID NO: 21
GGCAAGGTCGGGGAGGGGACGTAC

SEQ ID NO: 22
AAACGTACGTCCCCTCCCCGACCT

SEQ ID NO: 23
GACGTCGGCGAGGAAGGCCTCGG

SEQ ID NO: 24
GGCAGACGTCGGCGAGGAAGGCCT

SEQ ID NO: 25
AAACAGGCCTTCCTCGCCGACGTC

SEQ ID NO: 26
CATGGTGGGGAAAGCTTGGAGGG

SEQ ID NO: 27
GGCACATGGTGGGGAAAGCTTGGA

SEQ ID NO: 28
AAACTCCAAGCTTTCCCCACCATG

SEQ ID NO: 29
CCGGACGACGACGTCGACGACGG

SEQ ID NO: 30
GGCACCGGACGACGACGTCGACGA

SEQ ID NO: 31
AAACTCGTCGACGTCGTCGTCCGG

SEQ ID NO: 32
TTGAAGTCCCTTCTAGATGGAGG

SEQ ID NO: 33
GGCATTGAAGTCCCTTCTAGATGG

SEQ ID NO: 34
AAACCCATCTAGAAGGGACTTCAA

SEQ ID NO: 35
ACTGCGACACCCAGATATCGTGG

SEQ ID NO: 36
GGCAACTGCGACACCCAGATATCG

SEQ ID NO: 37
AAACCGATATCTGGGTGTCGCAGT

SEQ ID NO: 38
GTTGGTCTTTGCTCCTGCAGAGG

SEQ ID NO: 39
GGCAGTTGGTCTTTGCTCCTGCAG

SEQ ID NO: 40
AAACCTGCAGGAGCAAAGACCAAC

SEQ ID NO: 41
TGCAAGGTCGGGGAGGGGACGTAC

SEQ ID NO: 42
TGCAGACGTCGGCGAGGAAGGCCT

SEQ ID NO: 43
TGCACATGGTGGGGAAAGCTTGGA

SEQ ID NO: 44
TGCACCGGACGACGACGTCGACGA

SEQ ID NO: 45
TGCATTGAAGTCCCTTCTAGATGG

SEQ ID NO: 46
TGCACTGCGACACCCAGATATCG

SEQ ID NO: 47
TGCAGTTGGTCTTTGCTCCTGCAG

SEQ ID NO: 48
GGCGTTGGTCTTTGCTCCTGCAG

SEQ ID NO: 49
GGCGGTTGGTCTTTGCTCCTGCAG

SEQ ID NO: 50
GGTGAGTGAGTGTGTGCGTGTGG

SEQ ID NO: 51
CACCGGTGAGTGAGTGTGTGCGTG

SEQ ID NO: 52
AAACCACGCACACACTCACTCACC

SEQ ID NO: 53
CACCGGGTGAGTGAGTGTGTGCGTG

SEQ ID NO: 54
AAACCACGCACACACTCACTCACCC

SEQ ID NO: 55
CACCGaacaaagcaccagtggtctagtggtagaatagtac
cctgccacggtacagacccgggttcgattcccggctggtg
caGGTGAGTGAGTGTGTGCGTG SEQ ID NO: 56
AAACCACGCACACACTCACTCACCtgcaccagccgggaat
cgaacccgggtctgtaccgtggcagggtactattctacca
ctagaccactggtgctttgttC

SEQ ID NO: 57
NNNNNNNNNNNNNNNNNNNNNNTTTTTTT

SEQ ID NO: 58
NNNNNNNNNNNNNNNNNNNNNTTTTTTT

SEQ ID NO: 59
TGGAGTTGGTCTTTGCTCCTGCAGAGG

SEQ ID NO: 60
GACGCCGGCGAGGAAGGCCTCGG

SEQ ID NO: 61
GCAGTCGGAGAGGAAGGCCTGGG

SEQ ID NO: 62
AGATCGGGGAGGGGACGTACGGG

SEQ ID NO: 63
AGGTGGGGAAGGGACGTACGGG

SEQ ID NO: 64
AGATTGGGGAGGGCACGTACGGG

| | |
|---|---|
| AGCGTCGGCGAGGAAGGCCTCGG | SEQ ID NO: 65 |
| GGTGTCGGCGAGGAAGGCCTCGG | SEQ ID NO: 66 |
| GATATCGGCGAGGAAGGCCTCGG | SEQ ID NO: 67 |
| GACACCGGCGAGGAAGGCCTCGG | SEQ ID NO: 68 |
| GACGCTGGCGAGGAAGGCCTCGG | SEQ ID NO: 69 |
| GACGTTAGCGAGGAAGGCCTCGG | SEQ ID NO: 70 |
| GACGTCAACGAGGAAGGCCTCGG | SEQ ID NO: 71 |
| GACGTCGATGAGGAAGGCCTCGG | SEQ ID NO: 72 |
| GACGTCGGTAAGGAAGGCCTCGG | SEQ ID NO: 73 |
| GACGTCGGCAGGGAAGGCCTCGG | SEQ ID NO: 74 |
| GACGTCGGCGGAGAAGGCCTCGG | SEQ ID NO: 75 |
| GACGTCGGCGAAAAAGGCCTCGG | SEQ ID NO: 76 |
| GACGTCGGCGAGAGAGGCCTCGG | SEQ ID NO: 77 |
| GACGTCGGCGAGGGGGCCTCGG | SEQ ID NO: 78 |
| GACGTCGGCGAGGAGAGCCTCGG | SEQ ID NO: 79 |
| GACGTCGGCGAGGAAAACCTCGG | SEQ ID NO: 80 |
| GACGTCGGCGAGGAAGATCTCGG | SEQ ID NO: 81 |
| GACGTCGGCGAGGAAGGTTTCGG | SEQ ID NO: 82 |
| GACGTCGGCGAGGAAGGCTCCGG | SEQ ID NO: 83 |
| GCTGAGTGAGTGTATGCGTGTGG | SEQ ID NO: 84 |
| TGTGGGTGAGTGTGTGCGTGAGG | SEQ ID NO: 85 |

The invention claimed is:

1. A method for genetically modifying a cell, comprising:
introducing into the cell a genome editing system for site-directed modification of a target sequence, wherein the Cas9 nuclease variant is targeted to the target sequence in the genome of the cell by the guide RNA, and results in substitution, deletion and/or addition of one or more nucleotides in the target sequence,
wherein the genome editing system comprises at least one selected from the following (i) to (iii):
(i) a Cas9 nuclease variant, and an expression construct comprising a nucleotide sequence encoding a tRNA-guide RNA fusion;
(ii) an expression construct comprising a nucleotide sequence encoding a Cas9 nuclease variant, and an expression construct comprising a nucleotide sequence encoding a tRNA-guide RNA fusion; and
(iii) an expression construct comprising a nucleotide sequence encoding a Cas9 nuclease variant and a nucleotide sequence encoding a tRNA-guide RNA fusion;
wherein the Cas9 nuclease variant has higher specificity as compared with the wild-type Cas9 nuclease, wherein the Cas9 nuclease variant comprises the amino acid sequence as set forth in SEQ ID NO: 4, SEQ ID NO: 5 or SEQ ID NO: 6; wherein the 5' end of the guide RNA is linked to the 3' end of the tRNA, and the guide RNA is 20 nt in length; and wherein the fusion of guide RNA and the tRNA is cleaved at the 5' end of the guide RNA after being transcribed in the cell, thereby forming a guide RNA that does not carry an extra nucleotide at the 5' end.

2. The method of claim 1, wherein the cell is derived from mammals; poultry; or plants.

3. The method of claim 1, wherein the genome editing system is introduced into the cell by a method selected from:

calcium phosphate transfection, protoplast fusion, electroporation, liposome transfection, microinjection, viral infection, particle bombardment, PEG-mediated protoplast transformation and *agrobacterium*-mediated transformation.

4. The method of claim 2, wherein the mammal is a human, a mouse, a rat, a monkey, a dog, a pig, a sheep, a cow or a cat; wherein the poultry is a chicken, a duck or a goose; and wherein the plant is rice, maize, wheat, sorghum, barley, soybean, peanut and *Arabidopsis thaliana*.

5. The method of claim 1, wherein the tRNA and the cell to be modified are derived from a same species.

6. The method of claim 1, wherein the nucleotide sequence encoding the Cas9 nuclease variant is codon-optimized for the organism from which the cell to be modified is derived.

7. The method of claim 1, wherein the guide RNA is a single guide RNA (sgRNA).

* * * * *

SEQUENCE LISTING

```
Sequence total quantity: 85
SEQ ID NO: 1                    moltype = DNA   length = 77
FEATURE                         Location/Qualifiers
misc_feature                    1..77
                                note = tRNA encoding sequence
source                          1..77
                                mol_type = other DNA
                                organism = synthetic construct
SEQUENCE: 1
aacaaagcac cagtggtcta gtggtagaat agtaccctgc cacggtacag acccgggttc   60
gattcccggc tggtgca                                                  77

SEQ ID NO: 2                    moltype = DNA   length = 4206
FEATURE                         Location/Qualifiers
misc_feature                    1..4206
                                note = SpCas9 nucleotide sequence
source                          1..4206
                                mol_type = other DNA
                                organism = synthetic construct
SEQUENCE: 2
atggccccta agaagaagag aaaggtcggt attcacggcg ttcctgcggc gatggacaag   60
aagtatagta ttggtctgga cattgggacg aattccgttg gctgggccgt gatcaccgat  120
gagtacaagg tcccttccaa gaagtttaag gttctgggga acaccgatcg gcacagcatc  180
aagaagaatc tcattggagc cctcctgttc gactcaggcg agaccgccga agcaacaagg  240
ctcaagagaa ccgcaaggag acgtatacac agaaggaaga ataggatctg ctacctgcag  300
gagattttca gcaacgaaat ggcgaaggtg gacgattcgt tctttcatag attggaggag  360
agtttcctcg tcgaggaaga taagaagcac gagaggcatc ctatctttgg caacattgtc  420
gacgaggttg cctatcacga aaagtacccc acaatctatc atctgcggaa gaagcttgtg  480
gactcgactg ataaggcgga ccttagattg atctacctcg ctctggcaca catgattaag  540
ttcagggggc attttctgat cgaggggat cttaacccgg acaatagcga tgtggacaag  600
ttgttcatcc agctcgtcca aacctacaat cagctctttg aggaaaaccc aattaatgct  660
tcaggcgtcg acgccaaggc gatcctgtct gcacgccttt caaagtctcg ccggcttgag  720
aacttgatcg ctcaactccc gggcgaaaag aagaacggct tgttcgggaa tctcattgca  780
ctttcgttgg ggctcacacc aaacttcaag agtaattttg atctgctga ggacgcaaag  840
ctgcagcttt ccaaggacac ttatgacgat gacctggata accttttggc ccaaatcggc  900
gatcagtacg cggacttgtt cctcgccgcg aagaatttgt cggacgcgat cctcctgagt  960
gatattctcc gcgtgaacac cgagattaca aaggcccgc tctcggcgag tatgatcaag 1020
cgctatgacg agcaccatca ggatctgacc cttttgaagg ctttggtccg gcagcaactc 1080
ccagagaagt acaaggaaat cttctttgat caatccaaga acggctacgc tggttatatt 1140
gacggcgggg catcgcagga ggaattctac aagtttatca gccaattct ggagaagatg 1200
gatggcacag aggaactcct ggtgaagctc aataggggagg accttttgcg gaagcaaaga 1260
actttcgata acggcagcat ccctcaccag attcatctcg ggagctgca cgccatcctg 1320
```

-continued

```
agaaggcagg aagacttcta cccctttctt aaggataacc gggagaagat cgaaaagatt 1380
ctgacgttca gaattccgta ctatgtcgga ccactcgccc ggggtaattc cagatttgcg 1440
tggatgacca gaaagagcga ggaaaccatc acaccttgga acttcgagga agtggtcgat 1500
aagggcgctt ccgcacagag cttcattgag cgcatgacaa attttgacaa gaacctgcct 1560
aatgagaagg tccttcccaa gcattccctc ctgtacgagt atttcactgt ttataacgaa 1620
ctcacgaagg tgaagtatgt gaccgaggga atgcgcaagc cgccttcct gagcggcgag 1680
caaaagaagg cgatcgtgga ccttttgttt aagaccaatc ggaaggtcac agttaagcag 1740
ctcaaggagg actacttcaa gaagattgaa tgcttcgatt ccgttgagat cagcggcgtg 1800
gaagacaggt ttaacgcgtc actggggact taccacgatc tcctgaagat cattaaggat 1860
aaggacttct tggacaacga ggaaaatgag gatatcctcg aagacattgt cctgactctt 1920
acgttgtttg aggataggga aatgatcgag gaacgcttga agacgtatgc ccatctcttc 1980
gatgacaagg ttatgaagca gctcaagaga gaaagataca ccggatgggg aaggctgtcc 2040
cgcaagctta tcaatggcat tagagacaag caatcaggga agacaatcct tgactttttg 2100
aagtctgatg gcttcgcgaa caggaatttt atgcagctga ttcacgatga ctcacttact 2160
ttcaaggagg atatccagaa ggctcaagtg tcgggacaag gtgacagtct gcacgagcat 2220
atcgccaacc ttgcgggatc tcctgcaatc aagaagggta ttctgcagac agtcaaggtt 2280
gtggatgagc ttgtgaaggt catgggacgg cataagcccg agaacatcgt tattgagatg 2340
gccagagaaa atcagaccac acaaaagggt cagaagaact cgaggggagcg catgaagcgc 2400
atcgaggaag gcattaagga gctggggagt cagatcctta aggagcaccc ggtgaaaaac 2460
acgcagttgc aaaatgagaa gctctatctg tactatctgc aaaatggcag ggatatgtat 2520
gtggaccagg agttggatat taaccgcctc tcggattacg acgtcgatca tatcgttcct 2580
cagtccttcc ttaaggatga cagcattgac aataaggttc tcaccaggtc cgacaagaac 2640
cgcgggaagt ccgataatgt gccagcgag gaagtcgtta agaagatgaa gaactactgg 2700
aggcaacttt tgaatgccaa gttgatcaca cagaggaagt ttgataacct cactaaggcc 2760
gagcgcggag gtctcagcga actggacaag gcgggcttca ttaagcggca actggttgag 2820
actagacaga tcacgaagca cgtggcgcag attctcgatt cacgcatgaa cacgaagtac 2880
gatgagaatg acaagctgat ccgggaagtg aaggtcatca ccttgaagtc aaagctcgtt 2940
tctgacttca ggaaggattt ccaatttat aaggtgcgcg agatcaacaa ttatcaccat 3000
gctcatgacg catacctcaa cgctgtggtc ggaacagcat tgattaagaa gtacccgaag 3060
ctcgagtccg aattcgtgta cggtgactat aaggtttacg atgtgcgcaa gatgatcgcc 3120
aagtcagagc aggaaattgg caaggccact gcgaagtatt tcttttactc taacattatg 3180
aatttcttta agactgagat cacgctggct aatggcgaaa tccggaagag accacttatt 3240
gagaccaacg gcgagacagg ggaaatcgtg tgggacaagg ggagggattt cgccacagtc 3300
cgcaaggttc tctctatgcc tcaagtgaat attgtcaaga agactgaagt ccagacgggc 3360
gggttctcaa aggaatctat tctgcccaag cggaactcgg ataagcttat cgccagaaag 3420
aaggactggg acccgaagaa gtatggaggt ttcgactcac caacggtggc ttactctgtc 3480
ctggttgtgg caaaggtgga aaggggaaag tcaagaagc tcaagtctgt caaggagctc 3540
ctgggtatca ccattatgga gaggtccagc ttcgaaaaga atccgatcga tttcctcgag 3600
gcgaagggat ataaggaagt gaagaaggac ctgatcatta agcttccaaa gtacagtctt 3660
ttcgagttgg aaaacggcag gaagcgcatg ttggcttccg caggagagct ccagaagggg 3720
aacgagcttg ctttgccgtc caagtatgtg aacttcctct atctggcatc ccactacgag 3780
aagctcaagg cagcccaga ggataacgaa cagaagcaac tgtttgtgga gcaacacaag 3840
cattatcttg acgagatcat tgaacagatt cggagttca gtaagcgcat tcctctcgtc 3900
gacgcgaatt tggataaggt tctctcagcc tacaacaagc accgggacaa gcctatcaga 3960
gagcaggcgg aaaatatcat tcatctcttc accctgacaa accttgggc tccgctgca 4020
ttcaagtatt ttgacactac gattgatcgg aagagataca cttctacgaa ggaggtgctg 4080
gatgcaaccc ttatccacca atcgattact ggcctctacg agacgcggat cgacttgagt 4140
cagctcgggg gggataagag accagcggca accaagaagg caggacaagc gaagaagaag 4200
aagtag                                                              4206
```

SEQ ID NO: 3    moltype = AA    length = 1401
FEATURE         Location/Qualifiers
source          1..1401
                mol_type = protein
                organism = Streptococcus pyogenes
SEQUENCE: 3

```
MAPKKKRKVG IHGVPAAMDK KYSIGLDIGT NSVGWAVITD EYKVPSKKFK VLGNTDRHSI  60
KKNLIGALLF DSGETAEATR LKRTARRRYT RRKNRICYLQ EIFSNEMAKV DDSFFHRLEE 120
SFLVEEDKKH ERHPIFGNIV DEVAYHEKYP TIYHLRKKLV DSTDKADLRL IYLALAHMIK 180
FRGHFLIEGD LNPDNSDVDK LFIQLVQTYN QLFEENPINA SGVDAKAILS ARLSKSRRLE 240
NLIAQLPGEK KNGLFGNLIA LSLGLTPNFK SNFDLAEDAK LQLSKDTYDD DLDNLLAQIG 300
DQYADLFLAA KNLSDAILLS DILRVNTEIT KAPLSASMIK RYDEHHQDLT LLKALVRQQL 360
PEKYKEIFFD QSKNGYAGYI DGGASQEEFY KFIKPILEKM DGTEELLVKL NREDLLRKQR 420
TFDNGSIPHQ IHLGELHAIL RRQEDFYPFL KDNREKIEKI LTFRIPYYVG PLARGNSRFA 480
WMTRKSEETI TPWNFEEVVD KGASAQSFIE RMTNFDKNLP NEKVLPKHSL LYEYFTVYNE 540
LTKVKYVTEG MRKPAFLSGE QKKAIVDLLF KTNRKVTVKQ LKEDYFKKIE CFDSVEISGV 600
EDRFNASLGT YHDLLKIIKD KDFLDNEENE DILEDIVLTL TLFEDREMIE ERLKTYAHLF 660
DDKVMKQLKR RRYTGWGRLS RKLINGIRDK QSGKTILDFL KSDGFANRNF MQLIHDDSLT 720
FKEDIQKAQV SGQGDSLHEH IANLAGSPAI KKGILQTVKV VDELVKVMGR HKPENIVIEM 780
ARENQTTQKG QKNSRERMKR IEEGIKELGS QILKEHPVEN TQLQNEKLYL YYLQNGRDMY 840
VDQELDINRL SDYDVDHIVP QSFLKDDSID NKVLTRSDKN RGKSDNVPSE EVVKKMKNYW 900
RQLLNAKLIT QRKFDNLTKA ERGGLSELDK AGFIKRQLVE TRQITKHVAQ ILDSRMNTKY 960
DENDKLIREV KVITLKSKLV SDFRKDFQFY KVREINNYHH AHDAYLNAVV GTALIKKYPK 1020
LESEFVYGDY KVYDVRKMIA KSEQEIGKAT AKYFFYSNIM NFFKTEITLA NGEIRKRPLI 1080
ETNGETGEIV WDKGRDFATV RKVLSMPQVN IVKKTEVQTG GFSKESILPK RNSDKLIARK 1140
KDWDPKKYGG FDSPTVAYSV LVVAKVEKGK SKKLKSVKEL LGITIMERSS FEKNPIDFLE 1200
AKGYKEVKKD LIIKLPKYSL FELENGRKRM LASAGELQKG NELALPSKYV NFLYLASHYE 1260
KLKGSPEDNE QKQLFVEQHK HYLDEIIEQI SEFSKRVILA DANLDKVLSA YNKHRDKPIR 1320
EQAENIIHLF TLTNLGAPAA FKYFDTTIDR KRYTSTKEVL DATLIHQSIT GLYETRIDLS 1380
```

```
QLGGDKRPAA TKKAGQAKKK K                                              1401

SEQ ID NO: 4             moltype = AA  length = 1401
FEATURE                  Location/Qualifiers
REGION                   1..1401
                         note = eSpCas9(1.0) amino acid sequence
source                   1..1401
                         mol_type = protein
                         organism = synthetic construct
SEQUENCE: 4
MAPKKKRKVG IHGVPAAMDK KYSIGLDIGT NSVGWAVITD EYKVPSKKFK VLGNTDRHSI    60
KKNLIGALLF DSGETAEATR LKRTARRRYT RRKNRICYLQ EIFSNEMAKV DDSFFHRLEE    120
SFLVEEDKKH ERHPIFGNIV DEVAYHEKYP TIYHLRKKLV DSTDKADLRL IYLALAHMIK    180
FRGHFLIEGD LNPDNSDVDK LFIQLVQTYN QLFEENPINA SGVDAKAILS ARLSKSRRLE    240
NLIAQLPGEK KNGLFGNLIA LSLGLTPNFK SNFDLAEDAK LQLSKDTYDD DLDNLLAQIG    300
DQYADLFLAA KNLSDAILLS DILRVNTEIT KAPLSASMIK RYDEHHQDLT LLKALVRQQL    360
PEKYKEIFFD QSKNGYAGYI DGGASQEEFY KFIKPILEKM DGTEELLVKL NREDLLRKQR    420
TFDNGSIPHQ IHLGELHAIL RRQEDFYPFL KDNREKIEKI LTFRIPYYVG PLARGNSRFA    480
WMTRKSEETI TPWNFEEVVD KGASAQSFIE RMTNFDKNLP NEKVLPKHSL LYEYFTVYNE    540
LTKVKYVTEG MRKPAFLSGE QKKAIVDLLF KTNRKVTVKQ LKEDYFKKIE CFDSVEISGV    600
EDRFNASLGT YHDLLKIIKD KDFLDNEENE DILEDIVLTL TLFEDREMIE ERLKTYAHLF    660
DDKVMKQLKR RRYTGWGRLS RKLINGIRDK QSGKTILDFL KSDGFANRNF MQLIHDDSLT    720
FKEDIQKAQV SGQGDSLHEH IANLAGSPAI KKGILQTVKV VDELVKVMGR HKPENIVIEM    780
ARENQTTQKG QKNSRERMKR IEEGIKELGS QILKEHPVEN TQLQNEALYL YYLQNGRDMY    840
VDQELDINRL SDYDVDHIVP QSFLKDDSID NKVLTRSDKN RGKSDNVPSE EVVKKMKNYW    900
RQLLNAKLIT QRKFDNLTKA ERGGLSELDK AGFIKRQLVE TRQITKHVAQ ILDSRMNTKY    960
DENDKLIREV KVITLKSKLV SDFRKDFQFY KVREINNYHH AHDAYLNAVV GTALIKKYPA    1020
LESEFVYGDY KVYDVRKMIA KSEQEIGKAT AKYFFYSNIM NFFKTEITLA NGEIRKAPLI    1080
ETNGETGEIV WDKGRDFATV RKVLSMPQVN IVKKTEVQTG GFSKESILPK RNSDKLIARK    1140
KDWDPKKYGG FDSPTVAYSV LVVAKVEKGK SKKLKSVKEL LGITIMERSS FEKNPIDFLE    1200
AKGYKEVKKD LIIKLPKYSL FELENGRKRM LASAGELQKG NELALPSKYV NFLYLASHYE    1260
KLKGSPEDNE QKQLFVEQHK HYLDEIIEQI SEFSKRVILA DANLDKVLSA YNKHRDKPIR    1320
EQAENIIHLF TLTNLGAPAA FKYFDTTIDR KRYTSTKEVL DATLIHQSIT GLYETRIDLS    1380
QLGGDKRPAA TKKAGQAKKK K                                              1401

SEQ ID NO: 5             moltype = AA  length = 1401
FEATURE                  Location/Qualifiers
REGION                   1..1401
                         note = eSpCas9(1.1) amino acid sequence
source                   1..1401
                         mol_type = protein
                         organism = synthetic construct
SEQUENCE: 5
MAPKKKRKVG IHGVPAAMDK KYSIGLDIGT NSVGWAVITD EYKVPSKKFK VLGNTDRHSI    60
KKNLIGALLF DSGETAEATR LKRTARRRYT RRKNRICYLQ EIFSNEMAKV DDSFFHRLEE    120
SFLVEEDKKH ERHPIFGNIV DEVAYHEKYP TIYHLRKKLV DSTDKADLRL IYLALAHMIK    180
FRGHFLIEGD LNPDNSDVDK LFIQLVQTYN QLFEENPINA SGVDAKAILS ARLSKSRRLE    240
NLIAQLPGEK KNGLFGNLIA LSLGLTPNFK SNFDLAEDAK LQLSKDTYDD DLDNLLAQIG    300
DQYADLFLAA KNLSDAILLS DILRVNTEIT KAPLSASMIK RYDEHHQDLT LLKALVRQQL    360
PEKYKEIFFD QSKNGYAGYI DGGASQEEFY KFIKPILEKM DGTEELLVKL NREDLLRKQR    420
TFDNGSIPHQ IHLGELHAIL RRQEDFYPFL KDNREKIEKI LTFRIPYYVG PLARGNSRFA    480
WMTRKSEETI TPWNFEEVVD KGASAQSFIE RMTNFDKNLP NEKVLPKHSL LYEYFTVYNE    540
LTKVKYVTEG MRKPAFLSGE QKKAIVDLLF KTNRKVTVKQ LKEDYFKKIE CFDSVEISGV    600
EDRFNASLGT YHDLLKIIKD KDFLDNEENE DILEDIVLTL TLFEDREMIE ERLKTYAHLF    660
DDKVMKQLKR RRYTGWGRLS RKLINGIRDK QSGKTILDFL KSDGFANRNF MQLIHDDSLT    720
FKEDIQKAQV SGQGDSLHEH IANLAGSPAI KKGILQTVKV VDELVKVMGR HKPENIVIEM    780
ARENQTTQKG QKNSRERMKR IEEGIKELGS QILKEHPVEN TQLQNEKLYL YYLQNGRDMY    840
VDQELDINRL SDYDVDHIVP QSFLADDSID NKVLTRSDKN RGKSDNVPSE EVVKKMKNYW    900
RQLLNAKLIT QRKFDNLTKA ERGGLSELDK AGFIKRQLVE TRQITKHVAQ ILDSRMNTKY    960
DENDKLIREV KVITLKSKLV SDFRKDFQFY KVREINNYHH AHDAYLNAVV GTALIKKYPA    1020
LESEFVYGDY KVYDVRKMIA KSEQEIGKAT AKYFFYSNIM NFFKTEITLA NGEIRKAPLI    1080
ETNGETGEIV WDKGRDFATV RKVLSMPQVN IVKKTEVQTG GFSKESILPK RNSDKLIARK    1140
KDWDPKKYGG FDSPTVAYSV LVVAKVEKGK SKKLKSVKEL LGITIMERSS FEKNPIDFLE    1200
AKGYKEVKKD LIIKLPKYSL FELENGRKRM LASAGELQKG NELALPSKYV NFLYLASHYE    1260
KLKGSPEDNE QKQLFVEQHK HYLDEIIEQI SEFSKRVILA DANLDKVLSA YNKHRDKPIR    1320
EQAENIIHLF TLTNLGAPAA FKYFDTTIDR KRYTSTKEVL DATLIHQSIT GLYETRIDLS    1380
QLGGDKRPAA TKKAGQAKKK K                                              1401

SEQ ID NO: 6             moltype = AA  length = 1401
FEATURE                  Location/Qualifiers
REGION                   1..1401
                         note = SpCas9-HF1 amino acid sequence
source                   1..1401
                         mol_type = protein
                         organism = synthetic construct
SEQUENCE: 6
MAPKKKRKVG IHGVPAAMDK KYSIGLDIGT NSVGWAVITD EYKVPSKKFK VLGNTDRHSI    60
KKNLIGALLF DSGETAEATR LKRTARRRYT RRKNRICYLQ EIFSNEMAKV DDSFFHRLEE    120
SFLVEEDKKH ERHPIFGNIV DEVAYHEKYP TIYHLRKKLV DSTDKADLRL IYLALAHMIK    180
```

```
FRGHFLIEGD  LNPDNSDVDK  LFIQLVQTYN  QLFEENPINA  SGVDAKAILS  ARLSKSRRLE   240
NLIAQLPGEK  KNGLFGNLIA  LSLGLTPNFK  SNFDLAEDAK  LQLSKDTYDD  DLDNLLAQIG   300
DQYADLFLAA  KNLSDAILLS  DILRVNTEIT  KAPLSASMIK  RYDEHHQDLT  LLKALVRQQL   360
PEKYKEIFFD  QSKNGYAGYI  DGGASQEEFY  KFIKPILEKM  DGTEELLVKL  NREDLLRKQR   420
TFDNGSIPHQ  IHLGELHAIL  RRQEDFYPFL  KDNREKIEKI  LTFRIPYYVG  PLARGNSRFA   480
WMTRKSEETI  TPWNFEEVVD  KGASAQSFIE  RMTAFDKNLP  NEKVLPKHSL  LYEYFTVYNE   540
LTKVKYVTEG  MRKPAFLSGE  QKKAIVDLLF  KTNRKVTVKQ  LKEDYFKKIE  CFDSVEISGV   600
EDRFNASLGT  YHDLLKIIKD  KDFLDNEENE  DILEDIVLTL  TLFEDREMIE  ERLKTYAHLF   660
DDKVMKQLKR  RRYTGWGALS  RKLINGIRDK  QSGKTILDFL  KSDGFANRNF  MALIHDDSLT   720
FKEDIQKAQV  SGQGDSLHEH  IANLAGSPAI  KKGILQTVKV  VDELVKVMGR  HKPENIVIEM   780
ARENQTTQKG  QKNSRERMKR  IEEGIKELGS  QILKEHPVEN  TQLQNEKLYL  YYLQNGRDMY   840
VDQELDINRL  SDYDVDHIVP  QSFLKDDSID  NKVLTRSDKN  RGKSDNVPSE  EVVKKMKNYW   900
RQLLNAKLIT  QRKFDNLTKA  ERGGLSELDK  AGFIKRQLVE  TRAITKHVAQ  ILDSRMNTKY   960
DENDKLIREV  KVITLKSKLV  SDFRKDFQFY  KVREINNYHH  AHDAYLNAVV  GTALIKKYPK  1020
LESEFVYGDY  KVYDVRKMIA  KSEQEIGKAT  AKYFFYSNIM  NFFKTEITLA  NGEIRKRPLI  1080
ETNGETGEIV  WDKGRDFATV  RKVLSMPQVN  IVKKTEVQTG  GFSKESILPK  RNSDKLIARK  1140
KDWDPKKYGG  FDSPTVAYSL  LVVAKVEKGK  SKKLKSVKEL  LGITIMERSS  FEKNPIDFLE  1200
AKGYKEVKKD  LIIKLPKYSL  FELENGRKRM  LASAGELQKG  NELALPSKYV  NFLYLASHYE  1260
KLKGSPEDNE  QKQLFVEQHK  HYLDEIIEQI  SEFSKRVILA  DANLDKVLSA  YNKHRDKPIR  1320
EQAENIIHLF  TLTNLGAPAA  FKYFDTTIDR  KRYTSTKEVL  DATLIHQSIT  GLYETRIDLS  1380
QLGGDKRPAA  TKKAGQAKKK  K                                             1401

SEQ ID NO: 7             moltype = DNA   length = 4206
FEATURE                  Location/Qualifiers
misc_feature             1..4206
                         note = eSpCas9(1.0) codon-optimized nucleotide sequence
source                   1..4206
                         mol_type = other DNA
                         organism = synthetic construct
SEQUENCE: 7
atggcccta   agaagaagag   aaaggtcggt   attcacggcg   ttcctgcggc   gatggacaag     60
aagtatagta  ttggtctgga   cattgggacg   aattccgttg   gctgggccgt   gatcaccgat    120
gagtacaagg  tcccttccaa   gaagtttaag   gttctgggga   caccgatcg   gcacagcatc    180
aagaagaatc  tcattggagc   cctcctgttc   gactcaggcg   agacggccga   agcaacaagg    240
ctcaagagaa  ccgcaaggag   acggtataca   agaggaaga   ataggatctg   ctacctgcag    300
gagattttca  gcaacgaaat   ggcgaaggtg   gacgattcgt   tctttcatag   attggaggag    360
agtttcctcg  tcgaggaaga   taagaagcac   gagaggcatc   ctatctttgg   caacattgtc    420
gacgaggttg  cctatcacga   aaagtacccc   acaatctatc   atctgcgaa   gaagcttgtg    480
gactcgactg  ataaggcgga   cctagattg   atctacctcg   ctctggcaca   catgattaag    540
ttcaggggcc  attttctgat   cgaggggat   cttaacccgg   acaatagcga   tgtggacaag    600
ttgttcatcc  agctcgtcca   aacctacaat   cagctctttg   aggaaaaccc   aattaatgct    660
tcaggcgtcg  acgccaaggc   gatcctgtct   gcacgccttt   caaagtctcg   ccggcttgag    720
aacttgatcg  ctcaactccc   gggcgaaaag   aagaacgctt   gttcgggaaa   tctcattgca    780
ctttcgttgg  ggctcacacc   aaacttcaag   agtaattttg   atctcgctga   ggacgcaaag    840
ctgcagcttt  ccaaggacac   ttatgacgat   gacctggata   ccttttggc    caaatcggc     900
gatcagtacg  cggacttgtt   cctcgccgcg   aagaatttgt   cggacgcgat   cctcctgagt    960
gatattctcc  gcgtgaacac   cgagattaca   aaggcccgc    tctcggcgaa   tatgatcaag   1020
cgctatgacg  agcaccatca   ggatctgacc   cttttgaagg   cttggtccg    gcagcaactc   1080
ccagagaagt  acaaggaaat   cttctttgat   caatccaaga   acggctacgc   tggttatatt   1140
gacggcgggg  catcgcagga   ggaattctac   aagtttatca   agccaattct   ggagaagatg   1200
gatggcacag  aggaactcct   ggtgaagctc   aatagggagg   acctttttcg   gaagcaaaga   1260
actttcgata  acggcagcat   ccctcaccag   attcatctcg   gggagctgca   cgccatcctg   1320
agaaggcagg  aagacttcta   cccctttctt   aaggataacc   gggagaagat   cgaaaagatt   1380
ctgacgttca  gaattccgta   ctatgtcgga   ccactcgccc   ggggtaattc   cagatttgcg   1440
tggatgacca  gaaagagcga   ggaaaccatc   acaccttcgt   gaacttcgagga   agtggtcgat  1500
aagggcgctt  ccgcacagag   cttcattgag   cgcatgacaa   atttttgacaa   gaacctgcct   1560
aatgagaagg  tccttcccaa   gcattccctc   ctgtacgagt   atttcactgt   ttataacgaa   1620
ctcacgaagg  tgaagtatgt   gaccgaggga   atgcgcaagc   ccgccttcct   gagcggcgag   1680
caaaagaagg  cgatcgtgga   ccttttgttt   aagaccaatc   ggaaggtcac   agttaagcag   1740
ctcaaggagg  actacttcaa   gaagattgaa   tgcttcgatt   ccgttgagat   cagcggcgtg   1800
gaagacaggt  ttaacgcgtc   actgggcact   taccacgatc   tcctgaagat   cattaaggat   1860
aaggacttct  tggacaacga   ggaaaatgag   gatatcctcg   aagacattgt   cctgactctt   1920
acgttgtttg  aggataggga   aatgatcgag   gaacgcttga   agacgtatgc   ccatctcttc   1980
gatgacaagg  ttatgaagca   gctcaagaga   agaagataca   ccggatggg    aaggctgtcc   2040
cgcaagctta  tcaatggcat   tagagacaag   caatcaggga   agacaatcct   tgacttttg    2100
aagtctgatg  gcttcgcgaa   caggaatttt   atgcagctga   ttcacgatga   ctcacttact   2160
ttcaaggagg  atatccagaa   ggctcaagtc   tcggacaag    gtgacagtct   gcacgagcat   2220
atcgccaacc  ttgcgggatc   tcctgcaatc   aagaaggta   ttctgcagac   agtcaaggtt   2280
gtggatgagc  ttgtgaaggt   catgggacgg   cataagcccg   agaacatcgt   tattgagatg   2340
gccagagaaa  atcagaccac   acaaaagggt   cagaagaact   cgagggagcg   catgaagcgc   2400
atcgaggaag  gcattaagga   gctggggagt   cagatcctta   aggagcaccc   ggtgaaaac    2460
acgcagttgc  aaaatgaggc   cctctatctg   tactatctgc   aaaatggcag   ggatatgtat   2520
gtggaccagg  agttggatat   taaccgcctc   tcggattacg   acgtcgatca   tatcgttcct   2580
cagtccttcc  ttaaggatga   cagcattgac   aataaggttc   tcaccagtcg   cgacaagaac   2640
cgcggaagt   ccgataatgt   gcccagcgag   gaagtcgtta   agaagatgaa   gaactactgg   2700
aggcaacttt  tgaatgccaa   gttgatcaca   cagaggaagt   ttgataacct   cactaaggcc   2760
gagcgcggag  gtctcagcga   actggacaag   gcgggcttca   ttaagcggca   actggttgag   2820
actagacaga  tcacgaagca   cgtggcgcag   attctcgatt   cacgcatgaa   cacgaagtac   2880
gatgagaatg  acaagctgat   ccgggaagtg   aaggtcatca   ccttgaagtc   aaagctcgtt   2940
```

-continued

```
tctgacttca ggaaggattt ccaattttat aaggtgcgcg agatcaacaa ttatccaccat    3000
gctcatgacg cataccctcaa cgctgtggtc ggaacagcat tgattaagaa gtacccggcg    3060
ctcgagtccg aattcgtgta cggtgactat aaggtttacg atgtgcgcaa gatgatcgcc    3120
aagtcagagc aggaaattgg caaggccact gcgaagtatt tcttttactc taacattatg    3180
aatttcttta agactgagat cacgcctggct aatggcgaaa tccggaaggc gccacttatt    3240
gagaccaacg gcgagacagg ggaaatcgtg tgggacaagg ggagggattt cgccacagtc    3300
cgcaaggttc tctctatgcc tcaagtgaat attgtcaaga agactgaagt ccagacgggc    3360
gggttctcaa aggaatctat tctgcccaag cggaactcgg ataagcttat cgccagaaag    3420
aaggactggg acccgaagaa gtatggaggt ttcgactcac caacggtggc ttactctgtc    3480
ctggttgtgg caaaggtgga gaaggaaag tcaaagaagc tcaagtctgt caaggagctc    3540
ctgggtatca ccattatgga gaggtccagc ttcgaaaaga atccgatcga ttttctcgag    3600
gcgaagggat ataaggaagt gaagaaggac ctgatcatta agcttccaaa gtacagtctt    3660
ttcgagttgg aaaacggcag gaagcgcatg ttggcttccg caggagagct ccagaagggt    3720
aacgagctg ctttgccgtc caagtatgtg aacttcctct atctggccatc ccactacgag    3780
aagctcaagg gcagcccaga ggataacgaa cagaagcaac tgtttgtgga gcaacacaag    3840
cattatcttg acgagatcat tgaacagatt tcggagttca gtaagcgcgt catcctcgcc    3900
gacgcgaatt tggataaggt tctctcagcc tacaacaagc accgggacaa gcctatcaga    3960
gagcaggcgg aaaatatcat tcatctcttc accctgacaa accttgggc tcccgctgca    4020
ttcaagtatt ttgacactac gattgatcgg aagagataca cttctacgaa ggaggtgctg    4080
gatgcaaccc ttatccacca atcgattact ggcctctacg agacgcggat cgacttgagt    4140
cagctcgggg gggataagag accagcggca accaagaagg caggacaagc gaagaagaag    4200
aagtag                                                                4206
```

| SEQ ID NO: 8 | moltype = DNA length = 4206 |
|---|---|
| FEATURE | Location/Qualifiers |
| misc_feature | 1..4206 |
| | note = eSpCas9(1.1) codon-optimized nucleotide sequence |
| source | 1..4206 |
| | mol_type = other DNA |
| | organism = synthetic construct |

SEQUENCE: 8

```
atggcccta agaagaagag aaaggtcggt attcacggcg ttcctgcggc gatggacaag      60
aagtatagta ttggtctgga cattgggacg aattccgttg gctgggccgt gatcaccgat    120
gagtacaagg tcccttccaa gaagtttaag gttctgggga acaccgatcg gcacagcatc    180
aagaagaatc tcattgagc cctcctgttc gactcaggcg agaccgccga agcaacaagg    240
ctcaagagaa ccgcaaggag acggtataca agaaggaaga ataggatctg ctacctgcag    300
gagattttca gcaacgaaat ggcgaaggtg gacgattcgt tcttttcatag attggaggag    360
agtttcctcg tcgaggaaga taagaagcac gagaggcatc ctatctttgg caacattgtc    420
gacgaggttg cctatcacga aaagtacccc acaatctatc atctgcggaa gaagcttgtg    480
gactcgactg ataaggcgga ccttagattg atctacctcg ctctggcaca catgattaag    540
ttcaggggcc attttctgat cgaggggat cttaacccgg acaatagcga tgtggacaag    600
ttgttcatcc agctcgtcca aacctacaat cagctctttg aggaaacccc aattaatgct    660
tcaggcgtgc acgccaaggc gatcctgtct gcacgccttt caaagtctcg ccggcttgag    720
aacttgatcg ctcaactccc gggcgaaaag aagaacggct tgttcgggaa tctcattgca    780
cttttcgttgg ggctcacacc aaacttcaag agtaattttg atctcgctga ggacgcaaag    840
ctgcagcttt ccaaggacac ttatgacgat gacctggata ccttttggc ccaaatcggc    900
gatcagtacg cggacttgtt cctcgccgcg aagaatttgt cggacgcgat cctcctgagt    960
gatattctcc gcgtgaacac cgagattaca aaggcccgc tctcggcgag tatgatcaag   1020
cgctatgacg agcaccatca ggatctgacc cttttgaagg ctttggtccg gcagcaactc   1080
ccagagaagt acaaggaaat ctttcttgat caatccaaga acggctacgc tggttatatt   1140
gacggcggga catcgcagga ggaattctac aagtttatca agcaattct ggagaagatg   1200
gatggcacag aggaactcct ggtgaagctc aataggagg accttttgcg gaagcaaaga   1260
actttcgata acggcagcat ccctcaccag attcatctcg gggagctgca cgccatcctg   1320
agaaggcagg aagacttcta cccctttctt aaggataacc gggagaagat cgaaaagatt   1380
ctgacgttca gaattccgta ctatgtcgga ccactcgcc ggggtaattc cagatttgcg   1440
tggatgacca gaaagagcga ggaaaccatc acacccttgga acttcgagga agtggtcgat   1500
aagggcgctt ccgcacagag cttcattgag cgcatgacaa attttgacaa gaacctgcct   1560
aatgagaagg tccttcccaa gcattccctc ctgtacgagt atttcactgt ttataacgaa   1620
ctcacgaagg tgaagtatgt gaccgggga atgcgcaagc ccgcccttcct gagcggcgag   1680
caaaagaagg cgatcgtgga ccttttgttt aagaccaatc ggaaggtcac agttaagcag   1740
ctcaaggagg actacttcaa gaagattgaa tgcttcgatt ccgttgagat cagcggcgtg   1800
gaagacaggt taacgcgtc actgggact taccacgatc tcctgaagat cattaaggat   1860
aaggacttct ggacaacga ggaaatgag gatatcctcg aagacattgt cctgactctt   1920
acgttgtttg aggataggga aatgatcgag gaacgcttga acgctatgc ccatctcttc   1980
gatgacaagg ttatgaagca gctcaagaga agaagataca ccggatgggg aaggctgtcc   2040
cgcaagctta tcaatggcat tagagacaag caatcaggga agacaatcct tgactttttg   2100
aagtctgatg gcttcgcgaa caggaatttt atgcagctga tcacgatga ctcacttact   2160
ttcaaggagg atatccagaa ggctcaagtg tcggacaag gtgacagtct gcacgagcat   2220
atcgccaacc ttgcgggatc tcctgcaatc aagaaggta ttctgcagac agtcaaggtt   2280
gtggatgagc ttgtgaaggt catgggacgg cataagcccg agaacatcgt tattgagatg   2340
gccagagaaa atcagaccac acaaaagggt cagaagaact cgagggagcg catgaagcgc   2400
atcgaggaag gcattaagga gctggggagt cagatcctta aggagcaccc ggtggaaaac   2460
acgcagttgc aaaatgagaa gctctatctg tactatctgc aaaatgggag gcatatgtat   2520
gtggaccagg agttggatat taaccgcctc tcggattacg acgtgatca tatcgttcct   2580
cagtccttc tgcgatgaca gcattgac aataaggttc tcaccaggtc gacaagaac   2640
cgcgggaagt ccgataatgt gcccagcgag aagtcgtta agaagatgaa gaactactgg   2700
aggcaacttt tgaatgccaa gttgatcaca cagaggaagt tgataaccct cactaaggcc   2760
gagcgcggag gtctcagcga actggacaag gcgggcttcc ttaagcggca actggttgag   2820
actagacaga tcacgaagca cgtggcgcag attctcgatt cacgcatgaa cacgaagtac   2880
```

```
gatgagaatg acaagctgat ccgggaagtg aaggtcatca ccttgaagtc aaagctcgtt  2940
tctgacttca ggaaggattt ccaattttat aaggtgcgcg agatcaacaa ttatcaccat  3000
gctcatgacg catacctcaa cgctgtggtc ggaacagcat tgattaagaa gtacccggcg  3060
ctcgagtccg aattcgtgta cggtgactat aaggtttacg atgtgcgcaa gatgatcgcc  3120
aagtcagagc aggaaattgg caaggccact gcgaagtatt tcttttactc taacattatg  3180
aatttcttta agactgagat cacgctggct aatggcgaaa tccggaaggc gccacttatt  3240
gagaccaacg gcgagacagg ggaaatcgtg tgggacaagg ggagggattt cgccacagtc  3300
cgcaaggttc tctctatgcc tcaagtgaat attgtcaaga agactgaagt ccagacgggc  3360
gggttctcaa aggaatctat tctgcccaag cggaactgga ataagcttat cgccagaaag  3420
aaggactggg acccgaagaa gtatgggaggt ttcgactcac caacggtggc ttactctgtc  3480
ctggttgtgg caaggtgga aagggaaag tcaagaagc tcaagtctgt caaggagctc  3540
ctgggtatca ccattatgga gaggtccagc ttcgaaaaga atccgatcga ttttctcgag  3600
gcgaagggat ataaggaagt gaagaaggac ctgatcatta agctccaaa gtacagtctt  3660
ttcgagttgg aaaacggcag gaagcgcatg ttggcttccg caggagagct ccagaaggt  3720
aacgagcttg ctttgccgtc caagtatgtg aacttcctct atctggcatc ccactacgag  3780
aagctcaagg gcagcccaga ggataacgaa cagaagcaac tgtttgtgga gcaacacaag  3840
cattatcttg acgagatcat tgaacagatt tcggagttca gtaagcgcgt catcctcgcc  3900
gacgcgaatt tggataaggt tctctcagcc tacaacagga ccggacaa gcctatcaga  3960
gagcaggcgg aaaatatcat tcatctcttc accctgacaa accttgggggc tcccgctgca  4020
ttcaagtatt tgacactac gattgatcgg aagagataca cttctacgaa ggagggtgctg  4080
gatgcaaccc ttatccacca atcgattact ggcctctacg acgcgcggat cgacttgagt  4140
cagctcgggg gggataaagag accagcggca accaagaagg caggacaagc gaagaagaag  4200
aagtag                                                             4206

SEQ ID NO: 9       moltype = DNA  length = 4206
FEATURE            Location/Qualifiers
misc_feature       1..4206
                   note = SpCas9-HF1 codon-optimized nucleotide sequence
source             1..4206
                   mol_type = other DNA
                   organism = synthetic construct
SEQUENCE: 9
atggccccta agaagaagag aaaggtcggt attcacggcg ttcctgcggc gatggacaag  60
aagtatagta ttggtctgga cattgggacg aattccgttg gctgggccgt gatcaccgat  120
gagtacaagg tcccttccaa gaagtttaag gttctgggga acaccgatcg gcacagcatc  180
aagaagaatc tcattggagc cctcctgttc gactcaggcg agaccgccga agcaacaagg  240
ctcaagagaa ccgcaaggag acggtataca agaaggaaga ataggatctg ctacctgcag  300
gagattttca gcaacgaaat ggcgaaggtg gacgattcgt tctttcatag attggaggag  360
agtttcctcg tcgaggaaga taagaagcac gagaggcatc ctatctttgg caacattgtc  420
gacgaggttg cctatcacga aaagtacccc acaatctatc atctgcggaa gaagcttgtg  480
gactcgactg ataaggcgga ccttagattg atctaccttcg ctctggcaca catgattaag  540
ttcagggggcc attttctgat cgaggggat cttaacccgg acaatagcga tgtggacaag  600
ttgttcatcc agctcgttca aacctacaat cagctctttg aggaaaaccc aattaatgct  660
tcaggcgtcg acgccaaggc gatcctgtct gcacgccttt caaagtctcg ccggcttgag  720
aacttgatcg ctcaactccc gggcgaaaag aagaacggct tgttcggaaa tctcattgca  780
cttttcgttg ggctcacacc aaacttcaag agtaattttg atctcgctga ggacgcaaag  840
ctgcagcttt ccaaggacac ttatgacgat gacctggata accttttggc ccaaatcggc  900
gatcagtacg cggacttgtt cctcgccgcg aagaatttgt cggacgcgat cctcctgagt  960
gatattctcc gcgtgaacac cgagattaca aaggcccccg ctctcggcga tatgatcaag  1020
cgctatgacg agcaccatca ggatctgacc cttttgaagg ctttggtccg gcagcaactc  1080
ccagagaagt acaaggaaat ctttttgat caatccacga acgctacgc tggttatatt  1140
gacggcgggg catcgcagga ggaattctac aagtttatca gccaattct ggagaagatg  1200
gatggcacag aggaactcct ggtgaagctc aataggagg acctttttgcg gaagcaaaga  1260
actttcgata cggcagcat ccctcaccag attcatctcg gggagctgca cgccatcctg  1320
agaaggcagg aagacttcta ccccttttctt aaggataacc gagaaagatt cgaaaagatt  1380
ctgacgttca aattccgta ctatgtcgga ccactcgccc ggggtaattc cagatttgcg  1440
tggatgacca gaaagagcga ggaaaccatc acaccttgga acttcgagga agtggtcgat  1500
aagggcgctt ccgcacagag cttcattgag cgcatgacag cctttgacaa gaaccctgcc  1560
aatgagaagg tccttccaa gcattccctc tgtgtacgag atttcactgt ttataacgaa  1620
ctcacgaagg tgaagtatgt gaccgaggga atgcgcaagc cgccttcct gagcggcgag  1680
caaaagaagg cgatcgtgga ccttttgttt aagaccaatc ggaaggtcac agttaagcag  1740
ctcaaggagg actacttcaa gaagattgaa tgcttcgatt ccgttgagat cagcggcgtg  1800
gaagacaggt taacgcgtc actggggact taccacgatc tcctgaagat cattaaggat  1860
aaggacttct tggacaacga ggaaaatgag gatatctcg aagacattgt cctgactctt  1920
acgttgtttg aggataggga atgatcgag gaacgcttga gacgtatgc catctcttc  1980
gatgacaagg ttatgaagca gctcaagaga aaagatacca ccggatgggg agccctgtcc  2040
cgcaagctta tcaatggcat tagagacaag caatcaggga gacaatcct tgacttttttg  2100
aagtctgatg gcttcgcgaa caggaatttt atggcccgta ttcacgatga ctcacttact  2160
ttcaaggaga tatccagaa ggctcaagtg tcgggacaag gtgacagtct gcacgagcat  2220
atcgccaacc ttgcgggatc tcctgcaatc aagaagggta ttctgcagac agtcaaggtt  2280
gtggatgagc ttgtgaaggt catgggacgg cataagcccg agaacatcgt tattgagatg  2340
gccagagaaa atcagaccac acaaaagggt cagaagaact cgagggagcg catgaagcgc  2400
atcgaggaag gcattaagga gctggggagt cagatcctta aggagcaccc ggtggaaaac  2460
acgcagttgc aaaatgagaa gctctatctg tactatctgc aaaatggag ggatatgtat  2520
gtggaccagg agttggatat taaccgcctc tcggattacg acgtcgatca tatcgttcct  2580
cagtccttcc ttaaggatga cagcattgac aataaggttc tcaccaggtc cgacaagaac  2640
cgcgggaagt ccgataatgt gcccagcgag gaagtcgtta agaagatgaa gaactactgg  2700
aggcaacttt tgaatgccaa gttgatcaca cagaggaagt ttgataacct cactaaggcc  2760
gagcgcggag gtctcagcga actggacaag gcgggcttca ttaagcggca actggttgag  2820
```

-continued

```
actagagcca tcacgaagca cgtggcgcag attctcgatt cacgcatgaa cacgaagtac   2880
gatgagaatg acaagctgat ccgggaagtg aaggtcatca ccttgaagtc aaagctcgtt   2940
tctgacttca ggaaggattt ccaatttat aaggtgcgcg agatcaacaa ttatcaccat    3000
gctcatgacg catacctcaa cgctgtggtc ggaacagcat tgattaagaa gtacccgaag   3060
ctcgagtccg aattcgtgta cggtgactat aaggtttacg atgtgcgcaa gatgatcgcc   3120
aagtcagagc aggaaattgg caaggccact gcgaagtatt tcttttactc taacattatg   3180
aatttcttta agactgagat cacgctggct aatggcgaaa tccggaagag accacttatt   3240
gagaccaacg gcgagacagg ggaaatcgtg tgggacaagg ggagggattt cgccacagtc   3300
cgcaaggttc tctctatgcc tcaagtgaat attgtcaaga agctgaagt ccagacgggc    3360
gggttctcaa aggaatctat tctgcccaag cggaactcgg ataagcttat cgccagaaag   3420
aaggactggg acccgaagaa gtatggaggt ttcgactcac caacggtggc ttactctgtc   3480
ctggttgtgg caaaggtgga aagggaaag tcaaagaagc tcaagtctgt caaggagctc    3540
ctgggtatca ccattatgga gaggtccagc ttcgaaaaga atccgatcga ttttctcgag   3600
gcgaagggat ataaggaagt gaagaaggac ctgatcatta gcttccaaa gtacagtctt    3660
ttcgagttgg aaaacggcag gaagcgcatg ttggcttccg caggagagct ccagaagggt   3720
aacgagcttg ctttgccgtc caagtatgtg aacttcctct atctggcatc ccactacgag   3780
aagctcaagg gcagcccaga ggataacgaa cagaagcaac tgtttgtgga gcaacacaag   3840
cattatcttg acgagatcat tgaacagatt tcggagttca gtaagcgcgt catcctcgcc   3900
gacgcgaatt tggataaggt tctctcagcc tacaacaagc accgggacaa gcctatcaga   3960
gagcaggcgg aaaatatcat tcatctcttc accctgacaa accttgggc tcccgctgca    4020
ttcaagtatt tgacactac gattgatcgg aagagataca cttctacgaa ggaggtgctg     4080
gatgcaaccc ttatccacca atcgattact ggcctctacg agacgcggat cgacttgagt   4140
cagctcgggg gggataagag accagcggca accaagaagg caggacaagc gaagaagaag   4200
aagtag                                                              4206

SEQ ID NO: 10            moltype = DNA  length = 9182
FEATURE                  Location/Qualifiers
misc_feature             1..9182
                         note = pJIT163-SpCas9 vector sequence
source                   1..9182
                         mol_type = other DNA
                         organism = synthetic construct SEQUENCE: 10
gagctcggta cctgacccgg tcgtgcccct ctctagagat aatgagcatt gcatgtctaa    60
gttataaaaa attaccacat atttttttg tcacacttgt ttgaagtgca gtttatctat     120
ctttatacat atatttaaac tttactctac gaataatata atctatagta ctacaataat    180
atcagtgttt tagagaatca tataaatgaa cagttagaca tggtctaaag gacaattgag   240
tatttttgaca acaggactct acagttttat ctttttagtg tgcatgtgtt ctccttttt   300
tttgcaaata gcttcaccta tataatactt catccatttt attagtacat ccatttaggg   360
tttagggtta atggttttta tagactaatt ttttttagtac atctatttta ttctatttta   420
gcctctaaat taagaaaact aaaactctat tttagttttt ttatttaata atttagatat   480
aaaatagaat aaaataaagt gactaaaaat taaacaaata ccctttaaga aattaaaaaa   540
actaaggaaa cattttttctt gttcgagta gataatgcca gcctgttaaa cgccgtcgac   600
gagtctaacg acaccaacc agcgaaccag cagcgtcgcg tcgggccaag cgaagcagac    660
ggcacggcat ctctgtcgct gcctctggac ccctctcgat cgagagttcc gctccaccgt    720
tggacttgct ccgctgtcgg catccagaaa ttgcgtggcg gagcggcaga cgtgagccgg    780
cacggcaggc ggcctcctcc tcctctcacg gcaccggcag ctacggggga ttccttccc    840
accgctcctt cgctttccct tcctcgcccg ccgtaataaa tagacaccc ctccacaccc      900
tcttttcccca acctcgtgtt gttcggagcg cacacacaca caaccagatc tcccccaaat   960
ccaccgtcg gcacctccgc ttcaaggtac gccgctcgtc ctcccccccc cccctctct     1020
accttctcta gatcggcgtt ccggtccatg gttaggcc ggtagttcta cttcctgtca    1080
tgtttgtgtt agatccgtgt ttgtgttaga tccgtgctgc tagcgttcgt acacggatgc    1140
gacctgtacg tcagacacgt tctgattgct aacttgccag tgtttctctt tggggaatcc    1200
tgggatggcc ctagccgttc cgcagacggg atcgatttca tgattttttt tgtttcgttg    1260
catagggttt ggttttgccct tttccttttat ttcaatatat gccgtgcact tgtttcgcgg   1320
gtcatctttt catgcttttt tttgtcttgg ttgtgatgat gtggtctggt tgggcggtcg    1380
ttctagatcg gagtagaatt aattctgttt caaactacct ggtggattta ttaatttgg    1440
atctgtatgt gtgtgccata catattcata gttacgaatt gaagatgatg gatgcaaata    1500
tcgatctagg ataggtatac atgttgatgc gggttttact gatgcatata cagagatgtt   1560
ttttgttcgc ttggttgtga tgatgtggtg tggttgggcg tcgttcatt cgttctagat    1620
cggagtagaa tactgtttca aactacctgg tgtatttatt aattttggaa ctgtatgtgt    1680
gtgtcataca tcttcatagt tacgagttta agatggatgg aaatatcgat ctaggatagg   1740
tatacatgtt gatgtgggtt ttactgatgc atatacatga tggcatatgc agcatctatt   1800
catatgctct aaccttgagt acctatctat tataataaac aagtatgttt tataattatt    1860
ttgatcttga tatacttgga tgatggcata tgcagcagct atatgtggat ttttttagcc    1920
ctgccttcat acgctatttta tttgcttggt actgtttctt ttgtcgatgc tcaccctgtt   1980
gtttggtgtt acttctgcaa agcttccacc atggcgtgca ggtcgactct agaggatccc    2040
catggcccct aagaagaaga gaaaggtcgg tattcacgga gttcctgcgg cgatggacaa    2100
gaagtatagt attggtctgg acattgggac gaattccgtg ggctggcggt tgatcaccga    2160
tgagtacaag gtcccttcca agaagtttaa ggttctgggg aacaccgatc ggcacagcat    2220
caagaagaat ctcattggag ccctcctgtt cgactcaggc gagaccgccg aagcaacaag    2280
gctcaagaga accgcaagga cggtatac aagaaggaag ataggatct gctacctgca       2340
ggagatttc agcaacgaaa tggcgaaggt ggacgattcg ttctttcata gattggagga    2400
gagttttccc gtcgaggaag ataagaagca cgagagcgat cctatctttg gcaacattgt    2460
cgacgaggtt gcctatcacg aaaagtaccc cacaatctat catctgcgga agaagcttgt    2520
ggactcgact gataaggcgg accttagatt gatctacctc gctctggcac acatgattaa    2580
gttcagggc cattttctga tcgaggggga tcttaacccg acaatagcg atgtggacaa     2640
gttgttcatc cagctcgtcc aaacctacaa tcagctcttt gaggaaaacc caattaatgc    2700
ttcaggcgtc gacgccaagg cgatcctgtc tgcacgcctt tcaaagtctc gccggcttga    2760
```

```
gaacttgatc gctcaactcc cgggcgaaaa gaagaacggc ttgttcggga atctcattgc  2820
actttcgttg gggctcacac caaacttcaa gagtaatttt gatctcgctg aggacgcaaa  2880
gctgcagctt tccaaggaca cttatgacga tgacctggat aaccttttgg cccaaatcgg  2940
cgatcagtac gcggacttgt tcctcgccgc gaagaatttg tcggacgcga tcctcctgag  3000
tgatattctc cgcgtgaaca ccgagattac aaaggcccg ctctcggcga gtatgatcaa  3060
gcgctatgac gagcaccatc aggatctgac ccttttgaag gctttggtcc ggcagcaact  3120
cccagagaag tacaaggaaa tcttctttga tcaatccaag aacggctacg ctggttatat  3180
tgacggcggg gcatcgcagg aggaattcta caagtttatc aagccaattc tggagaagat  3240
ggatggcaca gaggaactcc tggtgaagct caatagggag gaccttttgc ggaagcaaag  3300
aactttcgat aacggcagca tccctcacca gattcatcct ggggagctgc acgccatcct  3360
gagaaggcag gaagacttct accccttttct taaggataac cgggagaaga tcgaaaagat  3420
tctgacgttc agaattccgt actatgtcgg accactcgcc cggggtaatt ccagatttgc  3480
gtggatgacc agaaagagcg aggaaaccat cacaccttgg aacttcgagg aagtggtcga  3540
taagggcgct tccgcacaga gcttcattga gcgcatgaca aattttgaca agaacctgcc  3600
taatgagaag gtccttccca agcattccct cctgtacgag tatttcactg tttataacga  3660
actcacgaag gtgaagtatg tgaccgaggg aatgcgcaag cccgccttcc tgagcggcga  3720
gcaaaagaag gcgatcgtgg accttttgtt taagaccaat cggaaggtca cagttaagca  3780
gctcaaggag gactacttca agaagattga atgcttcgat tccgttgaga tcagcggcga  3840
ggaagacagg tttaacgcgt cactggggac ttaccacgac ctcctgaaga tcattaagga  3900
taaggacttc ttggacaacg aggaaaatga ggatatcctc gaagacattg tcctgactct  3960
tacgttgttt gaggataggg aaatgatcga ggaacgcttg aagacgtatg cccatctctt  4020
cgatgacaag gttatgaagc agctcaaggag aagaagatac accggatggg gaaggctgtc  4080
ccgcaagctt atcaatggca ttagagacaa gcaatcaggg aagacaatcc ttgacttttt  4140
gaagtctgat ggcttcgcga acaggaattt tatgcagctg attcacgatg actcacttac  4200
tttcaaggag gatatccaga aggctcaagt gtcgggacaa ggtgacagtc tgcacgagca  4260
tatcgccaac cttgcgggat ctcctgcaat caagaaggt attctgcaga cagtcaaggt  4320
tgtggatgag cttgtgaagg tcatgggacg gcataagccc gagaacatcg ttattgagat  4380
ggccagagaa aatcagacca cacaaaaggg tcagaagaac tcgagggagc gcatgaagcg  4440
catcgaggaa ggcattaagg agctggggag tcagatcctt aaggagcacc cggtggaaaa  4500
cacgcagttg caaaatgaga agctctatct gtactatctg caaaatggca gggatatgta  4560
tgtggaccag gagttggata ttaaccgcct ctcggattac gacgtcgatc atatcgttcc  4620
tcagtccttc cttaaggatg acagcattga caataaggtt ctcaccaggt ccgacaagaa  4680
ccgcgggaag tccgataatg tgcccagcga ggaagtcgtt aagaagatga gaactactg  4740
gaggcaactt ttgaatgcca cagttgatca acagaggaag tttgataacc tcactaaggc  4800
cgagcgcgga ggtctcagcg aactggacaa ggcgggcttc attaagcggc aactggttga  4860
gactagacag atcacgaagc acgtggcgca gattctcgat tcacgcatga acacgaagta  4920
cgatgagaat gacaagctga tccgggaagt gaaggtcatc accttgaagt caaagctcgt  4980
ttctgacttc aggaaggatt tccaatttta taaggtgcgc gagatcaaca attatcacca  5040
tgctcatgac gcatacctca acgctgtggt cggaacagtc ttgattaaga agtacccgaa  5100
gctcgagtcc gaattcgtgt acggtgacta aaggtttac gatgtgcgca agatgatcgc  5160
caagtcagag caggaaattg gcaaggccac tgcgaagtat ttctttttact ctaacattat  5220
gaatttcttt aagactgaga tcacgctggc taatggcgaa atccggaaga gaccactat  5280
tgagaccaac ggcgagacag gggaaatcgt gtgggacaag gggagggatt tcgccacagt  5340
ccgcaaggtt ctctctatgc ctcaagtgaa tattgtcaag aagactgaag tccagacggg  5400
cgggttctca aaggaatcta ttctgcccaa gcggaactcg gataagctta tcgccagaaa  5460
gaaggactgg gacccgaaga agtatggagg tttcgactca ccaacggtgg cttactctgt  5520
cctggttgtg gcaaaggtgg agaagggaaa gtcaaagaag ctcaagtctg tcaaggagct  5580
cctgggtatc accattatgg agaggtccag cttcgaaaag aatccgatcg attttctcga  5640
ggcgaaggga tataaggaag tgaagaagga cctgatcatt aagcttccaa agtacagtct  5700
tttcgagttg gaaaacggca ggaagcgcat gttggcttcc gcaggagagc tccagaaggg  5760
taacgcgcgcttt gctttgccgt ccaagtatgt gaacttcctc tatctggcat cccactacga  5820
gaagctcaag ggcagcccag aggataacga acagaagcaa ctgtttgtgg agcaacacaa  5880
gcattatctt gacgagatca ttgaacagat ttcggagttc agtaagcgcg tcatcctcgc  5940
cgacgcgaat ttgataagg ttctctcagc ctacaacaag caccgggaca agcctatcag  6000
agagcaggcg gaaaatatca ttcatctctt caccctgaca aaccttgggg ctcccgctgc  6060
attcaagtat tttgcactac gattgatcg gaagagatac acttctacga aggaggtgct  6120
ggatgcaacc cttatccacc aatcgattac tggcctctac gagacgcgga tcgacttgag  6180
tcagctcggg gggataaga gaccagcggc aaccaagaag gcaggacaag cgaagaagaa  6240
gaagtagggg cgagctcgaa ttcgctgaaa tcaccagtct ctctctacaa atctatctct  6300
ctctattttc tccataaata atgtgtgagt agtttcccga taaggggaat taggggttctt  6360
atagggtttc gctcatgtgt tgagcatata agaaaccctt agtatgtatt tgtatttgta  6420
aaatacttct atcaataaaa tttctaattc ctaaaaccaa aatccagtac taaaatccag  6480
atctcctaaa gtccctatag atctttgtcg tgaatataaa ccagacacga gacgactaaa  6540
cctggagccc agacgccgtt cgaagctaga agtaccgctt aggcaggagg ccgttaggga  6600
aaagatgcta aggcagggtt ggttacgttg actccccgt aggtttggtt taaatatgat  6660
gaagtggacg gaaggaagga ggaagacaag gaaggataag gttcaggcc ctgtgcaagg  6720
taagaagatg gaaatttgat agaggtacgc tactatactt atactatacg ctaagggaat  6780
gcttgtattt atacctata ccccctaata ccccttatc aatttaagaa ataatccgtca  6840
taagccccg cttaaaaatt ggtatcagag ccatgaatag gtctatgacc aaaactcaag  6900
aggataaaac ctcaccaaaa tacgaaagag ttcttaactc taaagataaa agatctttca  6960
agatcaaaac tagttccctc acaccggagc atgcgatatc ctcgagagat ctaggcgtaa  7020
tcatggtcat agctgtttcc tgtgtgaaat tgttatccgc tcacaattcc acacaacata  7080
cgagccggaa gcataaagtg taaagcctgg ggtgcctaat gagtgagcta actcacatta  7140
attgcgttgc gctcactgcc cgctttccag tcgggaaacc tgtcgtgcca gctgcattaa  7200
tgaatcggcc aacgcgcggg gagaggcggt ttgcgtattg ggcgctcttc cgcttcctcg  7260
ctcactgact cgctgcgctc ggtcgttcgg ctgcggcgag cggtatcagc tcactcaaag  7320
gcggtaatac ggttatccac agaatcaggg gataacgcag gaaagaacat gtgagcaaaa  7380
ggccagcaaa aggccaggaa ccgtaaaaag gccgcgttgc tggcgttttt ccataggctc  7440
cgccccctg acgagcatca caaaaatcga cgctcaagtc agaggtggcg aaacccgaca  7500
```

```
ggactataaa gataccaggc gtttcccccT ggaagctccc tcgtgcgctc tcctgttccg   7560
accctgccgc ttaccggata cctgtccgcc tttctccctt cgggaagcgt ggcgctttct   7620
caatgctcac gctgtaggta tctcagttcg gtgtaggtcg ttcgctccaa gctgggctgt   7680
gtgcacgaac cccccgttca gcccgaccgc tgcgccttat ccggtaacta tcgtcttgag   7740
tccaacccgg taagacacga cttatcgcca ctggcagcca ccactggtaa caggattagc   7800
agagcgaggt atgtaggcgg tgctacagag ttcttgaagt ggtggcctaa ctacggctac   7860
actagaagga cagtatttgg tatctgcgct ctgctgaagc cagttacctt cggaaaaaga   7920
gttggtagct cttgatccgg caaacaaacc accgctggta gcggtggttt ttttgtttgc   7980
aagcagatta ttacgcgcag aaaaaaagga tctcaagaag atcctttgat cttttctacg   8040
gggtctgacg ctcagtggaa cgaaaactca cgttaaggga ttttggtcat gagattatca   8100
aaaaggatct tcacctagat ccttttaaat taaaaatgaa gttttaaatc aatctaaagt   8160
atatatgagt aaacttggtc tgacagttac caatgcttaa tcagtgaggc acctatctca   8220
gcgatctgtc tatttcgttc atccatagtt gcctgactcc ccgtcgtgta gataactacg   8280
atacgggagg gcttaccatc tggccccagt gctgcaatga taccgcgaga cccacgctca   8340
ccggctccag atttatcagc aataaaccag ccagccggaa gggccgagcg cagaagtggt   8400
cctgcaactt tatccgcctc catccagtct attaattgtt gccgggaagc tagagtaagt   8460
agttcgccag ttaatagttt gcgcaacgtt gttgccattg ctacaggcat cgtggtgtca   8520
cgctcgtcgt ttggtatggc ttcattcagc tccggttccc aacgatcaag gcgagttaca   8580
tgatccccca tgttgtgcaa aaaagcggtt agctccttcg gtcctccgat cgttgtcaga   8640
agtaagttgg ccgcagtgtt atcactcatg gttatggcag cactgcataa ttctcttact   8700
gtcatgccat ccgtaagatg cttttctgtg actggtgagt actcaaccaa gtcattctga   8760
gaatagtgta tgcggcgacc gagttgctct gcccggcgtc caatacggga taataccgcg   8820
ccacatagca gaactttaaa agtgctcatc attggaaaac gttcttcggg gcgaaaactc   8880
tcaaggatct taccgctgtt gagatccagt tcgatgtaac ccactcgtgc acccaactga   8940
tcttcagcat cttttacttt caccagcgtt tctgggtgag caaaaacagg aaggcaaaat   9000
gccgcaaaaa agggaataag ggcgacacgg aaatgttgaa tactcatact cttccttttt   9060
caatattatt gaagcattta tcagggttat tgtctcatga gcggatacat atttgaatgt   9120
atttagaaaa ataaacaaat aggggttccg cgcacatttc cccgaaaagt gccacctgac   9180
gt                                                                 9182

SEQ ID NO: 11          moltype = DNA   length = 3243
FEATURE                Location/Qualifiers
misc_feature           1..3243
                       note = pUC57-U3-tRNA-sgRNA vector sequence
source                 1..3243
                       mol_type = other DNA
                       organism = synthetic construct
SEQUENCE: 11
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg   120
ttggcgggtg tcgggctggc ttaactatgc ggcatcagag cagattgta ctgagagtgc    180
accagatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgcctg caggtcgacg attaaggaat   420
cttttaaacat cgaacagat cacttaaagt tcttctgaag caacttaaag ttatcaggca   480
tgcatggatc ttggaggaat cagatgtgca gtcagggacc atagcacaag acaggcgtct   540
tctactggtg ctaccagcaa atgctggaag ccgggaacac tgggtacgtc ggaaaccacg   600
tgatgtgaag aagtaagata aactgtagga gaaaagcatt tcgtagtggg ccatgaagcc   660
tttcaggaca tgtattgcag tatgggccgg cccattacgc aattggacga caacaaagac   720
tagtattagt accacctcgg ctatccacat agatcaaagc tgatttaaaa gagttgtgca   780
gatgatccgt ggcaacaaag caccagtggt ctagtggtag aatagtaccc tgccacggta   840
cagacccggg ttcgattccc ggctggtgca agagaccgat atcccatggc tcgagggtct   900
cggttttaga gctagaaata gcaagttaaa ataaggctag tccgttatca acttgaaaaa   960
gtggcaccga gtcggtgctt ttttttccaca taatctctag aggatccccg gcgtaatcat   1020
ggtcatagct gtttcctgtg tgaaattgtt atccgctcac aattccacac aacatacgag   1080
ccggaagcat aaagtgtaaa gcctggggtg cctaatgagt gagctaactc acattaattg   1140
cgttgcgctc actgcccgct ttccagtcgg gaaacctgtc gtgccagctg cattaatgaa   1200
tcggccaacg cgcggggaga ggcggtttgc gtattgggcg ctcttccgct tcctcgctca   1260
ctgactcgct gcgctcggtc gttcggctgc ggcgagcggt atcagctcac tcaaaggcgg   1320
taatacggtt atccacagaa tcaggggata acgcaggaaa gaacatgtga gcaaaaggcc   1380
agcaaaaggc caggaaccgt aaaaaggccg cgttgctggc gtttttccat aggctccgcc   1440
cccctgacga gcatcacaaa aatcgacgct caagtcagag gtggcgaaac ccgacaggac   1500
tataaagata ccaggcgttt ccccctggaa gctccctcgt gcgctctcct gttccgaccc   1560
tgccgcttac cggatacctg tccgcctttc tcccttcggg aagcgtggcg ctttctcata   1620
gctcacgctg taggtatctc agttcggtgt aggtcgttcg ctccaagctg ggctgtgtgc   1680
acgaaccccc cgttcagccc gaccgctgcg ccttatccgg taactatcgt cttgagtcca   1740
acccggtaag acacgactta tcgccactgg cagcagccac tggtaacagg attagcagag   1800
cgaggtatgt aggcggtgct acagagttct tgaagtggtg gcctaactac ggctacacta   1860
gaagaacagt atttggtatc tgcgctctgc tgaagccagt taccttcgga aaaagagttg   1920
gtagctcttg atccggcaaa caaaccaccg ctggtagcgg tggtttttt gtttgcaagc   1980
agcagattac gcgcagaaaa aaaggatctc aagaagatcc tttgatcttt tctacggggt   2040
ctgacgctca gtggaacgaa aactcacgtt aagggatttt ggtcatgaga ttatcaaaaa   2100
ggatcttcac ctagatcctt ttaaattaaa aatgaagttt taaatcaatc taaagtatat   2160
atgagtaaac ttggtctgac agttaccaat gcttaatcag tgaggcacct atctcagcga   2220
tctgtctatt tcgttcatcc atagttgcct gactccccgt cgtgtagata actacgatac   2280
gggagggctt accatctggc cccagtgctg caatgatacc gcgactccca cgctcaccgg   2340
ctccagattt atcagcaata aaccagccag ccggaagggc cgagcgcaga gtggtcctg   2400
caactttatc gcctccatc cagtctatta attgttgccg ggaagctaga gtaagtagtt   2460
```

```
cgccagttaa tagtttgcgc aacgttgttg ccattgctac aggcatcgtg gtgtcacgct   2520
cgtcgtttgg tatggcttca ttcagctccg gttcccaacg atcaaggcga gttacatgat   2580
cccccatgtt gtgcaaaaaa gcggttagct ccttcggtcc tccgatcgtt gtcagaagta   2640
agttggccgc agtgttatca ctcatggtta tggcagcact gcataattct cttactgtca   2700
tgccatccgt aagatgcttt tctgtgactg gtgagtactc aaccaagtca ttctgagaat   2760
agtgtatgcg gcgaccgagt tgctcttgcc cggcgtcaat acgggataat accgcgccac   2820
atagcagaac tttaaaagtg ctcatcattg gaaaacgttc ttcggggcga aaactctcaa   2880
ggatcttacc gctgttgaga tccagttcga tgtaacccac tcgtgcaccc aactgatctt   2940
cagcatcttt tactttcacc agcgtttctg ggtgagcaaa aacaggaagg caaaatgccg   3000
caaaaaaggg aataagggcg acacggaaat gttgaatact catactcttc ctttttcaat   3060
attattgaag catttatcag ggttattgtc tcatgagcgg atacatattt gaatgtattt   3120
agaaaaataa acaaataggg gttccgcgca catttccccg aaaagtgcca cctgacgtct   3180
aagaaaccat tattatcatg acattaacct ataaaaatag gcgtatcacg aggccctttc   3240
gtc                                                                3243

SEQ ID NO: 12          moltype = DNA   length = 43
FEATURE                Location/Qualifiers
misc_feature           1..43
                       note = sequence of 5' end ribozyme
misc_feature           1..6
                       note = n is a, c, g, or t
source                 1..43
                       mol_type = other DNA
                       organism = synthetic construct
SEQUENCE: 12
nnnnnnctga tgagtccgtg aggacgaaac gagtaagctc gtc                    43

SEQ ID NO: 13          moltype = DNA   length = 68
FEATURE                Location/Qualifiers
misc_feature           1..68
                       note = sequence of 3' end ribozyme
source                 1..68
                       mol_type = other DNA
                       organism = synthetic construct
SEQUENCE: 13
ggccggcatg gtcccagcct cctcgctggc gccggctggg caacatgctt cggcatggcg   60
aatgggac                                                            68

SEQ ID NO: 14          moltype = DNA   length = 15
FEATURE                Location/Qualifiers
misc_feature           1..15
                       note = NLS sequence
source                 1..15
                       mol_type = other DNA
                       organism = synthetic construct
SEQUENCE: 14
aagaagagaa aggtc                                                   15

SEQ ID NO: 15          moltype = DNA   length = 21
FEATURE                Location/Qualifiers
misc_feature           1..21
                       note = NLS sequence
source                 1..21
                       mol_type = other DNA
                       organism = synthetic construct
SEQUENCE: 15
cccaagaaga agaggaaggt g                                            21

SEQ ID NO: 16          moltype = DNA   length = 21
FEATURE                Location/Qualifiers
misc_feature           1..21
                       note = NLS sequence
source                 1..21
                       mol_type = other DNA
                       organism = synthetic construct
SEQUENCE: 16
ccaaagaaga agaggaaggt t                                            21

SEQ ID NO: 17          moltype = AA    length = 11
FEATURE                Location/Qualifiers
REGION                 1..11
                       note = NLS sequence
source                 1..11
                       mol_type = protein
                       organism = synthetic construct
SEQUENCE: 17
SGGSPKKKRK V                                                       11

SEQ ID NO: 18          moltype = DNA   length = 33
```

-continued

```
FEATURE              Location/Qualifiers
misc_feature         1..33
                     note = NLS sequence
source               1..33
                     mol_type = other DNA
                     organism = synthetic construct
SEQUENCE: 18
tcggggggga gcccaaagaa gaagcggaag gtg                                    33

SEQ ID NO: 19        moltype = AA  length = 7
FEATURE              Location/Qualifiers
REGION               1..7
                     note = NLS sequence
source               1..7
                     mol_type = protein
                     organism = synthetic construct
SEQUENCE: 19
PKKKRKV                                                                  7

SEQ ID NO: 20        moltype = DNA  length = 23
FEATURE              Location/Qualifiers
source               1..23
                     mol_type = other DNA
                     organism = Oryza sativa
SEQUENCE: 20
aggtcgggga ggggacgtac ggg                                               23

SEQ ID NO: 21        moltype = DNA  length = 24
FEATURE              Location/Qualifiers
misc_feature         1..24
                     note = sgRNA target sequence
source               1..24
                     mol_type = other DNA
                     organism = synthetic construct
SEQUENCE: 21
ggcaaggtcg gggaggggac gtac                                              24

SEQ ID NO: 22        moltype = DNA  length = 24
FEATURE              Location/Qualifiers
misc_feature         1..24
                     note = sgRNA target sequence
source               1..24
                     mol_type = other DNA
                     organism = synthetic construct
SEQUENCE: 22
aaacgtacgt cccctccccg acct                                              24

SEQ ID NO: 23        moltype = DNA  length = 23
FEATURE              Location/Qualifiers
source               1..23
                     mol_type = other DNA
                     organism = Oryza sativa
SEQUENCE: 23
gacgtcggcg aggaaggcct cgg                                               23

SEQ ID NO: 24        moltype = DNA  length = 24
FEATURE              Location/Qualifiers
misc_feature         1..24
                     note = sgRNA target sequence
source               1..24
                     mol_type = other DNA
                     organism = synthetic construct
SEQUENCE: 24
ggcagacgtc ggcgaggaag gcct                                              24

SEQ ID NO: 25        moltype = DNA  length = 24
FEATURE              Location/Qualifiers
misc_feature         1..24
                     note = sgRNA target sequence
source               1..24
                     mol_type = other DNA
                     organism = synthetic construct
SEQUENCE: 25
aaacaggcct tcctcgccga cgtc                                              24

SEQ ID NO: 26        moltype = DNA  length = 23
FEATURE              Location/Qualifiers
misc_feature         1..23
                     note = sgRNA target sequence
```

```
source                  1..23
                        mol_type = other DNA
                        organism = synthetic construct
SEQUENCE: 26
catggtgggg aaagcttgga ggg                                              23

SEQ ID NO: 27           moltype = DNA  length = 24
FEATURE                 Location/Qualifiers
misc_feature            1..24
                        note = sgRNA target sequence
source                  1..24
                        mol_type = other DNA
                        organism = synthetic construct
SEQUENCE: 27
ggcacatggt ggggaaagct tgga                                             24

SEQ ID NO: 28           moltype = DNA  length = 24
FEATURE                 Location/Qualifiers
misc_feature            1..24
                        note = sgRNA target sequence
source                  1..24
                        mol_type = other DNA
                        organism = synthetic construct
SEQUENCE: 28
aaactccaag ctttccccac catg                                             24

SEQ ID NO: 29           moltype = DNA  length = 23
FEATURE                 Location/Qualifiers
misc_feature            1..23
                        note = sgRNA target sequence
source                  1..23
                        mol_type = other DNA
                        organism = synthetic construct
SEQUENCE: 29
ccggacgacg acgtcgacga cgg                                              23

SEQ ID NO: 30           moltype = DNA  length = 24
FEATURE                 Location/Qualifiers
misc_feature            1..24
                        note = sgRNA target sequence
source                  1..24
                        mol_type = other DNA
                        organism = synthetic construct
SEQUENCE: 30
ggcaccggac gacgacgtcg acga                                             24

SEQ ID NO: 31           moltype = DNA  length = 24
FEATURE                 Location/Qualifiers
misc_feature            1..24
                        note = sgRNA target sequence
source                  1..24
                        mol_type = other DNA
                        organism = synthetic construct
SEQUENCE: 31
aaactcgtcg acgtcgtcgt ccgg                                             24

SEQ ID NO: 32           moltype = DNA  length = 23
FEATURE                 Location/Qualifiers
misc_feature            1..23
                        note = sgRNA target sequence
source                  1..23
                        mol_type = other DNA
                        organism = synthetic construct
SEQUENCE: 32
ttgaagtccc ttctagatgg agg                                              23

SEQ ID NO: 33           moltype = DNA  length = 24
FEATURE                 Location/Qualifiers
misc_feature            1..24
                        note = sgRNA target sequence
source                  1..24
                        mol_type = other DNA
                        organism = synthetic construct
SEQUENCE: 33
ggcattgaag tcccttctag atgg                                             24

SEQ ID NO: 34           moltype = DNA  length = 24
FEATURE                 Location/Qualifiers
misc_feature            1..24
```

```
                            note = sgRNA target sequence
source                      1..24
                            mol_type = other DNA
                            organism = synthetic construct
SEQUENCE: 34
aaacccatct agaagggact tcaa                                              24

SEQ ID NO: 35               moltype = DNA  length = 23
FEATURE                     Location/Qualifiers
misc_feature                1..23
                            note = sgRNA target sequence
source                      1..23
                            mol_type = other DNA
                            organism = synthetic construct
SEQUENCE: 35
actgcgacac ccagatatcg tgg                                               23

SEQ ID NO: 36               moltype = DNA  length = 24
FEATURE                     Location/Qualifiers
misc_feature                1..24
                            note = sgRNA target sequence
source                      1..24
                            mol_type = other DNA
                            organism = synthetic construct
SEQUENCE: 36
ggcaactgcg acacccagat atcg                                              24

SEQ ID NO: 37               moltype = DNA  length = 24
FEATURE                     Location/Qualifiers
misc_feature                1..24
                            note = sgRNA target sequence
source                      1..24
                            mol_type = other DNA
                            organism = synthetic construct
SEQUENCE: 37
aaaccgatat ctgggtgtcg cagt                                              24

SEQ ID NO: 38               moltype = DNA  length = 23
FEATURE                     Location/Qualifiers
source                      1..23
                            mol_type = other DNA
                            organism = Oryza sativa
SEQUENCE: 38
gttggtcttt gctcctgcag agg                                               23

SEQ ID NO: 39               moltype = DNA  length = 24
FEATURE                     Location/Qualifiers
misc_feature                1..24
                            note = sgRNA target sequence
source                      1..24
                            mol_type = other DNA
                            organism = synthetic construct
SEQUENCE: 39
ggcagttggt ctttgctcct gcag                                              24

SEQ ID NO: 40               moltype = DNA  length = 24
FEATURE                     Location/Qualifiers
misc_feature                1..24
                            note = sgRNA target sequence
source                      1..24
                            mol_type = other DNA
                            organism = synthetic construct
SEQUENCE: 40
aaacctgcag gagcaaagac caac                                              24

SEQ ID NO: 41               moltype = DNA  length = 24
FEATURE                     Location/Qualifiers
misc_feature                1..24
                            note = Oligo-F sequence
source                      1..24
                            mol_type = other DNA
                            organism = synthetic construct
SEQUENCE: 41
tgcaaggtcg gggaggggac gtac                                              24

SEQ ID NO: 42               moltype = DNA  length = 24
FEATURE                     Location/Qualifiers
misc_feature                1..24
                            note = Oligo-F sequence
```

```
source                  1..24
                        mol_type = other DNA
                        organism = synthetic construct
SEQUENCE: 42
tgcagacgtc ggcgaggaag gcct                                          24

SEQ ID NO: 43           moltype = DNA   length = 24
FEATURE                 Location/Qualifiers
misc_feature            1..24
                        note = Oligo-F sequence
source                  1..24
                        mol_type = other DNA
                        organism = synthetic construct
SEQUENCE: 43
tgcacatggt ggggaaagct tgga                                          24

SEQ ID NO: 44           moltype = DNA   length = 24
FEATURE                 Location/Qualifiers
misc_feature            1..24
                        note = Oligo-F sequence
source                  1..24
                        mol_type = other DNA
                        organism = synthetic construct
SEQUENCE: 44
tgcaccggac gacgacgtcg acga                                          24

SEQ ID NO: 45           moltype = DNA   length = 24
FEATURE                 Location/Qualifiers
misc_feature            1..24
                        note = Oligo-F sequence
source                  1..24
                        mol_type = other DNA
                        organism = synthetic construct
SEQUENCE: 45
tgcattgaag tcccttctag atgg                                          24

SEQ ID NO: 46           moltype = DNA   length = 23
FEATURE                 Location/Qualifiers
misc_feature            1..23
                        note = Oligo-F sequence
source                  1..23
                        mol_type = other DNA
                        organism = synthetic construct
SEQUENCE: 46
tgcactgcga cacccagata tcg                                           23

SEQ ID NO: 47           moltype = DNA   length = 24
FEATURE                 Location/Qualifiers
misc_feature            1..24
                        note = Oligo-F sequence
source                  1..24
                        mol_type = other DNA
                        organism = synthetic construct
SEQUENCE: 47
tgcagttggt ctttgctcct gcag                                          24

SEQ ID NO: 48           moltype = DNA   length = 23
FEATURE                 Location/Qualifiers
misc_feature            1..23
                        note = Oligo-F sequence
source                  1..23
                        mol_type = other DNA
                        organism = synthetic construct
SEQUENCE: 48
ggcgttggtc tttgctcctg cag                                           23

SEQ ID NO: 49           moltype = DNA   length = 23
FEATURE                 Location/Qualifiers
misc_feature            1..23
                        note = Oligo-F sequence
source                  1..23
                        mol_type = other DNA
                        organism = synthetic construct
SEQUENCE: 49
ggcgttggtc tttgctcctg cag                                           23

SEQ ID NO: 50           moltype = DNA   length = 23
FEATURE                 Location/Qualifiers
source                  1..23
```

```
                    mol_type = other DNA
                    organism = Homo sapiens
SEQUENCE: 50
ggtgagtgag tgtgtgcgtg tgg                                          23

SEQ ID NO: 51       moltype = DNA   length = 24
FEATURE             Location/Qualifiers
misc_feature        1..24
                    note = Oligo-F sequence
source              1..24
                    mol_type = other DNA
                    organism = synthetic construct
SEQUENCE: 51
caccggtgag tgagtgtgtg cgtg                                         24

SEQ ID NO: 52       moltype = DNA   length = 24
FEATURE             Location/Qualifiers
misc_feature        1..24
                    note = Oligo-R sequence
source              1..24
                    mol_type = other DNA
                    organism = synthetic construct
SEQUENCE: 52
aaaccacgca cacactcact cacc                                         24

SEQ ID NO: 53       moltype = DNA   length = 25
FEATURE             Location/Qualifiers
misc_feature        1..25
                    note = Oligo-F sequence
source              1..25
                    mol_type = other DNA
                    organism = synthetic construct
SEQUENCE: 53
caccgggtga gtgagtgtgt gcgtg                                        25

SEQ ID NO: 54       moltype = DNA   length = 25
FEATURE             Location/Qualifiers
misc_feature        1..25
                    note = Oligo-R sequence
source              1..25
                    mol_type = other DNA
                    organism = synthetic construct
SEQUENCE: 54
aaaccacgca cacactcact caccc                                        25

SEQ ID NO: 55       moltype = DNA   length = 102
FEATURE             Location/Qualifiers
misc_feature        1..102
                    note = Oligo-F sequence
source              1..102
                    mol_type = other DNA
                    organism = synthetic construct
SEQUENCE: 55
caccgaacaa agcaccagtg gtctagtggt agaatagtac cctgccacgg tacagacccg  60
ggttcgattc ccggctggtg caggtgagtg agtgtgtgcg tg                    102

SEQ ID NO: 56       moltype = DNA   length = 102
FEATURE             Location/Qualifiers
misc_feature        1..102
                    note = Oligo-R sequence
source              1..102
                    mol_type = other DNA
                    organism = synthetic construct
SEQUENCE: 56
aaaccacgca cacactcact cacctgcacc agccgggaat cgaacccggg tctgtaccgt  60
ggcagggtac tattctacca ctagaccact ggtgctttgt tc                    102

SEQ ID NO: 57       moltype =   length =
SEQUENCE: 57
000

SEQ ID NO: 58       moltype =   length =
SEQUENCE: 58
000

SEQ ID NO: 59       moltype = DNA   length = 27
FEATURE             Location/Qualifiers
misc_feature        1..27
                    note = sgRNA sequence
```

-continued

```
source                  1..27
                        mol_type = other DNA
                        organism = synthetic construct
SEQUENCE: 59
tggagttggt ctttgctcct gcagagg                                            27

SEQ ID NO: 60           moltype = DNA   length = 23
FEATURE                 Location/Qualifiers
source                  1..23
                        mol_type = other DNA
                        organism = Oryza sativa
SEQUENCE: 60
gacgccggcg aggaaggcct cgg                                                23

SEQ ID NO: 61           moltype = DNA   length = 23
FEATURE                 Location/Qualifiers
source                  1..23
                        mol_type = other DNA
                        organism = Oryza sativa
SEQUENCE: 61
gcagtcggag aggaaggcct ggg                                                23

SEQ ID NO: 62           moltype = DNA   length = 23
FEATURE                 Location/Qualifiers
source                  1..23
                        mol_type = other DNA
                        organism = Oryza sativa
SEQUENCE: 62
agatcgggga ggggacgtac ggg                                                23

SEQ ID NO: 63           moltype = DNA   length = 23
FEATURE                 Location/Qualifiers
source                  1..23
                        mol_type = other DNA
                        organism = Oryza sativa
SEQUENCE: 63
aggtggggga agggacgtac ggg                                                23

SEQ ID NO: 64           moltype = DNA   length = 23
FEATURE                 Location/Qualifiers
source                  1..23
                        mol_type = other DNA
                        organism = Oryza sativa
SEQUENCE: 64
agattgggga gggcacgtac ggg                                                23

SEQ ID NO: 65           moltype = DNA   length = 23
FEATURE                 Location/Qualifiers
source                  1..23
                        mol_type = other DNA
                        organism = Streptococcus pyogenes
SEQUENCE: 65
agcgtcggcg aggaaggcct cgg                                                23

SEQ ID NO: 66           moltype = DNA   length = 23
FEATURE                 Location/Qualifiers
source                  1..23
                        mol_type = other DNA
                        organism = Streptococcus pyogenes
SEQUENCE: 66
ggtgtcggcg aggaaggcct cgg                                                23

SEQ ID NO: 67           moltype = DNA   length = 23
FEATURE                 Location/Qualifiers
source                  1..23
                        mol_type = other DNA
                        organism = Streptococcus pyogenes
SEQUENCE: 67
gatatcggcg aggaaggcct cgg                                                23

SEQ ID NO: 68           moltype = DNA   length = 23
FEATURE                 Location/Qualifiers
source                  1..23
                        mol_type = other DNA
                        organism = Streptococcus pyogenes
SEQUENCE: 68
gacaccggcg aggaaggcct cgg                                                23

SEQ ID NO: 69           moltype = DNA   length = 23
```

```
                        -continued

FEATURE                 Location/Qualifiers
source                  1..23
                        mol_type = other DNA
                        organism = Streptococcus pyogenes
SEQUENCE: 69
gacgctggcg aggaaggcct cgg                                           23

SEQ ID NO: 70           moltype = DNA   length = 23
FEATURE                 Location/Qualifiers
source                  1..23
                        mol_type = other DNA
                        organism = Streptococcus pyogenes
SEQUENCE: 70
gacgttagcg aggaaggcct cgg                                           23

SEQ ID NO: 71           moltype = DNA   length = 23
FEATURE                 Location/Qualifiers
source                  1..23
                        mol_type = other DNA
                        organism = Streptococcus pyogenes
SEQUENCE: 71
gacgtcaacg aggaaggcct cgg                                           23

SEQ ID NO: 72           moltype = DNA   length = 23
FEATURE                 Location/Qualifiers
source                  1..23
                        mol_type = other DNA
                        organism = Streptococcus pyogenes
SEQUENCE: 72
gacgtcgatg aggaaggcct cgg                                           23

SEQ ID NO: 73           moltype = DNA   length = 23
FEATURE                 Location/Qualifiers
source                  1..23
                        mol_type = other DNA
                        organism = Streptococcus pyogenes
SEQUENCE: 73
gacgtcggta aggaaggcct cgg                                           23

SEQ ID NO: 74           moltype = DNA   length = 23
FEATURE                 Location/Qualifiers
source                  1..23
                        mol_type = other DNA
                        organism = Streptococcus pyogenes
SEQUENCE: 74
gacgtcggca gggaaggcct cgg                                           23

SEQ ID NO: 75           moltype = DNA   length = 23
FEATURE                 Location/Qualifiers
source                  1..23
                        mol_type = other DNA
                        organism = Streptococcus pyogenes
SEQUENCE: 75
gacgtcggcg gagaaggcct cgg                                           23

SEQ ID NO: 76           moltype = DNA   length = 23
FEATURE                 Location/Qualifiers
source                  1..23
                        mol_type = other DNA
                        organism = Streptococcus pyogenes
SEQUENCE: 76
gacgtcggcg aaaaaggcct cgg                                           23

SEQ ID NO: 77           moltype = DNA   length = 23
FEATURE                 Location/Qualifiers
source                  1..23
                        mol_type = other DNA
                        organism = Streptococcus pyogenes
SEQUENCE: 77
gacgtcggcg agagaggcct cgg                                           23

SEQ ID NO: 78           moltype = DNA   length = 23
FEATURE                 Location/Qualifiers
source                  1..23
                        mol_type = other DNA
                        organism = Streptococcus pyogenes
SEQUENCE: 78
gacgtcggcg aggggggcct cgg                                           23
```

```
SEQ ID NO: 79         moltype = DNA   length = 23
FEATURE               Location/Qualifiers
source                1..23
                      mol_type = other DNA
                      organism = Streptococcus pyogenes
SEQUENCE: 79
gacgtcggcg aggagagcct cgg                                              23

SEQ ID NO: 80         moltype = DNA   length = 23
FEATURE               Location/Qualifiers
source                1..23
                      mol_type = other DNA
                      organism = Streptococcus pyogenes
SEQUENCE: 80
gacgtcggcg aggaaaacct cgg                                              23

SEQ ID NO: 81         moltype = DNA   length = 23
FEATURE               Location/Qualifiers
source                1..23
                      mol_type = other DNA
                      organism = Streptococcus pyogenes
SEQUENCE: 81
gacgtcggcg aggaagatct cgg                                              23

SEQ ID NO: 82         moltype = DNA   length = 23
FEATURE               Location/Qualifiers
source                1..23
                      mol_type = other DNA
                      organism = Streptococcus pyogenes
SEQUENCE: 82
gacgtcggcg aggaaggttt cgg                                              23

SEQ ID NO: 83         moltype = DNA   length = 23
FEATURE               Location/Qualifiers
source                1..23
                      mol_type = other DNA
                      organism = Streptococcus pyogenes
SEQUENCE: 83
gacgtcggcg aggaaggctc cgg                                              23

SEQ ID NO: 84         moltype = DNA   length = 23
FEATURE               Location/Qualifiers
source                1..23
                      mol_type = other DNA
                      organism = Streptococcus pyogenes
SEQUENCE: 84
gctgagtgag tgtatgcgtg tgg                                              23

SEQ ID NO: 85         moltype = DNA   length = 23
FEATURE               Location/Qualifiers
source                1..23
                      mol_type = other DNA
                      organism = Streptococcus pyogenes
SEQUENCE: 85
tgtgggtgag tgtgtgcgtg agg                                              23
```